US007767815B2

(12) United States Patent
Bennett et al.

(10) Patent No.: US 7,767,815 B2
(45) Date of Patent: Aug. 3, 2010

(54) FUSED TRICYCLIC MGLUR1 ANTAGONISTS AS THERAPEUTIC AGENTS

(75) Inventors: Chad E. Bennett, Metuchen, NJ (US); Wen-Lian Wu, Edison, NJ (US); Duane A. Burnett, Bernardsville, NJ (US)

(73) Assignee: Schering Corporation, Kenilworth, NJ (US)

( * ) Notice: Subject to any disclaimer, the term of this patent is extended or adjusted under 35 U.S.C. 154(b) by 1009 days.

(21) Appl. No.: 11/504,860

(22) Filed: Aug. 16, 2006

(65) Prior Publication Data

US 2007/0072863 A1    Mar. 29, 2007

Related U.S. Application Data

(60) Provisional application No. 60/709,475, filed on Aug. 19, 2005.

(51) Int. Cl.
*C07D 409/14*    (2006.01)
*A61K 31/4365*    (2006.01)

(52) U.S. Cl. .......................... 546/83; 514/293

(58) Field of Classification Search .................. 546/83; 514/293
See application file for complete search history.

(56) References Cited

U.S. PATENT DOCUMENTS

| 5,783,575 | A | 7/1998 | Jakobsen et al. |
| 2006/0009477 | A1 | 1/2006 | Matasi et al. |
| 2006/0167029 | A1 | 7/2006 | Matasi et al. |
| 2007/0072864 | A1 | 3/2007 | Bennett et al. |

FOREIGN PATENT DOCUMENTS

WO    WO 02/062803    8/2002

OTHER PUBLICATIONS

Dorwald F. A. Side Reactions in Organic Synthesis, 2005, Wiley: VCH, Weinheim p. IX of Preface.*
U.S. Appl. No. 11/524,867, filed Sep. 21, 2006, Burnette, et al.
Tacconi G., et al., "Indolizzazione di 3-piri-dilidrazoni della 2,3-dichetopiperidina", Annali Di Chimica, Societa Chimica Italiana, Tome, IT., 1965, pp. 1223-1232, vol. 55, No. 12 —XP008073061.
International Search Report for International Application No. PCT/US2006/031972, mailed Jan. 16, 2007 (4 pages) for CN06342.

* cited by examiner

*Primary Examiner*—Rita J Desai
(74) *Attorney, Agent, or Firm*—Kenrick L. Vidale; John C. Todaro; Keith D. MacMillan

(57) ABSTRACT

In its many embodiments, the present invention provides tricyclic compounds of formula I (wherein $J^1$-$J^3$, X, Z, and $R^1$-$R^4$ are defined herein) useful as metabotropic glutamate receptor (mGluR) antagonists, particularly as selective metabotropic glutamate receptor 1 antagonists, pharmaceutical compositions containing the compounds, and methods of treatment using the compounds and compositions to treat diseases associated with metabotropic glutamate receptor (e.g., mGluR1) such as, for example, pain, migraine, anxiety, urinary incontinence and neurodegenerative diseases such as Alzheimer's disease.

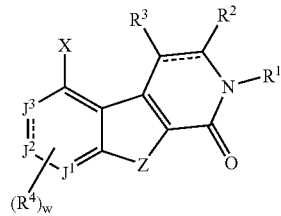

formula I

22 Claims, No Drawings

FUSED TRICYCLIC MGLUR1 ANTAGONISTS AS THERAPEUTIC AGENTS

This Application claims the benefit of U.S. Provisional Application Ser. No. 60/709,475 filed Aug. 19, 2005, which is incorporated herein by reference in its entirety.

FIELD OF THE INVENTION

The present invention relates to fused tricyclic compounds useful as metabotropic glutamate receptor (mGluR) antagonists, particularly as selective metabotropic glutamate receptor 1 antagonists, pharmaceutical compositions containing the compounds, and methods of treatment using the compounds and compositions to treat diseases associated with metabotropic glutamate receptor (e.g., mGluR1) such as, for example, pain, migraine, anxiety, urinary incontinence and neurodegenerative diseases such as Alzheimer's disease.

BACKGROUND OF THE INVENTION

Glutamate is an important excitatory neurotransmitter in the mammalian central nervous system. Glutamate synaptic responses in the central nervous system (CNS) are mediated via activation of two families of receptors: ligand-gated cation channels, referred to as ionotropic glutamate receptors, and G-protein-coupled receptors known as metabotropic glutamate receptors (mGluRs). Thus far, eight mGluR subtypes, together with splice variants, have been cloned and characterized in functional studies (Schoepp et al. *Neuropharmacology*, 1999, 38, 1431-1476). The eight mGluRs are grouped into three classes based on structural homology, pharmacology, and signal transduction mechanisms.

Group I receptors (mGluR1 and mGluR5) couple through $G_q/_{11}$ proteins to the activation of phospholipase C (PLC) resulting in phosphoinositide (PI) hydrolysis, the release of calcium from intracellular stores. While group II (mGluR2 and mGluR3) and III (mGluR4, mGluR6 mGluR7 and mGluR8) are negatively coupled to adenyl cyclase (AC) through $G_i/G_o$ proteins thereby inhibiting cyclic AMP (cAMP) formation (A. Francesconi and R. M. Duvoisin, *J. Biol. Chem.* 1998, 273(10), 5615-5624).

Glutamate and Pain

Chronic pain is an area of high unmet medical need. Current therapies are not adequate and chronic pain is often refractory to most commonly used analgesics, including opioids. Glutamate plays a major role in nociceptive processing. Glutamate receptors, including mGluRs, are expressed in relevant areas of the brain, spinal cord and periphery that are involved in pain sensation and transmission.

Chronic pain may be due to tissue injury and diseases (inflammatory pain) or to the central and peripheral nervous system (neuropathic pain) and is associated with severe chronic sensory disturbances characterized by spontaneous pain, hyperalgesia (exaggerated responsiveness to painful stimuli) and allodynia (wrong perception of non-noxious stimuli as painful). Prevalent symptoms in human patients include cold hyperalgesia, mechanical allodynia and less commonly, heat hyperalgesia.

Chronic pain is a true disease. It is believed to be a result of the plasticity at synapses in nociceptive processing centers, a phenomenon referred to as "central sensitization" which consists of increased excitability of spinal cord dorsal horn neurons. Glutamate receptors have been identified for their key role in central sensitization. Plasticity at synapses involved in nociceptive processing requires activation of ionotropic glutamate receptors such as NMDA and this plasticity is modulated by mGluRs including mGluR1. NMDA receptor antagonists have been tested in experimental therapies for the prevention and treatment of persistent pain following injury. However, there are significant undesirable side effects associated with the use of NMDA antagonists due largely to the critical role of those receptors in normal excitatory synaptic transmission throughout the nervous system. These side effects include pyschosis, hyperactivity, fatigue, dizziness, and in the case of higher levels of NMDA antagonists, amnesia and neuronal toxicity. Drugs designed to antagonize mGluR1 receptors are expected to have less side effect liability since they appear to selectively modulate the pathologically abnormal spinal NMDA receptor activation associated with persistent pain states whilst having little effect on the normal spinal synaptic processes involved in non-painful sensory perception. Thus, mGluR antagonists might perform well clinically in chronic pain states because they avoid the side effects inherent to widespread spinal and supraspinal NMDA receptor antagonism.

mGluR1 and Pain

A number of behavioral (Fisher et al. *Neuroreport*, 1998, 20, 1169-1172; Fundytus et al. *Neuroreport*, 1998, 9, 731-735; Bhave et al. *Nature Neurosci.*, 2001, 4, 417-423; Dolan et al. *Neurophamacology*, 2002, 43, 319-326; Dolan et al. *Pain*, 2003, 106, 501-512) and electrophysiological (Young et al. *Neuropharmacology*, 1994, 33, 141-144; and Young et al. *Brain Res.*, 1997, 777, 161-169) studies have demonstrated a specific role for Group I mGluRs, and in particular mGluR1 receptors, in nociceptive processing in the CNS, including mechanisms of hyperalgesia and inflammation. In the spinal cord, mGluR1 appears to be localized primarily on postsynaptic elements throughout the dorsal and ventral horns. (Neugebauer, *Trends Neurosci.*, 2001, 24, 550-552). The intrinsic activation of spinal mGluR1 in chronic nociception has been demonstrated using antagonists, antibodies and antisense oligonucleotides. Intrathecal administration of an mGluR1 antagonist produced antinociceptive effects in the second phase of formalin-induced nociceptive behavior (Neugebauer, *Trends Neurosci.*, 2001, 24, 550-552). Behavioral studies have also addressed the role of spinal mGluR1 receptors in the spinal injury and ligation models of neuropathic pain. Expression of mGluR1 is increased in rats following spinal cord injury and this may mediate the chronic central pain induced by the injury (Mills and Hulsebosch, *Neurosci. Lett.*, 2002, 319, 59-62). Knockdown of spinal mGluR1 by intrathecal infusion of antisense oligonucleotides attenuated cold hyperalgesia and mechanical allodynia in neuropathic rats (Fundytus et al. *Br. J. Pharmacol.*, 2001, 132, 354-367; and Fundytus et al. *Pharmacol. Biochem. Behav.*, 2002, 73, 401-410). Additionally, spinal administration of anti-mGluR1 IgG antibodies reduced cold hyperalgesia, but not mechanical allodynia, in neuropathic rats (Fundytus et al. *Neuroreport*, 1998, 9, 731-735). The critical role of spinal mGluR1 receptors in pain-related central sensitization is emphasized at the single cell level by electrophysiological in vivo studies in anesthetized animals. Intraspinal administration of an mGluR1 antagonist inhibited the responses of primate spinothalamic tract neurons to brief noxious, but not innocuous, mechanical cutaneous stimuli, as well as central sensitization in the capsaicin pain model (Neugebauer et al. *J. Neurophysiol.*, 1999, 82, 272-282). In rats with knocked down mGluR1 expression, the responses of multireceptive dorsal horn neurons to noxious input evoked by repeated topical applications of the C-fiber irritant mustard oil were significantly reduced compared to control neurons; the

SUMMARY OF THE INVENTION

In its many embodiments, the present invention provides a novel class of tricyclic compounds useful as metabotropic glutamate receptor (mGluR) antagonists, particularly as selective mGluR1 antagonists, pharmaceutical compositions comprising one or more such compounds, methods of preparing pharmaceutical formulations comprising one or more such compounds, and methods of treatment, prevention, inhibition or amelioration of one or more diseases associated with the mGluRs, particularly mGluR1, using such compounds or pharmaceutical compositions.

In one aspect, the present application discloses a compound of formula I:

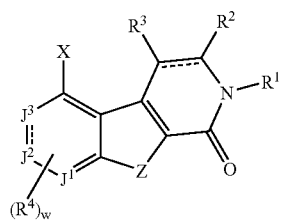

formula I or a pharmaceutically acceptable salt, solvate, or ester thereof, wherein:

$J^1$, $J^2$, and $J^3$ are independently N or C, provided that 1-2 of $J^1$, $J^2$, and $J^3$ are N;

----- is a single or double bond;

$R^1$ is selected from the group consisting of H, —$NR^5R^6$, —$OR^6$, —$SR^{11}$, —CN, —$C(O)R^6$, —$C(O_2)R^6$, —$OC(O)R^6$, —$C(O)NR^6R^7$, —$N(R^6)C(O)R^6$, —$S(O_2)NR^6R^7$—$N(R^6)S(O_2)R^{11}$, —$N(R^6)C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$, or wherein said $R^1$ aryl may optionally be substituted with two radicals on adjacent carbon atoms, which radicals are taken together with the carbon atoms to which they are attached to form a five to six membered heterocyclyl or heteroaryl ring which ring is optionally substituted one at least one $R^8$;

X is selected from the group consisting of H, —$NR^5R^6$, —$OR^7$, —$SR^{11}$, —$C(O)R^6$, —$SO_2R^{11}$, —$C(O)NR^6R^7$, and alkyl, alkoxy, alkenyloxy, alkynyl, cycloalkyl, cycloalkoxy, aryloxy, arylalkyl, heteroaryl, heteroarylalkyl, heterocyclyl, and heterocyclylalkyl groups optionally substituted with at least one $R^8$;

Z is selected from the group consisting of S, O, and $NR^5$;

$R^2$ and $R^3$ are each independently selected from the group consisting of H, halo, —CN, —$NO_2$, —$OR^7$, —$SR^{11}$, —$NR^5R^6$, —$C(O)R^6$, —$C(O_2)R^6$, —$OC(O)R^6$, —$C(O)NR^6R^7$, —$N(R^9)C(O)R^6$, —$OS(O_2)R^{11}$, —$S(O_2)R^{11}$, —$S(O_2)NR^5R^6$, —$N(R^6)S(O_2)R^{11}$, and —$N(R^9)C(O)NR^5R^6$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^4$ is independently selected from the group consisting of H, halo, —CN, —$NHC(O)R^6$, —$NHSO_2R^{11}$, —$NR^5R^6$, —$OR^7$, —$C(O)R^6$, —$C(O_2)R^6$, —$C(O)NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$; or, when w=2, two $R^4$ taken together with the carbon atoms to which they are attached, form a group of the formula:

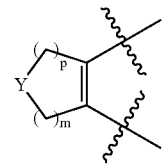

where m and p are each an integer ranging from 0-4, provided that (m+p)=2-7, and Y is selected from the group consisting of S, S(O), S(O)$_2$, O, $NR^7$, $NC(O)R^7$, $NC(O)N(R^7)_2$, $NSO_2R^{11}$, —$CH_2$—, CH(OH), and C(O);

w is an integer ranging from 1-2;

$R^5$ is selected from the group consisting of H, halo, —$NH_2$, —$C(O)R^6$, —$SO_2R^{11}$, $C(O)NR^6R^7$, and alkyl, alkenyl, alkynyl, cycloalkyl, aryl, arylalkyl, heteroaryl, heteroarylalkyl, heterocyclyl, and heterocyclylalkyl groups optionally substituted with at least one $R^8$;

$R^6$ and $R^7$ are independently selected from the group consisting of H and alkyl, alkenyl, alkynyl, cycloalkyl, aryl, arylalkyl, heteroaryl, heteroarylalkyl, heterocyclyl, and heterocyclylalkyl groups optionally substituted with at least one $R^8$; or $R^5$ and $R^6$ or $R^6$ and $R^7$, when attached to the same nitrogen atom, optionally taken together with the nitrogen atom form a 3-8 membered heterocyclic ring containing 0-3 heteroatoms independently selected from O, N or S in addition to said nitrogen atom;

$R^8$ is selected from the group consisting of H, halo, —$OR^9$, $NO_2$, —CN, —$NR^9C(O)R^{10}$, —$NR^9SO_2R^{11}$, —$NR^9R^{10}$, —$C(O)R^{10}$, —$C(O)NR^5R^6$, $S(O_2)NR^5R^6$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one of halo, —CN, —$NO_2$, —$OR^6$, —$SR^{11}$, —$NR^5R^6$, —$C(O)R^6$, —$C(O_2)R^6$, —$OC(O)R^6$, —$C(O)NR^6R^7$, —$N(R^6)C(O)R^6$, —$OS(O_2)R^1$, —$S(O_2)R^{11}$, —$S(O_2)NR^5R^6$, —$N(R^6)S(O_2)R^{11}$, —$N(R^6)C(O)NR^5R^6$, and —$NR^9SO_2R^{11}$;

$R^9$ is selected from the group consisting of H, and alkyl, alkenyl, alkynyl, cycloalkyl, aryl, arylalkyl, heteroaryl, heteroarylalkyl, heterocyclyl, and heterocyclylalkyl groups optionally substituted with at least one of halo, —CN, —$NO_2$, —$OR^6$, —$SR^{11}$, —$NR^5R^6$, —$C(O)R^6$, —$C(O_2)R^6$, —$OC(O)R^6$, —$C(O)NR^6R^7$, —$N(R^6)C(O)R^6$, —$OS(O_2)R^{11}$, —$S(O_2)R^{11}$, —$S(O_2)NR^5R^6$, —$N(R^6)S(O_2)R^{11}$, and —$N(R^6)C(O)NR^5R^6$;

$R^{10}$ is selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, and heterocyclyl groups optionally substituted with at least one of halo, —CN, —$NO_2$, —$OR^6$, —$SR^{11}$, —$NR^5R^6$, —$C(O)R^6$, —$C(O_2)R^6$, —$OC(O)R^6$, —$C(O)NR^6R^7$, —$N(R^6)C(O)R^6$, —$OS(O_2)R^{11}$, —$S(O_2)R^{11}$, —$S(O_2)NR^5R^6$, —$N(R^6)S(O_2)R^{11}$, and —$N(R^6)C(O)NR^5R^6$; and $R^{11}$ is selected from the group consisting of alkyl, alkenyl, alkynyl, cycloalkyl, aryl, arylalkyl, heteroaryl, heteroarylalkyl, and heterocyclyl groups optionally substituted with at least one $R^8$.

In another aspect, the present application discloses a compound of formula I:

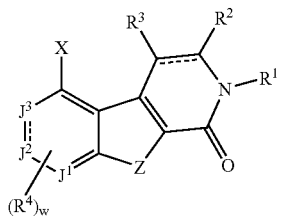

formula I or a pharmaceutically acceptable salt, solvate, or ester thereof, wherein:

$J^1$, $J^2$, and $J^3$ are independently N or C, provided that 1-2 of $J^1$, $J^2$, and $J^3$ are N;

------ is a single or double bond;

$R^1$ is selected from the group consisting of H, —$NR^5R^6$, —$OR^6$, —$SR^{11}$, —CN, —C(O)$R^6$, —C(O$_2$)$R^6$, —OC(O)$R^6$, —C(O)$NR^6R^7$, —N($R^6$)C(O)$R^6$, —S(O$_2$)$NR^6R^7$—N($R^6$)S(O$_2$)$R^{11}$, —N($R^6$)C(O)$NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

X is selected from the group consisting of H, —$NR^5R^6$, —$OR^7$, —$SR^{11}$, —C(O)$R^6$, —SO$_2R^{11}$, —C(O)$NR^6R^7$, and alkyl, alkoxy, alkenyloxy, alkynyl, cycloalkyl, cycloalkoxy, aryloxy, arylalkyl, heteroaryl, heteroarylalkyl, heterocyclyl, and heterocyclylalkyl groups optionally substituted with at least one $R^8$;

Z is selected from the group consisting of S, O, and $NR^5$;

$R^2$ and $R^3$ are each independently selected from the group consisting of H, halo, —CN, —NO$_2$, —$OR^7$, —$SR^{11}$, —$NR^5R^6$, —C(O)$R^6$, —C(O$_2$)$R^6$, —OC(O)$R^6$, —C(O)$NR^6R^7$, —N($R^9$)C(O)$R^6$, —OS(O$_2$)$R^{11}$, —S(O$_2$)$R^{11}$, —S(O$_2$)$NR^5R^6$, —N($R^6$)S(O$_2$)$R^{11}$, and —N($R^9$)C(O)$NR^5R^6$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$;

$R^4$ is independently selected from the group consisting of H, halo, —CN, —NHC(O)$R^6$, —NHSO$_2R^{11}$, —$NR^5R^6$, —$OR^7$, —C(O)$R^6$, —C(O$_2$)$R^6$, —C(O)$NR^6R^7$; and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^8$; or, when w=2, two $R^4$ taken together with the carbon atoms to which they are attached, form a group of the formula:

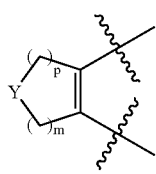

where m and p are each an integer ranging from 0-4, provided that (m+p)=2-7, and Y is selected from the group consisting of S, S(O), S(O)$_2$, O, $NR^7$, NC(O)$R^7$, NC(O)N($R^7$)$_2$, NSO$_2R^{11}$, —CH$_2$—, CH(OH), and C(O);

w is an integer ranging from 1-2;

$R^5$ is selected from the group consisting of H, halo, —C(O)$R^6$, —SO$_2R^{11}$, C(O)$NR^6R^7$, and alkyl, alkenyl, alkynyl, cycloalkyl, aryl, arylalkyl, heteroaryl, heteroarylalkyl, heterocyclyl, and heterocyclylalkyl groups optionally substituted with at least one $R^8$;

$R^6$ and $R^7$ are independently selected from the group consisting of H and alkyl, alkenyl, alkynyl, cycloalkyl, aryl, arylalkyl, heteroaryl, heteroarylalkyl, heterocyclyl, and heterocyclylalkyl groups optionally substituted with at least one $R^8$; or $R^5$ and $R^6$ or $R^6$ and $R^7$, when attached to the same nitrogen atom, optionally taken together with the nitrogen atom form a 3-8 membered heterocyclic ring containing 0-3 heteroatoms independently selected from O, N or S in addition to said nitrogen atom;

$R^8$ is selected from the group consisting of H, halo, —$OR^9$, NO$_2$, —CN, —$N R^9$C(O)$R^{10}$, —$NR^9$SO$_2R^{11}$, —$NR^9R^{10}$, —C(O)$R^{10}$, —C(O)$NR^5R^6$, S(O$_2$)$NR^5R^6$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one of halo, —CN, —NO$_2$, —$OR^6$, —$SR^{11}$, —$NR^5R^6$, —C(O)$R^6$, —C(O$_2$)$R^6$, —OC(O)$R^6$, —C(O)$NR^6R^7$, —N($R^6$)C(O)$R^6$, —OS(O$_2$)$R^{11}$, —S(O$_2$)$R^{11}$, —S(O$_2$)$NR^5R^6$, —N($R^6$)S(O$_2$)$R^{11}$, —N($R^6$)C(O)$NR^5R^6$, and —$NR^9$SO$_2R^{11}$;

$R^9$ is selected from the group consisting of H, and alkyl, alkenyl, alkynyl, cycloalkyl, aryl, arylalkyl, heteroaryl, heteroarylalkyl, heterocyclyl, and heterocyclylalkyl groups optionally substituted with at least one of halo, —CN, —NO$_2$, —$OR^6$, —$SR^{11}$, —$NR^5R^6$, —C(O)$R^6$, —C(O$_2$)$R^6$, —OC(O)$R^6$, —C(O)$NR^6R^7$, —N($R^6$)C(O)$R^6$, —OS(O$_2$)$R^{11}$, —S(O$_2$)$R^{11}$, —S(O$_2$)$NR^5R^6$, —N($R^6$)S(O$_2$)$R^{11}$, and —N($R^6$)C(O)$NR^5R^6$;

$R^{10}$ is selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, and heterocyclyl groups optionally substituted with at least one of halo, —CN, —NO$_2$, —$OR^6$, —$SR^{11}$, —$NR^5R^6$, —C(O)$R^6$, —C(O$_2$)$R^6$, —OC(O)$R^6$, —C(O)$NR^6R^7$, —N($R^6$)C(O)$R^6$, —OS(O$_2$)$R^{11}$, —S(O$_2$)$R^{11}$, —S(O$_2$)$NR^5R^6$, —N($R^6$)S(O$_2$)$R^{11}$, and —N($R^6$)C(O)$NR^5R^6$; and $R^{11}$ is selected from the group consisting of alkyl, alkenyl, alkynyl, cycloalkyl, aryl, arylalkyl, heteroaryl, heteroarylalkyl, and heterocyclyl groups optionally substituted with at least one $R^8$.

The compounds of formula I or IA are useful as selective metabotropic glutamate receptor 1 antagonists and thus are useful in the treatment and prevention of pain (neurotropic or inflammatory), migraine, anxiety, urinary incontinence and neurodegenerative diseases such as Alzheimer's disease.

DETAILED DESCRIPTION

In one embodiment, the present invention discloses tricyclic compounds which are represented by structural formula I or IA or a pharmaceutically acceptable salt, solvate or ester thereof, wherein the various moieties are as described above.

In one embodiment, when Z is $NR^5$, $J^1$ is N, and $J^2$ and $J^3$ are C, then X, $R^1$, $R^2$, $R^3$, and $R^4$ are not all simultaneously H.

In another embodiment, when Z is NR⁵, J¹ and J² are C and J³ is N, then X, R¹, R², R³, and R⁴ are not all simultaneously H.

In another embodiment, J¹ is N, J² and J³ are CH, X is —NR⁵R⁶, R² and R³ and R⁵ are H, R⁶ is cyclopropyl, Z is S, w is 0, and R¹ is p-methoxyphenyl.

In another embodiment, Z is S, J¹ is N, and J² and J³ are each C.

In another embodiment, Z is S, J¹ and J² are N, and J³ is C.
In another embodiment, Z is S, J¹ and J³ are N, and J² is C.
In another embodiment, Z is S, J² is N, and J¹ and J³ are C.
In another embodiment, Z is S, J¹ is C, and J² and J³ are N.
In another embodiment, Z is S, J¹ and J² are C, and J³ is N.

In another embodiment, X is —NR⁵R⁶, R⁵ and R⁶ are independently selected from the group consisting of hydrogen, and alkyl and cycloalkyl groups optionally substituted with at least one R⁸.

In another embodiment, X is —NR⁵R⁶, wherein R⁵ and R⁶ are each alkyl.

In another embodiment, X is —NR⁵R⁶, wherein R⁵ is H and R⁶ is alkyl which is optionally substituted with at least one substituent selected from the group consisting of —OH, alkoxy, —CF₃, and —C≡CH.

In another embodiment, X is —NR⁵R⁶, wherein R⁵ is H and R⁶ is hydroxyalkyl.

In another embodiment, X is —NR⁵R⁶, wherein at least one of R⁵ and R⁶ is cycloalkyl.

In another embodiment, X is —NR⁵R⁶, wherein R⁵ is H and R⁶ is cyclopropyl.

In another embodiment, X is —OR⁷.

In another embodiment, X is —OR⁷, wherein R⁷ is H or alkyl.

In another embodiment, in formula I, R² and R³ are H.
In another embodiment, in formula I, R¹ and R² are H.

In another embodiment, in formula I, R¹ is selected from the group consisting of cycloalkyl, and aryl, each of which is optionally substituted with at least one R⁸, or wherein said R¹ aryl may optionally contain two radicals on adjacent carbon atoms, which radicals are taken together with the carbon atoms to which they are attached to form a five to six membered heterocyclyl or heteroaryl ring, which is optionally substituted with at least one R⁸.

In another embodiment, in formula I, R¹ is selected from the group consisting of cycloalkyl, and aryl, each of which is optionally substituted with at least one R⁸, or wherein said R¹ aryl may optionally contain two radicals on adjacent carbon atoms, which radicals are taken together with the carbon atoms to which they are attached to form a five to six membered heterocyclyl or heteroaryl ring, which is optionally substituted with at least one R⁸, wherein said R⁸ is selected from the group consisting of alkyl, cycloalkyl, cyano, alkoxy, halo, and hydroxy.

In another embodiment, in formula I, R¹ is selected from the group consisting of cycloalkyl, and aryl, each of which is optionally substituted with at least one R⁸, or wherein said R¹ aryl may optionally contain two radicals on adjacent carbon atoms, which radicals are taken together with the carbon atoms to which they are attached to form a five to six membered heterocyclyl or heteroaryl ring, which is optionally substituted with at least one R⁸, wherein said R¹ aryl, including R¹ aryl containing two radicals on adjacent carbon atoms which are taken together with the carbon atoms to which they are attached to form a five to six membered heterocyclic or heteroaryl ring, is selected from the group consisting of phenyl,

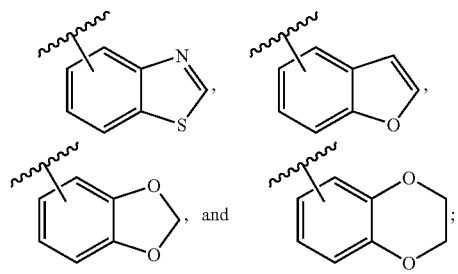

each of which is optionally substituted with at least one R⁸.

In another embodiment, in formula I or IA, R¹ is p-methoxyphenyl.

In another embodiment, in formula I or IA, R¹ is p-methoxyphenyl.

In another embodiment, the present invention discloses tricyclic compounds which are represented by structural formulae II-VII or a pharmaceutically acceptable salt, solvate or ester thereof, wherein the various moieties are as described above:

Formula II

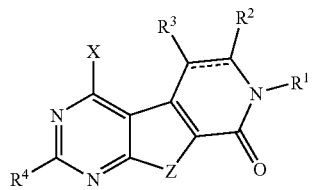

Formula III

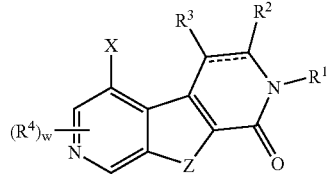

Formula IV

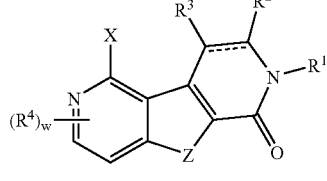

Formula V

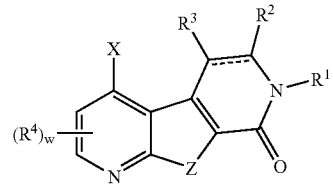

Formula VI

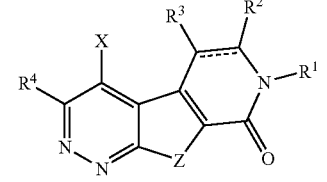

-continued

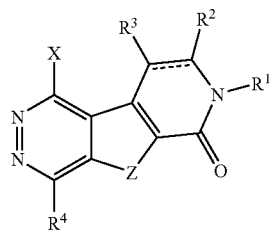
Formula VII

In another embodiment, the present invention discloses tricyclic compounds which are represented by structural formulae II-VI or a pharmaceutically acceptable salt, solvate or ester thereof, wherein the various moieties are as described above:

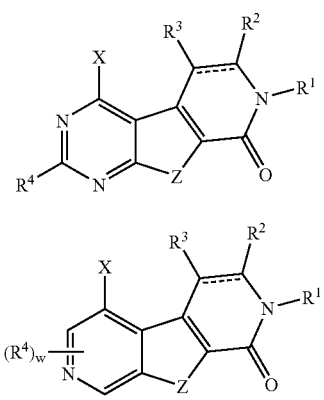
Formula II

Formula III

Formula IV

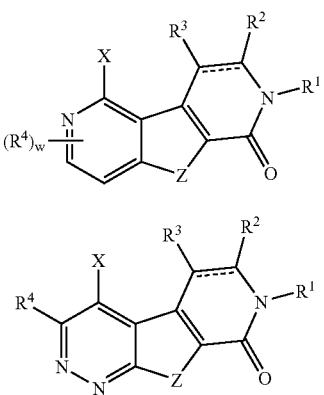
Formula V

Formula VI

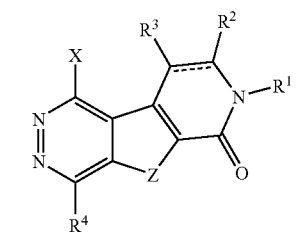

In one embodiment, with respect to Formula II, when Z is $NR^5$ then X, $R^1$, $R^2$, $R^3$, $R^4$, and $R^5$ are not all simultaneously H.

A list of representative compounds of the present invention is shown in Table 1 below.

TABLE I

| Cpd | Structure |
|---|---|
| 9A | 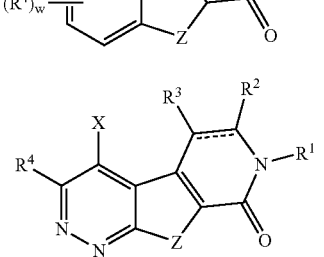 |
| 9B | 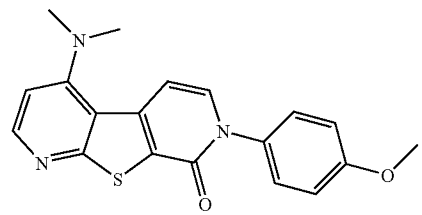 |
| 9C | 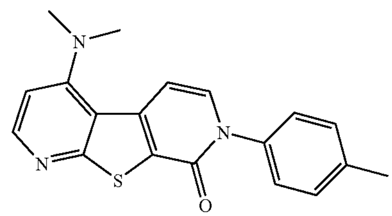 |
| 9D | 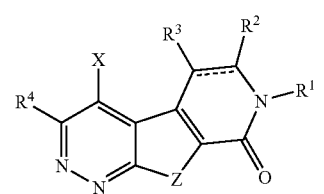 |
| 9E | 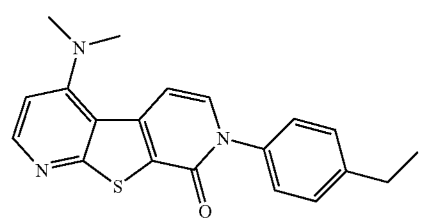 |
| 9F | 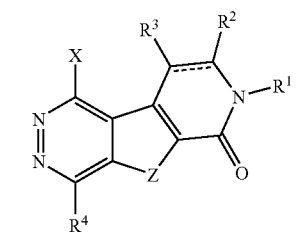 |
| 9G | 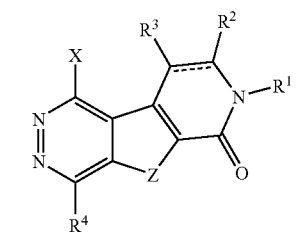 |

TABLE I-continued

| Cpd | Structure |
|---|---|
| 9H | (structure) |
| 16A | (structure) |
| 16B | (structure) |
| 16C | (structure) |
| 16D | (structure) |
| 16E | (structure) |
| 16F | (structure) |
| 16G | (structure) |
| 16H | (structure) |
| 16I | (structure) |
| 16J | (structure) |
| 16K | (structure) |
| 16L | (structure) |
| 16M | (structure) |

TABLE I-continued

| Cpd | Structure |
|-----|-----------|
| 16N | 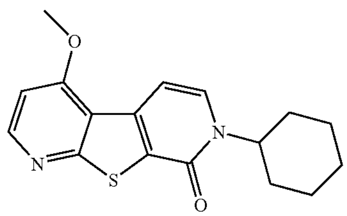 |
| 16O | 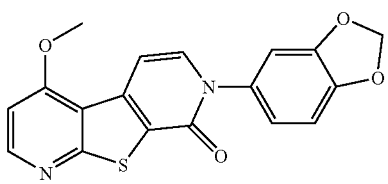 |
| 16P | 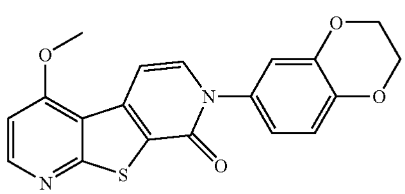 |
| 16Q | 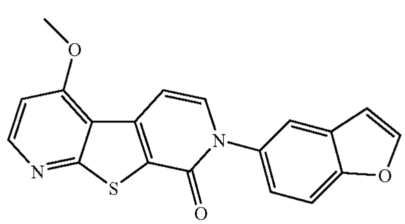 |
| 16R | 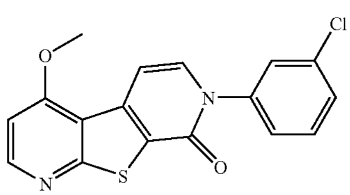 |
| 16S | 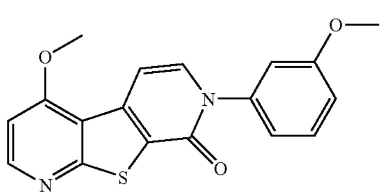 |
| 16T | 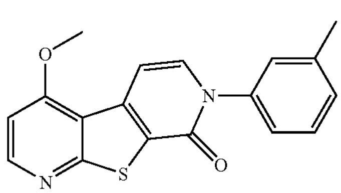 |
| 16U | 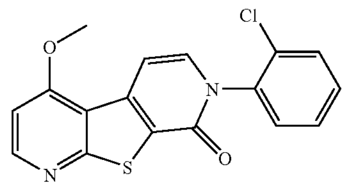 |
| 16V | 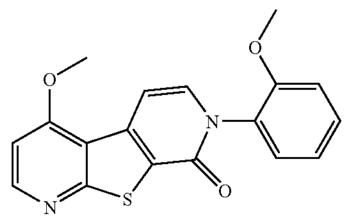 |
| 16W | 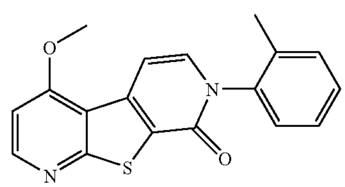 |
| 16X | 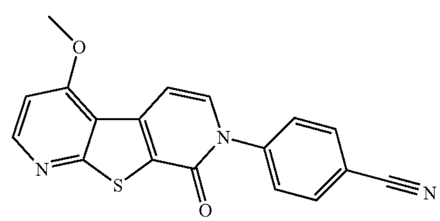 |
| 17A | 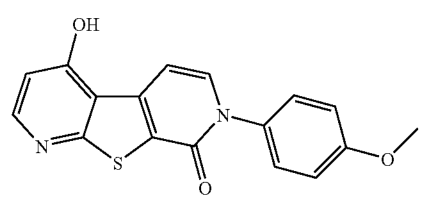 |
| 17B | 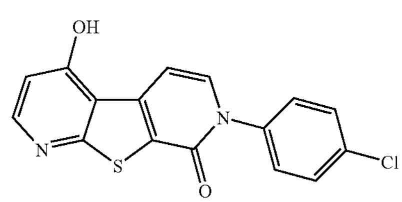 |
| 17C | 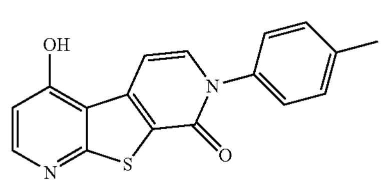 |

TABLE I-continued

| Cpd | Structure |
|---|---|
| 19A | 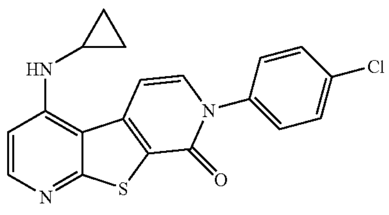 |
| 19B | 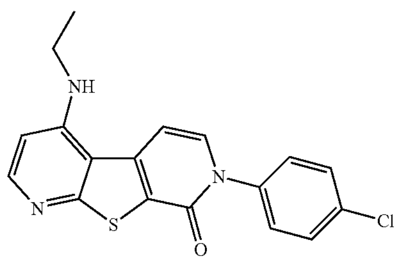 |
| 19C | 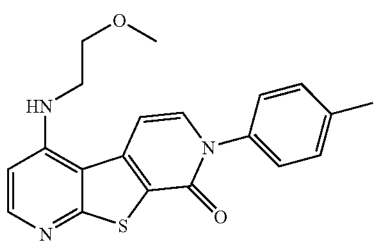 |
| 19D | 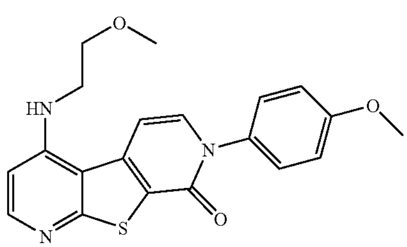 |
| 19E | 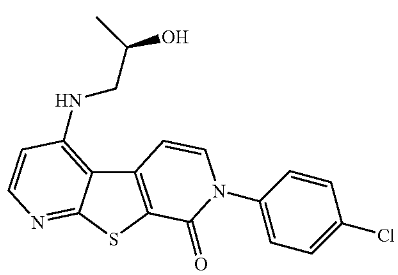 |
| 19F | 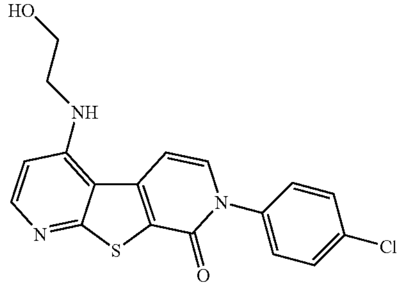 |
| 19G | 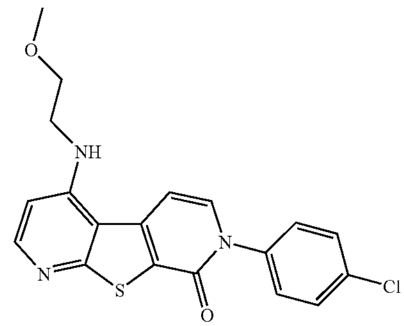 |
| 19H | 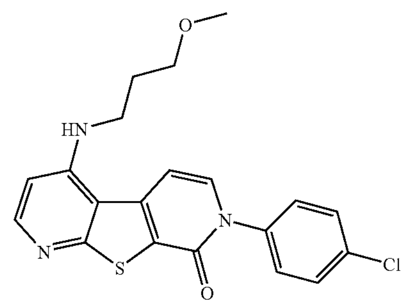 |
| 19I | 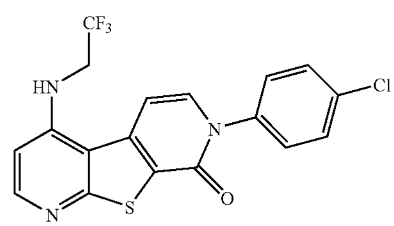 |
| 19J | 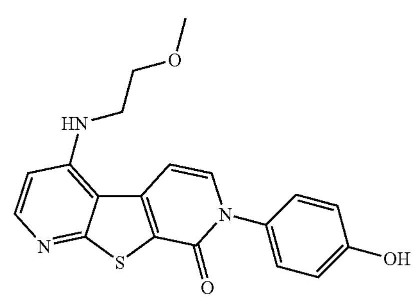 |
| 19K | 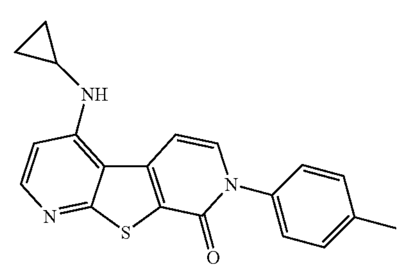 |

TABLE I-continued
| Cpd | Structure |
|---|---|
| 19L | 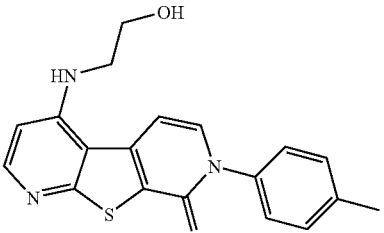 |
| 19M | 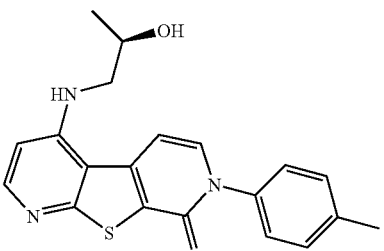 |
| 19N | 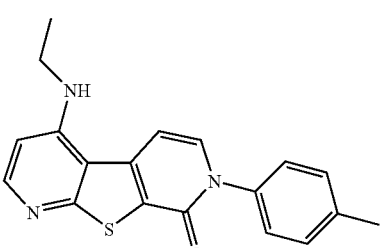 |
| 19O | 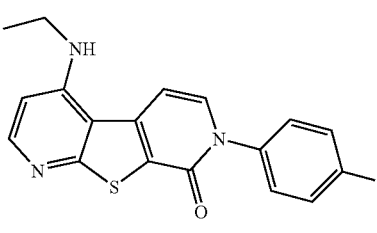 |
| 19P | 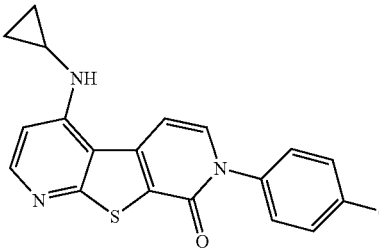 |
| 19Q | 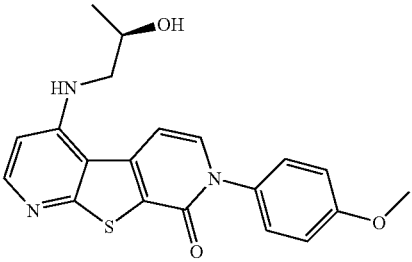 |
| 19R | 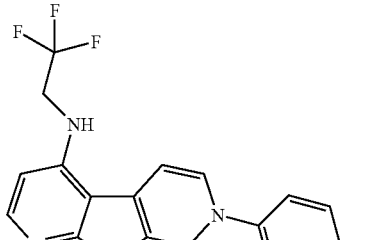 |
| 19S | 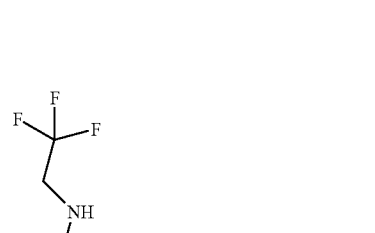 |
| 19T | 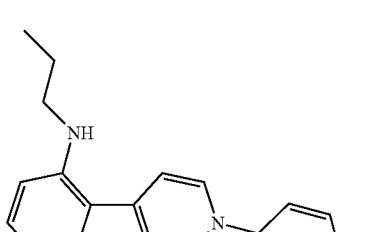 |
| 19U | 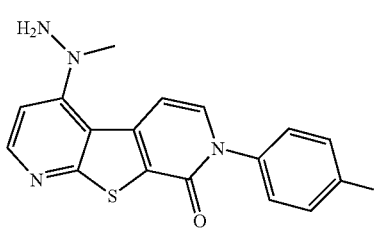 |
| 19V | 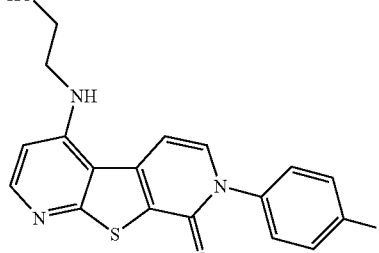 |

TABLE I-continued
| Cpd | Structure |
|---|---|
| 19W | 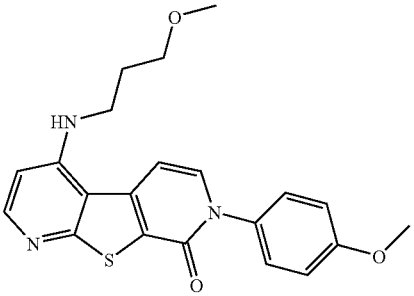 |
| 19X | 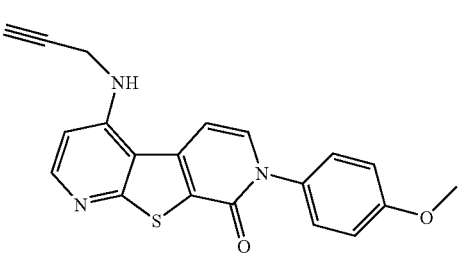 |
| 19Y | 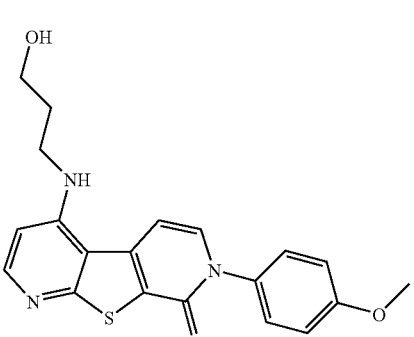 |
| 19Z | 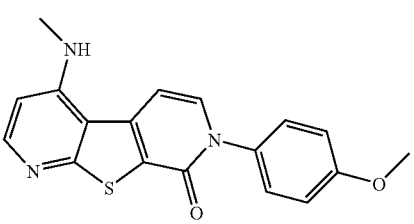 |
| 19AA | 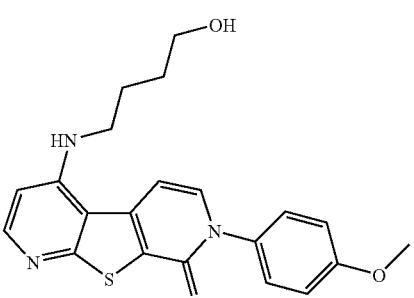 |
| 19AB | 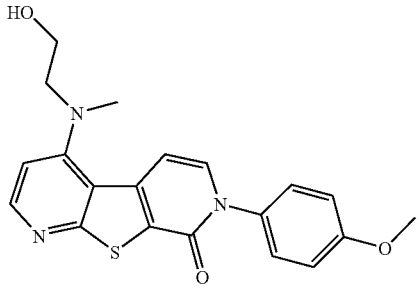 |
| 19AC | 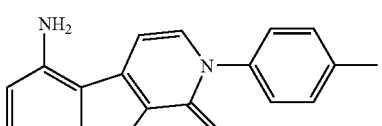 |
| 19AD | 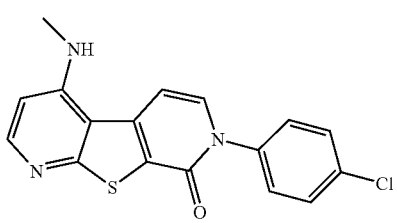 |
| 19AE | 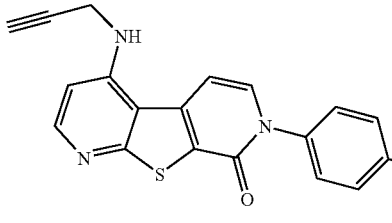 |
| 19AF | 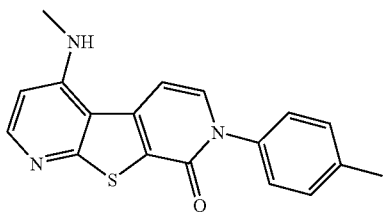 |
| 19AG | 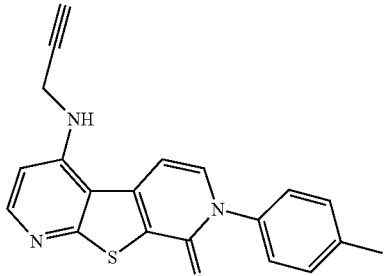 |

TABLE I-continued
| Cpd | Structure |
|---|---|
| 19AH | 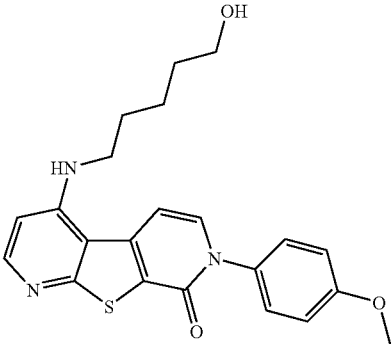 |
| 19AI | 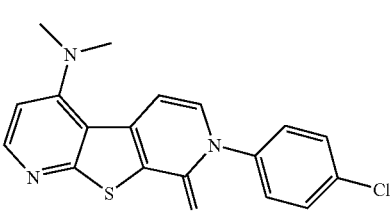 |
| 19AJ | 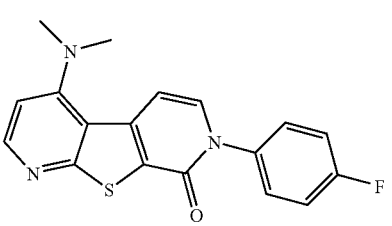 |
| 19AK | 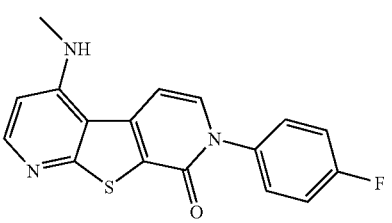 |
| 19AL | 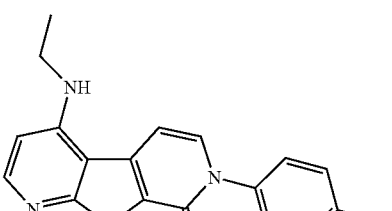 |
| 19AM | 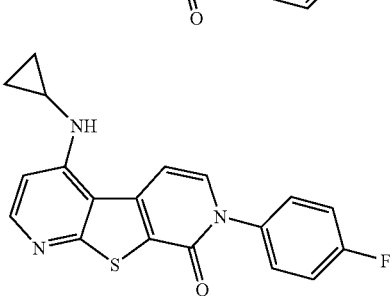 |
TABLE I-continued
| Cpd | Structure |
|---|---|
| 19AN | 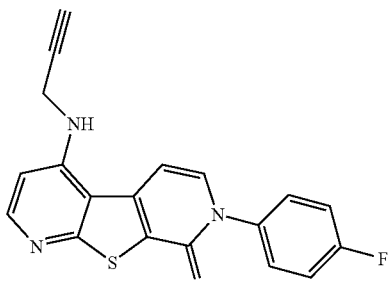 |
| 19AO | 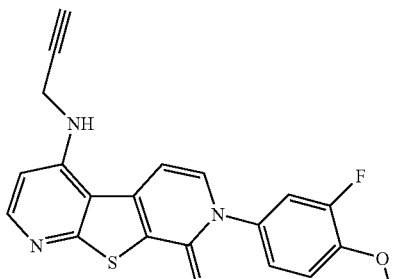 |
| 19AP | 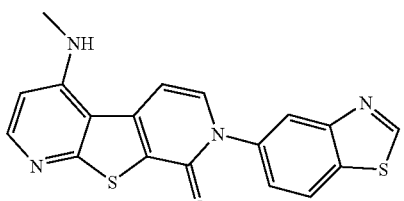 |
| 19AQ | 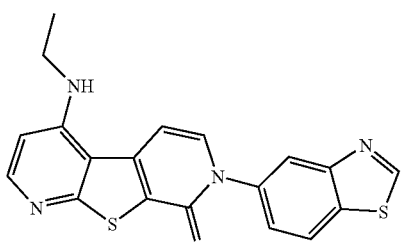 |
| 19AR | 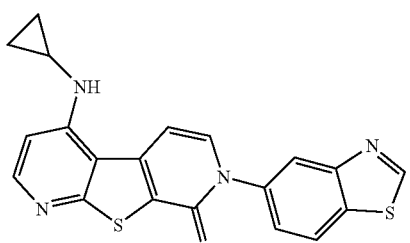 |
| 19AS | 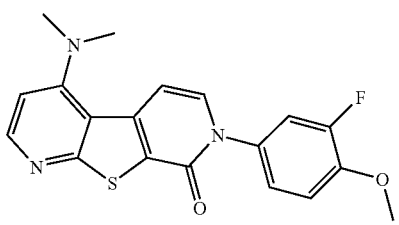 |

TABLE I-continued
| Cpd | Structure |
|---|---|
| 19AT | 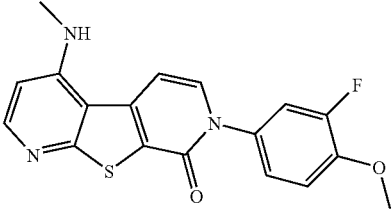 |
| 19AU | 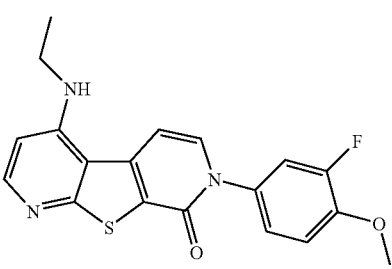 |
| 19AV | 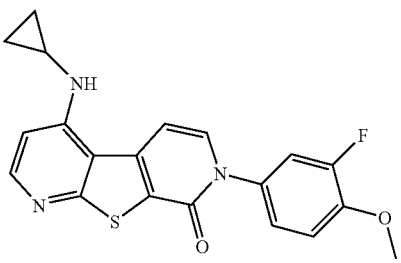 |
| 19AW | 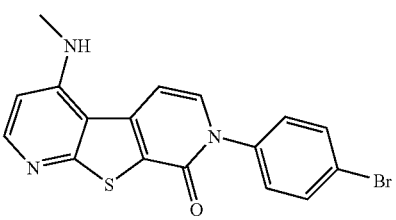 |
| 19AX | 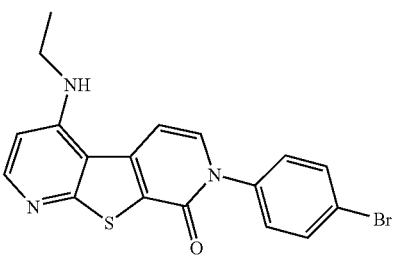 |
| 19AY | 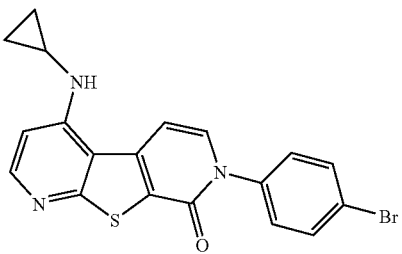 |
| 19AZ | 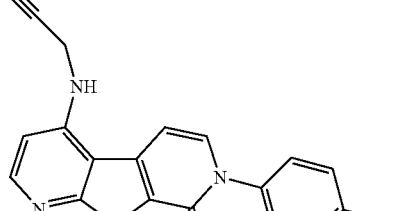 |
| 19BA | 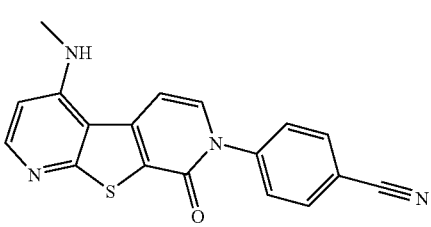 |
| 19BB | 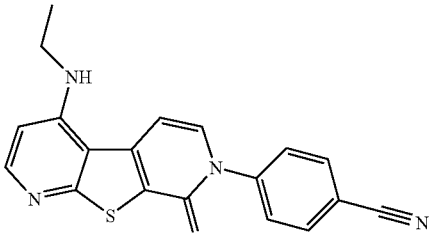 |
| 19BC | 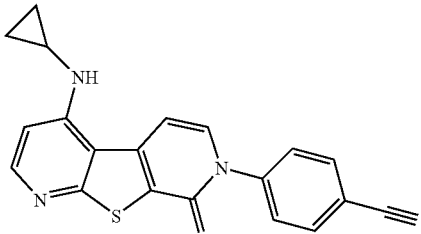 |
| 19BD | 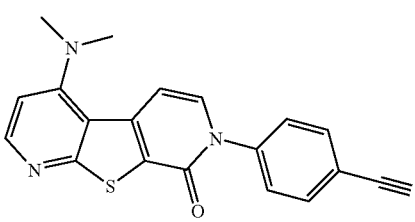 |
| 19BE | 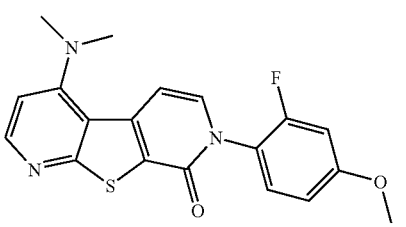 |

TABLE I-continued

| Cpd | Structure |
|---|---|
| 19BF | (structure) |
| 19BG | (structure) |
| 19BH | (structure) |
| 23A | (structure) |
| 23B | (structure) |
| 23C | (structure) |
| 26A | (structure) |
| 26B | (structure) |
| 26C | (structure) |
| 26D | (structure) |
| 26E | (structure) |
| 26F | (structure) |

TABLE I-continued

| Cpd | Structure |
|---|---|
| 26G | (structure) |
| 26H | (structure) |

Pharmaceutically acceptable salts, solvates or esters of the compounds of Table 1 are also contemplated.

In another embodiment, the compounds are selected from the group consisting of 9A-G, 16A-C, 16E, 19A-B, 19K, 19O-P, 19AS, 19AV, 19Aw, 19AX, 19AY, and 19BE.

In another embodiment, the compounds are selected from the group consisting of 9C, 9G, 16B, 19AX and 19AY.

In another embodiment, the compounds are selected from the group consisting of 9B, 19O and 19P.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)₂, carboxy, —C(O)O-alkyl and —S(alkyl). Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl, aryl and cycloalkyl.

"Alkylene" means a difunctional group obtained by removal of a hydrogen atom from an alkyl group that is defined above. Non-limiting examples of alkylene include methylene, ethylene and propylene.

"Aryl" (sometimes abbreviated "ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. "Cycloalkyl" includes "arylcycloalkyl" and "cycloalkylaryl" as defined below.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above.

"cyanoalkyl" means an alkyl as defined above wherein one or more hydrogen atoms on the alkyl is replaced by a cyano group.

"oxo" means (=O) and "thioxo" means (=S).

"Ring system substituent" means a substituent attached to an aromatic or non-aromatic ring system which, for example, replaces an available hydrogen on the ring system. Ring system substituents may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N—$, $Y_1Y_2N$-alkyl-, $Y_1Y_2NC(O)—$ and $Y_1Y_2NSO_2—$, wherein $Y_1$ and $Y_2$ may be the same or different and are independently selected from the group consisting of hydrogen, alkyl, aryl, and aralkyl.

"Ring system substituent" may also mean a single moiety which simultaneously replaces two available hydrogens on two adjacent carbon atoms (one H on each carbon) on a ring system. Examples of such moiety are oxy, methylene dioxy, ethylenedioxy, —C(CH$_3$)$_2$— and the like which form moieties such as, for example:

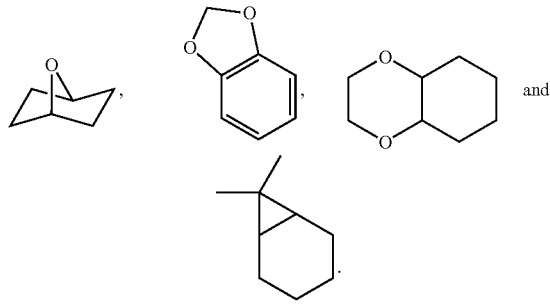

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl. "Cycloalkenyl" includes "arylcycloalkenyl" and "cycloalkenylaryl" as defined below.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. A non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. "Heterocyclyl" includes "heteroarylcycloalkyl" and "cycloalkylheteroaryl" as defined below.

"Arylcycloalkenyl" means a group derived from a fused aryl and cycloalkenyl as defined herein by removal of a hydrogen atom from the cycloalkenyl portion. Preferred arylcycloalkenyls are those wherein aryl is phenyl and the cycloalkenyl consists of about 5 to about 6 ring atoms. The arylcycloalkenyl can be optionally substituted by one or more ring system substituents, wherein "ring system substituent" is as defined above. Non-limiting examples of suitable arylcycloalkenyls include 1,2-dihydronaphthalene, indene, and the like. The bond to the parent moiety is through a non-aromatic carbon atom.

"Cycloalkenylaryl" means a group derived from a fused arylcycloalkenyl as defined herein by removal of hydrogen atom from the aryl portion. Non-limiting examples of suitable cycloalkenylaryls are as described herein for a arylcycloalkenyl, except that the bond to the parent moiety is through an aromatic carbon atom.

"Arylcycloalkyl" means a group derived from a fused aryl and cycloalkyl as defined herein by removal of a hydrogen atom from the cycloalkyl portion. Preferred arylcycloalkyls are those wherein aryl is phenyl and the cycloalkyl consists of about 5 to about 6 ring atoms. The arylcycloalkyl can be optionally substituted by one or more ring system substituents, wherein "ring system substituent" is as defined above. Non-limiting examples of suitable arylcycloalkyls include 1,2,3,4-tetrahydronaphthyl, and the like. The bond to the parent moiety is through a non-aromatic carbon atom.

"Cycloalkylaryl" means a group derived from a fused arylcycloalkyl as defined herein by removal of a hydrogen atom from the aryl portion. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl as defined herein by removal of a hydrogen atom from the cycloalkyl portion. Preferred heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The heteroarylcycloalkyl can be optionally substituted by one or more ring system substituents, wherein "ring system substituent" is as defined above. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like. The bond to the parent moiety is through a non-aromatic carbon atom.

"Cycloalkylheteroaryl" means a group derived from a fused heteroarylcycloalkyl as defined herein by removal of a hydrogen atom from the heteroaryl portion. Non-limiting examples of suitable cycloalkylheteroaryls are as described herein for heteroarylcycloalkyl, except that the bond to the parent moiety is through an aromatic carbon atom.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkynyl" means an aryl-alkynyl- group in which the aryl and alkynyl are as previously described. Preferred aralkynyls contain a lower alkynyl group. The bond to the parent moiety is through the alkynyl. Non-limiting examples of suitable aralkynyl groups include phenacetylenyl and naphthylacetylenyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Heteroaralkynyl" means an heteroaryl-alkynyl- group in which the heteroaryl and alkynyl are as previously described. Preferred heteroaralkynyls contain a lower alkynyl group. Non-limiting examples of suitable heteroaralkynyl groups include pyrid-3-ylacetylenyl and quinolin-3-ylacetylenyl. The bond to the parent moiety is through the alkynyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Heteroaroyl" means a heteroaryl-C(O)— group in which the heteroaryl group is as previously described. Non-limiting examples of suitable groups include nicotinoyl and pyrrol-2-ylcarbonyl. The bond to the parent moiety is through the carbonyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups are as previously described. Non-limiting examples of suitable aralkyloxy groups include benzyloxy and 1- or 2-naphthalenemethoxy. The bond to the parent moiety is through the ether oxygen.

"Alkylamino" means an —$NH_2$ or —$NH_3^+$ group in which one or more of the hydrogen atoms on the nitrogen is replaced by an alkyl group as defined above.

"Arylamino" means an —$NH_2$ or —$NH_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. A non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O$_2$)— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from a combination of the specified ingredients in the specified amounts.

Lines drawn into the ring systems, such as, for example:

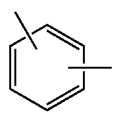

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

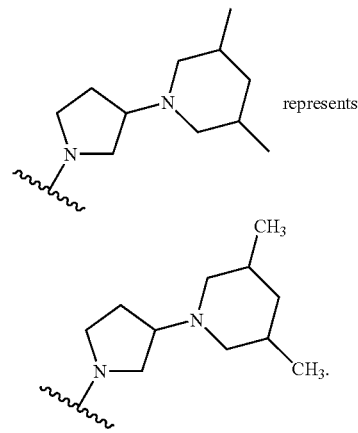

It should also be noted that any carbon or heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

"Effective amount" or "therapeutically effective amount" is meant to describe an amount of a compound or a composition of the present invention effective in antagonizing mGluRs, in particular mGluR1, and thus producing the desired therapeutic, ameliorative, inhibitory or preventative effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al., *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, gluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the present compounds.

Polymorphic forms of the compounds of formula I, and of the salts, solvates and prodrugs of the compounds of formula I, are intended to be included in the present invention.

The compounds according to the invention have pharmacological properties; in particular, the compounds of formula I can be mGluR (metabotropic glutamate receptor) antagonists, more particularly, selective mGluR1 antagonists. Accordingly, the present compounds are useful in the treatment or prevention of conditions that are treatable or preventable by inhibiting mGluR, more particularly, mGluR1 function. Such conditions include a variety of acute and chronic neurological disorders associated with excessive or inappropriate stimulation of excitatory amino acid transmission as well as conditions which lead to glutamate-deficient functions.

Examples of treatable or preventable acute neurological disorders include, but are not limited to, cerebral deficits subsequent to cardiac bypass surgery and grafting, cerebral ischemia, stroke (ischemic or hemorrhagic), spinal cord injuries (due to trauma, infarction/ischemia or inflammation), head trauma, perinatal hypoxia, cardiac arrest and hypoglycemic neuronal damage. Examples of treatable or preventable chronic neurological disorders include, but are not limited to, Alzheimer's disease, Huntington's Chorea, amyotrophic lateral sclerosis (ALS), AIDS-induced dementia, inherited ataxias, ocular damage and retinopathy, cognitive disorders, and idiopathic and drug-induced Parkinson's. Other conditions associated with glutamate dysfunctions treatable or preventable by compounds of formula I include, but are not limited to, muscle spasms, convulsions (e.g., epilepsy), spasticity, migraine (including menstrual migraine), psychoses (e.g., schizophrenia and bipolar disorder), urinary incontinence, anxiety and related disorders (e.g. panic attack), emesis, brain edema, tardive dyskinesia, depression, drug tolerance and withdrawal (e.g., opiates, benzodiazepines, nicotine, cocaine, or ethanol), and smoking cessation.

The compounds of formula I are also useful for treating or preventing pain which may be neuropathic (nerve damage) or inflammatory (tissue damage). These compounds are particularly useful for treating or preventing neuropathic pain. Neuropathic pain used herein refers to an abnormal state of pain sensation, in which a reduction of pain threshold and the like are continued, due to functional abnormalities accompanying damage or degeneration of a nerve, plexus or perineural soft tissue, which is caused by wound, compression, infection, cancer, ischemia and the like, or metabolic disorders such as diabetes mellitus and the like. Neuropathic pain includes pain caused by either central or peripheral nerve damage. It also includes the pain caused by either mononeuropathy or polyneuropathy. In some embodiments, the neuropathic pain is induced by diabetes. In other embodiments, the neuropathic pain is induced by compression of nerves.

Examples of neuropathic pain treatable or preventable by the present compounds include, but are not limited to, allodynia (a pain sensation induced by mechanical or thermal stimulus that does not normally provoke pain), hyperalgesia (an excessive response to a stimulus that is normally painful), hyperesthesia (an excessive response to a contact stimulus), diabetic polyneuropathy, entrapment neuropathy, cancer pain, central pain, labor pain, myocardial infarction pain, post-stroke pain, pancreatic pain, colic pain, muscle pain, post-operative pain, pain associated with intensive care, pain associated with a periodontal disease (including gingivitis and periodontitis), menstrual pain, migraine pain, persistent headaches (e.g., cluster headache or chronic tension headache), persistent pain states (e.g., fibromyalgia or myofascial pain), trigeminal neuralgia, postherpetic neuralgia, arthritic pain (e.g., pain due to osteoarthritis or rheumatoid arthritis), bursitis, pain associated with AIDS, visceral pain (e.g., interstitial cystitis and irritable bowel syndrome (IBS)), pain due to spinal trauma and/or degeneration, burn pain, referred pain, enhanced memory of pain and neuronal mechanisms involved in coping with pain. The compounds of the present invention are particularly useful for treating or preventing allodynia and hyperalgesia.

Compounds of formula I are also useful for treating or preventing pain associated with inflammation or an inflammatory disease in a patient. The pain associated with inflammation or an inflammatory disease treatable or preventable by the present compounds may arise where there is an inflammation of the body tissue which may be a local inflammatory response and/or a systemic inflammation. For example, the present compounds can be used to treat or prevent pain associated with inflammatory diseases including, but not limited to, organ transplant rejection; reoxygenation injury resulting from organ transplantation including transplantation of the heart, lung, liver, or kidney; chronic inflammatory diseases of the joints, including arthritis, rheumatoid arthritis, osteoarthritis and bone diseases associated with increased bone resorption; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection and necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer.

The present compounds can also be used for treating or preventing pain associated with an inflammatory disease that involves a systemic inflammation of the body, such as gram-positive or gram negative shock, hemorrhagic or anaphylactic shock, shock induced by cancer chemotherapy in response to pro-inflammatory cytokines (e.g., shock associated with pro-inflammatory cytokines), and shock induced by a chemotherapeutic agent that is administered as a treatment for cancer.

One aspect of this invention relates to a method of selectively antagonizing mGluR1 in a cell in need thereof, comprising contacting said cell with at least one compound of formula I or a pharmaceutically acceptable salt, solvate, or ester thereof.

The term "antagonist of metabatropic glutamate receptor (e.g., mGluR1)" refers to a compound that binds to the metabatropic glutamate receptor (e.g., mGluR1) but fails to elicit a response thereby blocking agonist action, i.e., inhibiting a function of mGluRs (e.g., mGluR1). Accordingly, mGluR (e.g., mGluR1) mediated processes and responses can be inhibited with an antagonist of mGluR (e.g., mGluR1). Preferably, an antagonist selectively antagonizes group I mGluRs. More preferably, an antagonist of the present invention is a selective antagonist of mGluR1. A selective antagonist of mGluR1 is one that antagonizes mGluR1, but antagonizes other mGluRs only weakly or substantially not at all, or at least antagonizes other mGluRs with an $IC_{50}$ at least 10 or even 100 or 1000 times greater than the $IC_{50}$ at which it antagonizes mGluR1. Most preferred antagonists are those which can selectively antagonize mGluR1 at low concentrations, for example, those that cause a level of antagonism of 50% or greater at a concentration of 100 nM or less.

Another aspect of this invention relates to a method of treating or preventing a disease or condition associated with mGluR1 in a mammal (e.g., human) in need thereof comprising administering a therapeutically effective amount of at least one compound of formula I or a pharmaceutically acceptable salt, solvate, or ester thereof to said mammal.

A preferred dosage is about 0.001 to 500 mg/kg of body weight/day of the compound of formula I. An especially preferred dosage is about 0.01 to 25 mg/kg of body weight/day of a compound of formula I or a pharmaceutically acceptable salt, solvate, or ester thereof.

The compounds of this invention may also be useful in combination (administered together or sequentially) with one or more additional therapeutic agents for the treatment of the above disorders or conditions. Such additional therapeutic agents may be a pain management agent, including non-opioid analgesics such as acetylsalicylic acid, choline magnesium trisalicylate, acetaminophen, ibuprofen, fenoprofen, diflusinal, and naproxen; and opioid analgesics, such as morphine, hydromorphone, methadone, levorphanol, fentanyl, oxycodone, and oxymorphone. Other such therapeutic agents may be a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing urinary incontinence (UI), an agent for treating Alzheimer's disease, an agent for treating or preventing inflammatory bowel disease (IBD), an agent for treating or preventing inflammatory bowel syndrome (IBS), an agent for treating Parkinson's disease and parkinsonism, an agent for treating anxiety, an agent for treating epilepsy, an agent for treating a stroke, an agent for treating psychosis, an agent for treating Huntington's chorea, an agent for treating ALS, an agent for treating vomiting, an agent for treating dyskinesia, or an agent for treating depression, and mixtures thereof.

If formulated as a fixed dose, such combination products employ the compounds of this invention within the dosage range described herein and the other pharmaceutically active agent or treatment within its dosage range. Compounds of formula I may also be administered sequentially with known therapeutic agents when a combination formulation is inappropriate. The invention is not limited in the sequence of administration; compounds of formula I may be administered either prior to or after administration of the known therapeutic agent. Such techniques are within the skills of persons skilled in the art as well as attending physicians.

Accordingly, in one aspect, this invention includes combinations comprising an amount of at least one compound of formula I or a pharmaceutically acceptable salt, solvate, or ester thereof, and an amount of one or more additional therapeutic agents listed above wherein the amounts of the compounds/treatments result in a desired therapeutic effect.

The pharmacological properties of the compounds of this invention may be confirmed by a number of pharmacological assays. The selective antagonistic activity of the present compounds towards the metabotropic glutamate receptor 1 (mGluR1) may be assayed by methods known in the art, for example, by using the methods as described in the examples.

The actions of the compounds of formula I for the treatment or prevention of pain may be assessed by various animal models, for example, by the following tests:

Formalin test: Mice are gently restrained and 30 μl of formalin solution (1.5% in saline) is injected subcutaneously into the plantar surface of the right hind paw of the mouse, using a microsyringe with a 27 gauge needle. After the formalin injection, the mouse is immediately put back into the Plexiglas observation chamber (30×20×20 cm) and the nociceptive response of the animal to formalin injection is observed for a period of 60 min. The duration of licking and flinching of the injected paw is recorded and quantified every 5 min for the total observation period. The recording of the early phase (first phase) starts immediately and lasts for 5 min. The late phase (second phase) starts about 10-15 min after formalin injection.

L5 and L6 spinal nerve ligation of the sciatic nerve (neuropathic pain model): The peripheral neuropathy is produced by ligating the L5 and L6 spinal nerves of the right sciatic nerve, according to the method previously described by Kim and Chung (1992) except for small changes. Briefly, rats are anaesthetized with chloral hydrate (400 mg/kg, i.p.), placed in a prone position and the right paraspinal muscles separated from the spinous processes at the L4-S2 levels. The L5 transverse process is carefully removed with a small rongeur to identify the L4-L5 spinal nerves. The right L5 and L6 spinal nerves are isolated and tightly ligated with 7/0 silk thread. A complete hemostasis is confirmed and the wound sutured.

Chronic constriction injury (CCI) of the sciatic nerve (neuropathic pain model): Surgery is performed according to the method described by Bennett & Xie (1987). Rats are anaesthetized with chloral hydrate (400 mg/kg, i.p.) and the common sciatic nerve is exposed at the level of the mid-thigh. Proximally, at about 1 cm from the nerve trifurcation, four loose ligatures (4/0 silk) spaced 1 mm are tied around the nerve. The ligature delays, but does not arrest, circulation through the superficial epineural vasculature. The same procedure is performed except for ligature placement (sham surgery) in a second group of animals.

Carrageenan (inflammatory pain model): The right hind paw of each animal is injected at subplantar level with 0.1 mL of carrageenan (25 GA needle). Pre-tests are determined prior to carrageenan or drug administration. In POST-TREATMENT protocol, rats are tested 3 hours after carrageenan treatment to establish the presence of hyperalgesia and then at different times after drug administration. In PRE-TREATMENT protocol, one hour after drug administration, rats are treated with carrageenan and they are tested starting from 3 hours later.

Freund's adjuvant-induced arthritic model (inflammatory pain model): Animals receive a single subplantar injection of 100 mL of a 500 mg dose of heat-killed and dried *Mycobacterium tuberculosis* (H37 Ra, Difco Laboratories, Detroit, Mich., USA) in a mixture of paraffin oil and an emulsifying agent, mannide monooleate (complete Freund's adjuvant). Control animals are injected with 0.1 mL mineral oil (incomplete Freund's adjuvant).

Measurement of tactile allodynia (behavioural test): Behavioral tests are conducted by observer blinded to the treatment during the light cycle to avoid circadian rhythm fluctuation. Tactile sensitivity is evaluated using a series of calibrated Semmes-Weinstein (Stoelting, Ill.) von Frey filaments, bending force ranging from 0.25 to 15 g. Rats are placed in a transparent plastic box endowed with a metal mesh floor and are habituated to this environment before experiment initiation. The von Frey filaments are applied perpendicularly to the midplantar surface of the ipsilateral hind paws and the mechanical allodynia is determined by sequentially increasing and decreasing the stimulus strength ("up-down" paradigm of the filament presentation). Data are analysed with a Dixon non-parametric test (Chaplan et al. 1994). Paw licking or vigorously shaking after stimulation is considered pain-like responses.

Thermal hyperalgesia (behavioural test): Thermal hyperalgesia to radiant heat is assessed by measuring the withdrawal latency as an index of thermal nociception (Hargreaves et al., 1998). The plantar test (Basile, Comerio, Italy) is chosen because of its sensitivity to hyperalgesia. Briefly, the test consists of a movable infrared source placed below a glass plane onto which the rat is placed. Three individual perspex boxes allow three rats to be tested simultaneously. The infrared source is placed directly below the plantar surface of the hind paw and the paw withdrawal latency (PWL) is defined as the time taken by the rat to remove its hind paw from the heat source. PWLs are taken three times for both hind paws of each rat and the mean value for each paw represented the thermal pain threshold of rat. The radiant heat source is adjusted to result in baseline latencies of 10-12 sec. The instrument cut-off is fixed at 21 sec to prevent tissue damage.

Weight bearing (behavioural test): An incapacitance tester is employed for determination of hind paw weight distribution. Rats are placed in an angled plexiglass chamber positioned so that each hind paw rested on a separate force plate. The weight bearing test represents a direct measure of the pathological condition of the arthritic rats without applying any stress or stimulus, thus this test measures a spontaneous pain behaviour of the animals.

While it is possible for the active ingredient to be administered alone, it is preferable to present it as a pharmaceutical composition. The compositions of the present invention comprise at least one active ingredient, as defined above, together with one or more acceptable carriers, adjuvants or vehicles thereof and optionally other therapeutic agents. Each carrier, adjuvant or vehicle must be acceptable in the sense of being compatible with the other ingredients of the composition and not injurious to the mammal in need of treatment.

Accordingly, this invention also relates to pharmaceutical compositions comprising at least one compound of formula I, or a pharmaceutically acceptable salt, solvate or ester thereof and at least one pharmaceutically acceptable carrier, adjuvant or vehicle.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts, solvates or esters thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of formula I or a pharmaceutically acceptable salt, solvate, or ester thereof and at least one pharmaceutically acceptable carrier, adjuvant or vehicle.

Yet another aspect of this invention is a kit comprising an amount of at least one compound of formula I or a pharmaceutically acceptable salt, solvate or ester thereof and an amount of at least one additional therapeutic agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

EXAMPLES

In general, the compounds of this invention may be prepared from known or readily prepared starting materials, following methods known to one skilled in the art and those illustrated below. All stereoisomers and tautomeric forms of the compounds are contemplated.

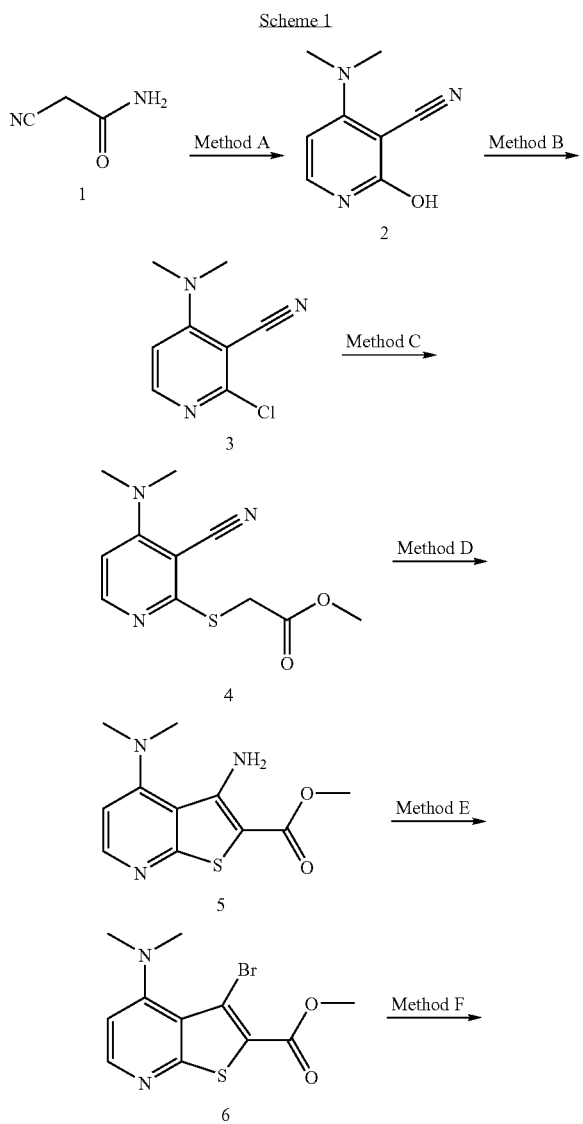

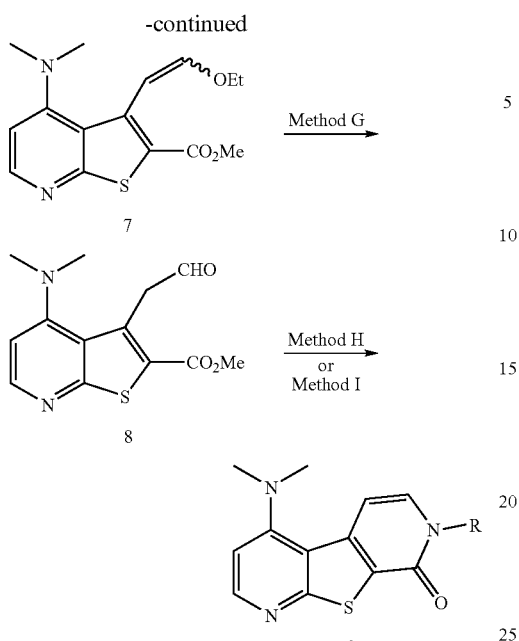
Scheme 2
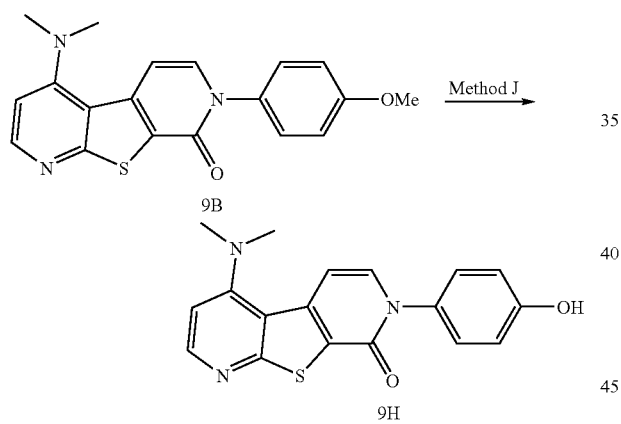
Scheme 3
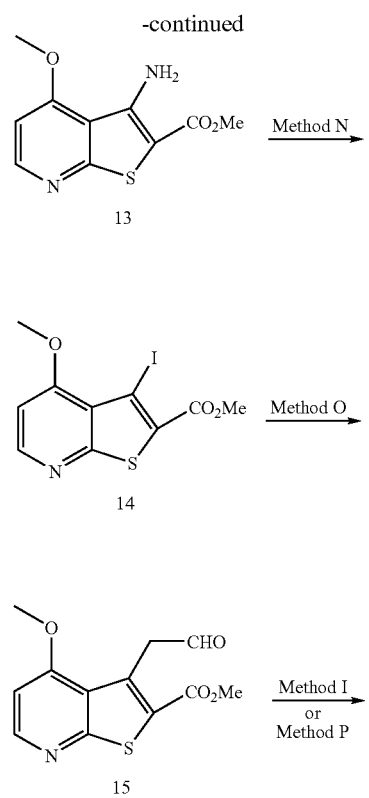
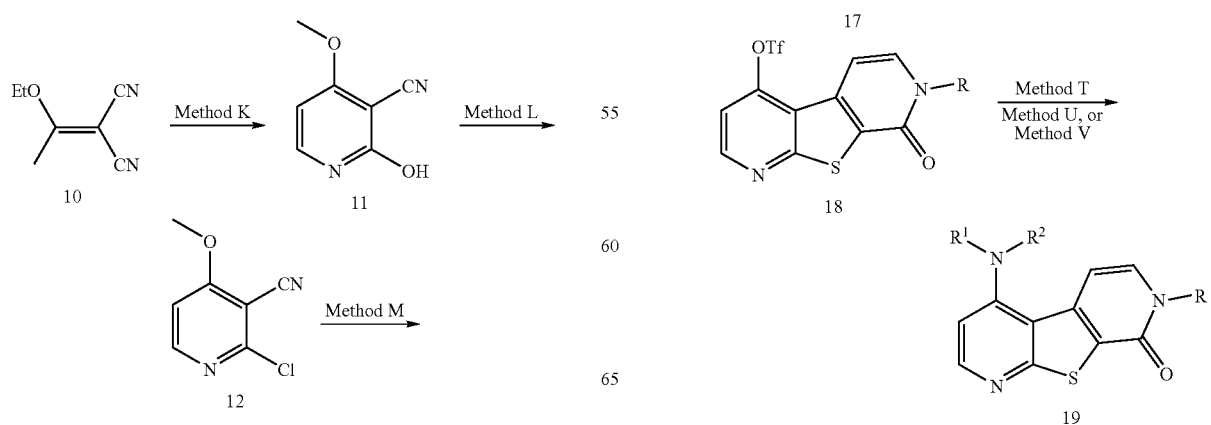

Scheme 4
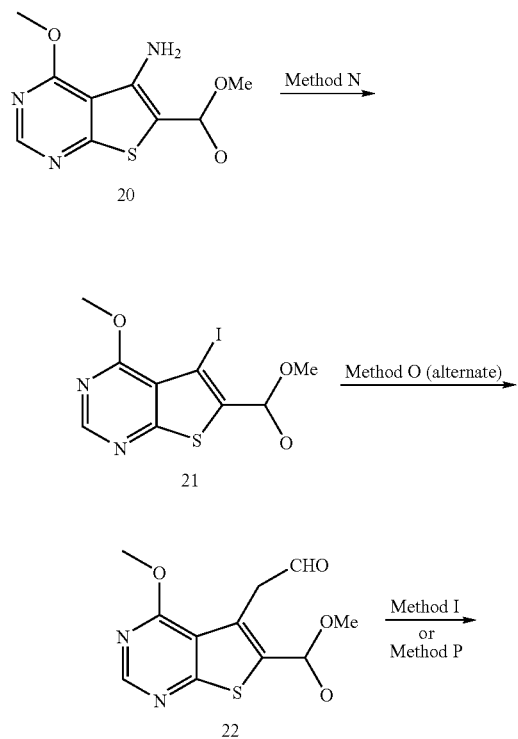
Scheme 5
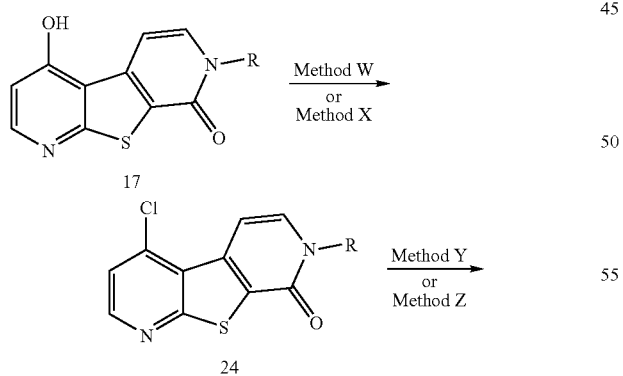
Scheme 6
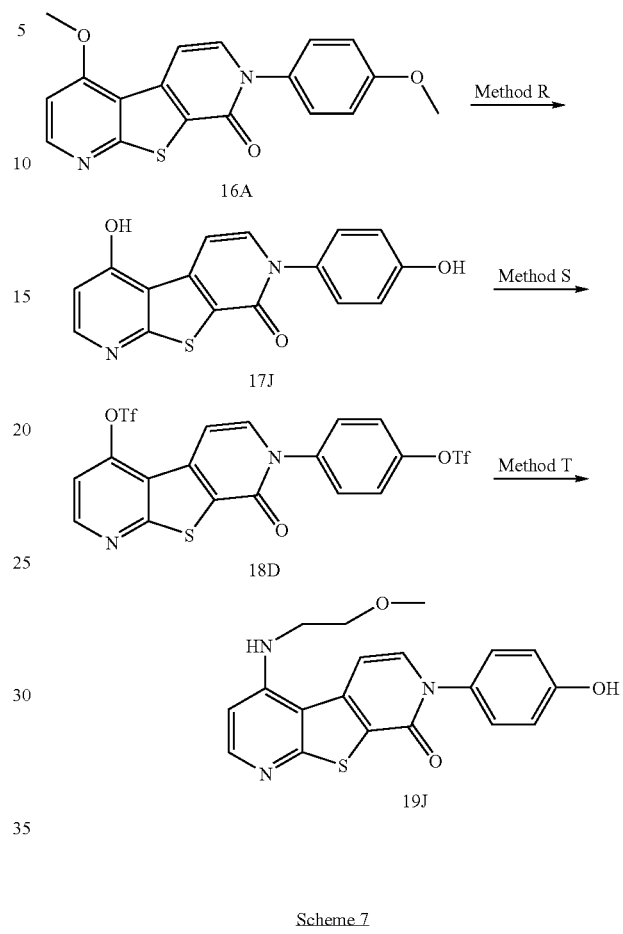
Scheme 7
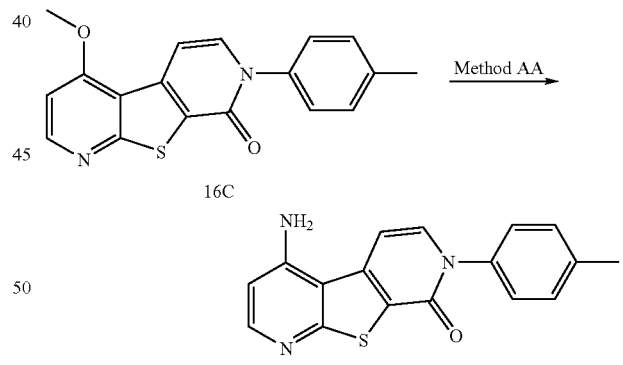
Scheme 8
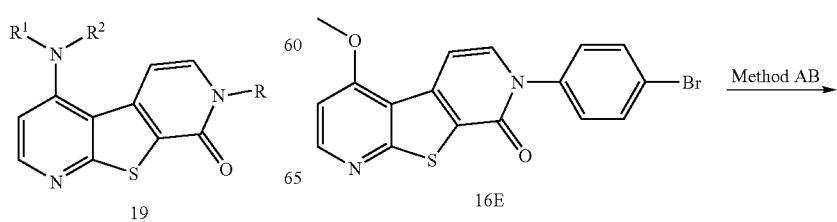

-continued

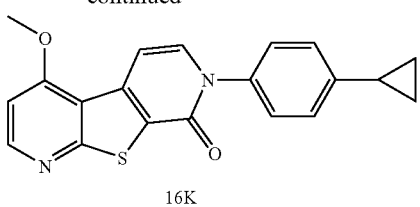

16K

Scheme 9

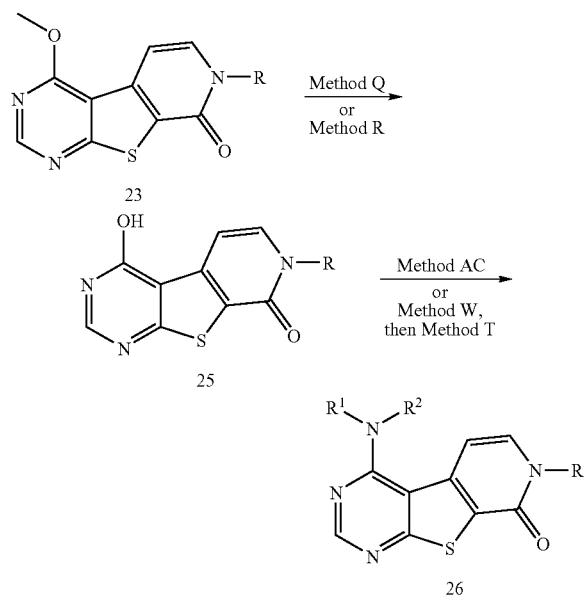

Scheme 10

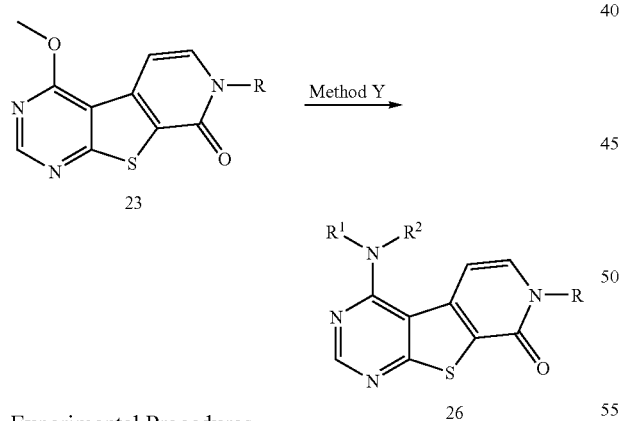

Experimental Procedures

Method A:

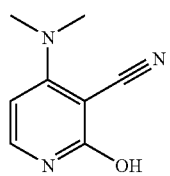

2

(Ref: H. Zipse and L.-H. Wang, *Liebigs Ann.* 1996, 1501-1509.) A mixture of cyanoacetamide (8.4 g, 0.1 mol) and dimethylacetamide dimethylacetal (14.6 mL, 0.1 mol) was heated under reflux in dry ethanol (150 mL) for 2.5 hours under a nitrogen atmosphere. The resulting white crystals of 2-cyano-3-(dimethylamino)-2-butenamide (10.0 g, 0.068 mol) were filtered, washed with ethanol and dried under vacuum. To this was added N,N-dimethyl-formamide dimethylacetal (8.1 g, 0.068 mol) and the mixture heated under reflux in dry toluene (100 mL) for 1 hour before evaporating the solvent under reduced pressure. The residue was heated neat at 150° C. for 30 min, cooled, washed twice with acetone and dried under vacuum to give compound 2. $^1$H NMR (DMSO-$d_6$) δ 7.22 (d, 1H), 5.86 (d, 1H), 3.13 (s, 6H); Mass Spectrum (M+1)$^+$: m/z calcd. for $C_8H_{10}N_3O^+$=164.1, found m/z=164.2.

Method B:

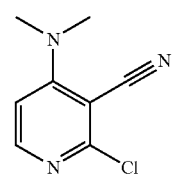

3

(Ref.: M. Yu. Yakovlev, O. B. Romanova, S. I. Grizik, A. V. Kadushkin, and V. G. Granik, *Khimiko-Farmatsevticheskii Zhurmal,* 1997, 31(11), 44-47.) To compound 2 (9.34 g, 0.057 mol) was added phosphorous oxychloride (95 mL, 1.02 mol) and to the mixture was added triethylamine (4 ml, 0.029 mol) dropwise. The resultant mixture was heated at reflux for a period of 3 hours, cooled to room temperature and quenched with ice-water. The mixture was then basified using 40% sodium hydroxide solution and the resulting precipitate filtered, washed with water until neutral and dried in a vacuum oven to give chloropyridine compound 3. $^1$H NMR (CDCl$_3$): δ 7.95 (d, 1H), 6.48 (d, 1H), 3.20 (s, 6H).

Method C:

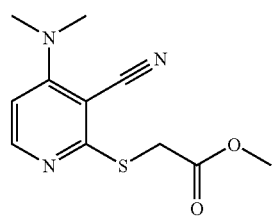

4

(Ref.: M. Yu. Yakovlev, O. B. Romanova, S. I. Grizik, A. V. Kadushkin, and V. G. Granik, *Khimiko-Farmatsevticheskii Zhurmal,* 1997, 31(11), 44-47.) A solution of compound 3 (6.02 g, 0.033 mol), methyl thioglycolate (7.05 g, 0.066 mol) and potassium carbonate (6.88 g, 0.050 mol) in DMF (50 mL) was stirred for a period of 5 hours at room temperature under a nitrogen atmosphere. Water (200 mL) was added, and the resulting precipitate filtered and dried in a vacuum oven to give ester 4. $^1$H NMR (CDCl$_3$): δ 7.97 (d, 1H), 6.28 (d, 1H), 3.93 (s, 2H), 3.70 (s, 3H), 3.18 (s, 6H).

Method D:

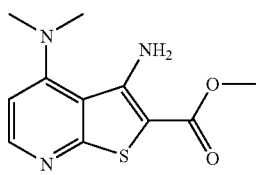

A solution of compound 4 (8.33 g, 0.033 mol) and sodium methoxide (3.77 g, 0.070 mol) in methanol was heated at reflux for 3 hours under a nitrogen atmosphere. The reaction was cooled to room temperature, water was added and the product isolated by extraction with dichloromethane (150 mL). The organic layer was dried over anhydrous sodium sulfate, filtered and evaporated under reduced pressure to give the desired product 5. $^1$H NMR (CDCl$_3$): δ 8.41 (d, 1H), 6.81 (d, 1H), 6.70 (br.s, 2H), 3.82 (s, 3H), 2.81 (s, 6H). Mass Spectrum (M+1)$^+$: m/z calcd. for $C_{11}H_{14}N_3O_2S^+$=252.1, found m/z=252.1.

Method E:

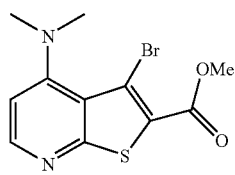

(Ref. Clive, D. L. J.; Sannigrahi, M.; Hisaindee; S. *J. Org. Chem.* 2001, 66, 954-961.) A 3-neck, 2 L round bottom flask was fitted with an overhead mechanical stirrer and an addition funnel, and then charged with CuBr (4.05 g, 28.2 mmol) and aq. 48% HBr (280 mL). The resulting solution was cooled in an ice water bath and then compound 5 was added. To this cooled mixture was added a solution of NaNO$_2$ (2.44 g, 35.4 mmol) in water (65 mL), dropwise. After being stirred for 7 hours while cooled in an ice water bath, a solution of Na$_2$S$_2$O$_3$ (50 g) in water (300 mL). The reaction mixture was carefully quenched by the addition of NaHCO$_3$ (solid, added in portions). Small portions of ethyl acetate were periodically added to control the foaming that occurred during the quench. The quenched mixture was poured into a separatory funnel and extracted with ethyl acetate (3×250 mL). The combined organic and emulsion layers were dried over Na$_2$SO$_4$, overnight. The dried organic layers were filtered, absorbed onto silica gel (25 g), and purified by silica gel chromatography with hexanes/ethyl acetate to afford compound 6 (3.49 g, 39%) as a yellow solid. $^1$HNMR (CDCl$_3$, 400 MHz) δ 8.37 (d, 1H), 6.77 (d, 1H), 3.90 (s, 3H), 2.93 (s, 6H); MS (M+1)$^+$ m/z calcd for $C_{11}H_{12}N_2O_2SBr^+$=314.98, 316.98, found m/z=315.07, 317.04.

Method F:

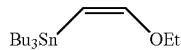

(Ref. Wollenberg, R. H.; Albizati, K. F.; Peries, R. *J. Am. Chem. Soc.* 1977, 99, 22, 7365-7367.) To a −78° C. solution of (Z)-2-ethoxy-1-bromoethene (5.0 mL, 46.8 mmol) in diethyl ether (160 mL) was added a 1.7 M solution of tert-butyl lithium in pentane (55 mL), dropwise over 20 min. This pale yellow solution was stirred at −78° C. for 40 min, and then chloro-tri-n-butylstannane (13.3 mL, 49.0 mmol) was added, dropwise over 7 minutes. The resulting reaction mixture was allowed to warm slowly. Once the cooling bath had reached −30° C., saturated aq. NaHCO$_3$ (150 mL) was added, and the cooling bath was removed. This mixture was stirred for 15 minutes, and then the layers were separated. The aq. layer was extracted with diethyl ether (2×50 mL). The combined organic layers were dried over Na$_2$SO$_4$, filtered, and concentrated to afford (Z)-2-ethoxy-1-tri-n-butylstannanylethene.

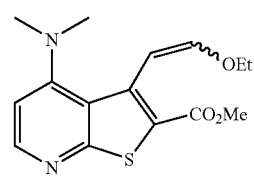

A microwave reaction vial was charged with compound 6 (2.01 g, 6.38 mmol), (Z)-2-ethoxy-1-tri-n-butylstannanylethene (4.61 g, 12.8 mmol), di-iso-propylethylamine (3.3 mL, 19 mmol), and toluene (10 mL). Nitrogen was bubbled through this mixture for several minutes with stirring. Tetrakis(triphenyl-phosphine)palladium (0.37 g, 0.32 mmol) was added to the mixture, and then the vial was sealed. This mixture was irradiated in a microwave reactor for 20 minutes at 180° C. To the resulting black mixture was added aq. 1 M K$_2$CO$_3$ (150 mL), diethyl ether (150 mL) and solid KF. This mixture was stirred vigorously for 1 h, and then the layers were separated. The aq. layer was extracted with diethyl ether (2×150 mL). The combined organic layers were washed with water (3×150 mL), washed with brine (150 mL), dried over Na$_2$SO$_4$, filtered, absorbed onto silica gel (25 g), and purified by silica gel chromatography with hexanes/ethyl acetate to afford compound 7 (1.46 g, 75%) as a 4:1 mixture of Z- and E-isomers, respectively. $^1$HNMR (CDCl$_3$, 400 MHz) δ 8.31 (d, 1H, Z-isomer), 8.30 (d, 1H, E-isomer), 6.87 (d, 1H, Z-isomer), 6.79 (d, 1H, Z-isomer), 6.69 (d, 1H, Z-isomer), 6.65 (d, 1H, E-isomer), 6.23 (d, 1H, E-isomer), 5.99 (d, 1H, E-isomer), 3.95 (q, 2H, Z-isomer), 3.85 (s, 3H, Z-isomer), 3.84 (s, 3H, E-isomer), 3.75 (q, 2H, E-isomer), 2.82 (s, 6H, both isomers), 1.34 (t, 3H, Z-isomer), 1.09 (t, 3H, E-isomer); MS (M+1)$^+$ m/z calcd for $C_{11}H_{12}N_2O_2SBr^+$=307.11, found m/z=307.07.

Method G:

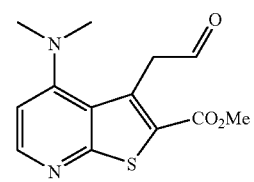

Aq. 1 M HCl (9.5 mL) was added to a solution of compound 7 (1.46 g, 4.76 mmol) in tetrahydrofuran (32 mL). This solution was then heated at reflux for 6.25 hours. The reaction solution was then poured into saturated aq. NaHCO$_3$ (100 mL). This mixture was stirred vigorously for 5 minutes, and then extracted with dichloromethane (3×100 mL). The combined organic layers were dried over Na₂SO₄, filtered, absorbed onto silica gel (10 g), and purified by silica gel chromatography with hexanes/ethyl acetate to afford compound 8 (1.00 g, 75%) as a pale yellow solid. ¹HNMR (CDCl₃, 400 MHz) δ 9.62 (s, 1H), 8.45 (d, 1H), 6.87 (d, 1H), 5.25 (s, 1H), 4.58 (s, 2H), 3.87 (s, 3H), 2.72 (s, 6H); MS (M+1)⁺ m/z calcd for $C_{13}H_{15}N_2O_3S^+$=279.08, found m/z=279.07.

Method H:

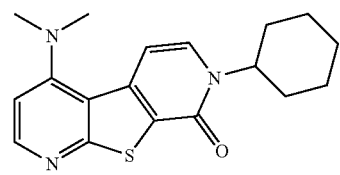

9A

A reaction vessel was charged with compound 8 (0.098 g, 0.35 mmol), cyclohexylamine (0.40 mL, 3.5 mmol), glacial acetic acid (0.18 mL), and toluene (3.5 mL). The vessel was then purged with N₂, sealed, and placed in a 120° C. After being heated for 3.25 hours, the reaction mixture was cooled, diluted with dichloromethane (10 mL), and stirred vigorously with saturated aq. NaHCO₃ (25 mL) for 10 min. The resulting layers were separated, and then the aq. layer was extracted with dichloromethane (2×10 mL). The combined organic layers were dried over Na₂SO₄, filtered, absorbed onto silica gel (2.5 g), and purified by silica gel chromatography with hexanes/ethyl acetate to afford compound 9A (0.0978 g, 85%) as an orange solid/foam. ¹HNMR (CDCl₃, 400 MHz) δ 8.41 (d, 1H), 7.33 (d, 1H), 7.09 (d, 1H), 6.83 (d, 1H), 4.99 (m, 1H), 2.88 (s, 6H); MS (M+1)⁺ m/z calcd for $C_{18}H_{22}N_3OS^+$=328.2, found m/z=328.1.

Method I:

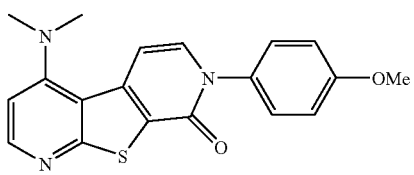

9B

A flask was charged with compound 8 (0.305 g, 1.10 mmol), p-anisidine (0.27 g, 2.2 mmol), 3 Å molecular sieves, and tetrahydrofuran (11 mL), fitted with a reflux condenser, and then placed in a 75° C. oil bath. After being heated at reflux for 1.75 hours, the reaction mixture was removed from the oil bath and then after 5 minutes a 60% NaH oil dispersion was added (0.092 g, 2.3 mmol). The resulting mixture was stirred for 25 minutes, and then quenched with water. This mixture was diluted with dichloromethane and filtered through filter paper. Brine was added and the layers were separated. The aq. layer was extracted with dichloromethane (2×25 mL). The combined organic layers were dried over Na₂SO₄, filtered, absorbed onto silica gel (3.25 g), and purified by silica gel chromatography with hexanes/ethyl acetate to afford compound 9B (0.236 g, 61%) as a yellow solid/foam. ¹HNMR (CDCl₃, 400 MHz) δ 8.47 (d, 1H), 7.36-7.34 (m, 3H), 7.14 (d, 1H), 6.98 (d, 2H), 6.88 (d, 1H), 3.82 (s, 3H), 2.93 (s, 6H); MS (M+1)⁺ m/z calcd for $C_{19}H_{18}N_3O_2S^+$=352.1, found m/z=352.1.

The following compounds were prepared analogously from compounds 8 or 22:

| Cpd | Structure | Formula | Molecular Weight | m/z Found (M + 1)⁺ |
|---|---|---|---|---|
| 9B | 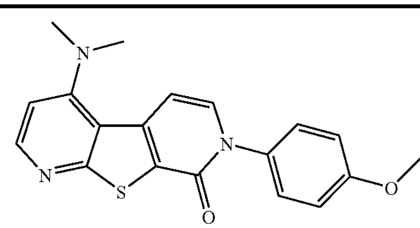 | $C_{19}H_{17}N_3O_2S$ | 351.4 | 352.1 |
| 9C | 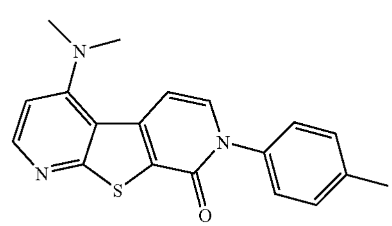 | $C_{19}H_{17}N_3OS$ | 335.4 | 336.1 |
| 9D | 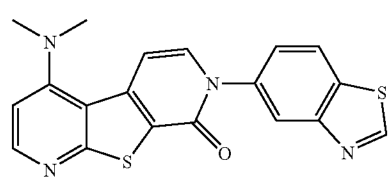 | $C_{19}H_{14}N_4OS_2$ | 378.5 | 379.1 |

-continued

| Cpd | Structure | Formula | Molecular Weight | m/z Found (M + 1)+ |
|---|---|---|---|---|
| 9E | 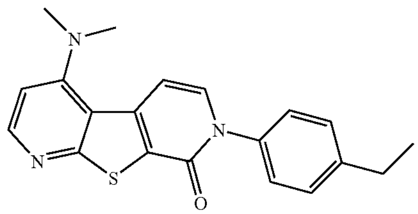 | $C_{20}H_{19}N_3OS$ | 349.4 | 350.1 |
| 9F | 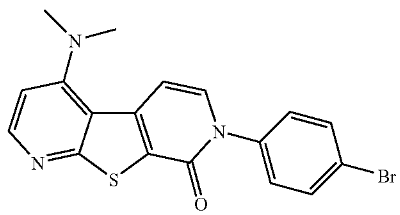 | $C_{18}H_{14}BrN_3OS$ | 400.3 | 402.1 |
| 9G | 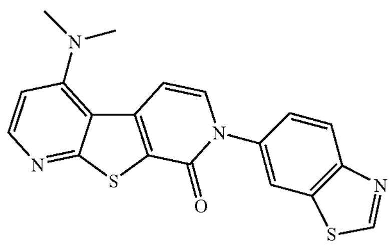 | $C_{19}H_{14}N_4OS_2$ | 378.5 | 379.1 |
| 23A | 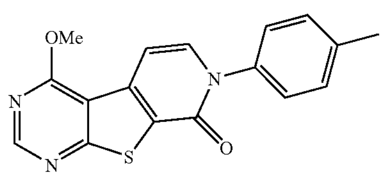 | $C_{17}H_{13}N_3O_2S$ | 323.4 | 324.2 |
| 23B | 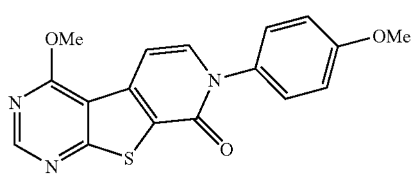 | $C_{17}H_{13}N_3O_3S$ | 339.4 | 340.2 |
| 23C | 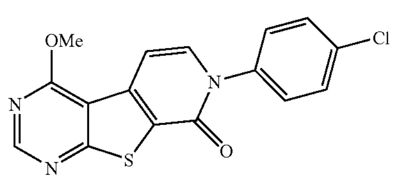 | $C_{16}H_{10}ClN_4O_2S$ | 343.8 | 344.2 |

Method J:

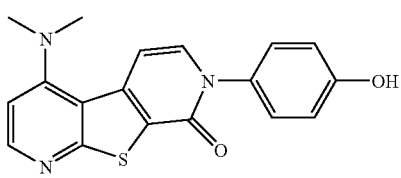

9H

To a 0° C. solution of compound 9B (63 mg, 0.179 mmol) in dichloromethane (3.6 mL) was added a 1.0 M solution of boron tribromide in dichloromethane (0.45 mL). The cooling bath was allowed to warm slowly over 2 hours, until it had reached 16° C. and was removed. The reaction mixture was diluted with methanol (10 mL), and then this solution was concentrated. The oily brown residue was then dissolved in methanol and concentrated again. This resulting light brown residue was stirred for 45 min with saturated aqueous NaHCO$_3$ (50 mL), dichloromethane, and methanol. The layers were separated, and then the aq. layer was extracted with 10% MeOH/dichloromethane (2×10 mL). The combined organic layers were dried over Na$_2$SO$_4$, filtered, absorbed onto silica gel (1.5 g), and purified by silica gel chromatography with methanol/aqueous ammonium hydroxide/dichloromethane to afford compound 9H (0.0238 g, 39%) as an off-white solid. $^1$HNMR (DMF-d$_7$, 400 MHz) δ 10.18 s, 1H), 8.66 (d, 1H), 7.87 (d, 1H), 7.52 (d, 2H), 7.36 (d, 1H), 7.27 (d, 1H), 7.12 (d, 2H), 3.13 (s, 6H); MS (M+1)$^+$ m/z calcd for C$_{18}$H$_{16}$N$_3$O$_2$S$^+$=338.1, found m/z=338.2.

Method K:

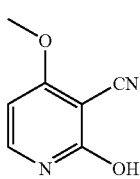

11

(Refs.: (a) S. Yano, T. Ohno, K. Ogawa, *Heterocycles* 1993, 36, 145. (b) M. Mittelbach, G. Kastner, H. Junek, *Arch. Pharm.* 1985, 318, 481.) (1-Ethoxyethylidene)malononitrile (10) (40.0 g, 294 mmol) and N,N-dimethylformamide dimethyl acetal (63.0 ml, 470 mmol) were reacted according to Mittelbach and Yano's procedures to give 23.5 g of 11 as a yellow-orange solid. $^1$H NMR (DMSO-d$_6$) δ12.12 (bs, 1H), 7.77 (d, 1H), 6.33 (d, 1H), 3.95 (s, 3H).

Method L:

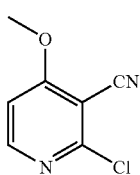

12

To compound 11 (23.5 g, 157 mmol) was added POCl$_3$ (300 mL) and Et$_3$N (15 mL). The reaction mixture was stirred at reflux for 2 hours and the solvents removed in vacuo. The resulting brown solid was quenched dropwise with water and basified with 40% aq. NaOH. The aqueous suspension was extracted with three 100 mL portions of dichloromethane, dried over MgSO$_4$ and concentrated in vacuo to provide 23.9 g of compound 12 as a brown solid. $^1$H NMR (CDCl$_3$) δ8.42 (d, 1H), 6.89 (d, 1H), 4.03 (s, 3H).

Method M:

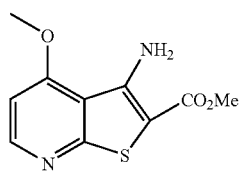

13

To a solution of compound 12 (10.0 g, 59.2 mmol) in 200 mL of DMF was added methylthioglycolate (7.15 mL, 65.0 mmol) and sodium methoxide (3.60 g, 65.0 mmol). The reaction was allowed to stir at room temperature for 2 hours and poured onto 500 mL of water. The solid was filtered off and recrystallized from ethanol to give 10.0 g of yellow solid. To this solid (5.5 g, 23 mmol) in 50 mL of methanol was added sodium methoxide (2.5 g, 46 mmol). The reaction was allowed to stir at reflux for 3 hours and subsequently cooled to room temperature. The reaction mixture was poured onto ice-water and extracted with CH$_2$Cl$_2$ (100 mL×3). The organic layers were combined, dried over MgSO$_4$ and concentrated in vacuo to yield 3.8 g of 13 as a yellow solid. $^1$H NMR (CDCl$_3$) δ8.48 (d, 1H), 6.67 (d, 1H), 6.58 (bs, 2H), 4.04 (s, 3H), 3.86 (s, 3H).

Method N:

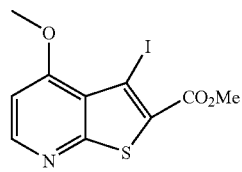

14

To a 48° C. solution of iodine (80 g, 315 mmol) and tert-butyl nitrite (16 mL, 157 mmol) in CH$_3$CN (1 L), was added substrate 13 (25 g, 105 mmol). Vigorous stirring of the resultant suspension was continued for 1 hour at which time the reaction was judged complete by MS. The reaction mixture was cooled to room temperature and then poured into an solution of sodium bisulfite (500 g) in water (2.5 L). Stirring was continued for 30 minutes and then the precipitate isolated by vacuum filtration through paper. The tan solid was air dried and then put under vacuum overnight giving 14 (20 g) as an off white powder. $^1$H NMR (400 MHz:CDCl3) δ8.54 (d, 1H), 6.74 (d, 1H), 3.99 (s, 3H), 3.92 (s, 3H).

The following compound was prepared analogously from compound 20 (Compound 20 was prepared by literature method: Clark, J; Shahhet, M. S.; Korakas, D.; Varvounis, G. *J. Heterocyclic Chem.* 1993, 30, 4, 1065.):

| Cpd | Structure | Formula | Molecular Weight | m/z Found (M + 1)$^+$ |
|---|---|---|---|---|
| 21 | ![structure] | C$_9$H$_7$IN$_2$O$_3$S | 350.1 | 351.0 |

Method O:

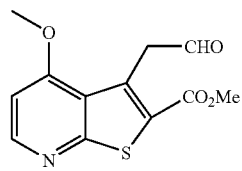

15

Compound 14 (9.2 g, 26.4 mmol) was divided into four portions and placed into four microwave reaction vials. Each vial was then charged with (Z)-2-ethoxy-1-tri-n-butylstannanylethene (5.3 mL, 16.5 mmol), di-iso-propylethylamine (3.4 mL, 19.5 mmol), and toluene (7.8 mL). Nitrogen was bubbled through this mixture for several minutes with stirring. Tetrakis(triphenyl-phosphine)palladium (0.38 g, 0.33 mmol)

was added to the mixture, and then the vial was sealed. This mixture was irradiated in a microwave reactor for 20 minutes at 180° C. The four reaction mixtures were combined, diluted with acetonitrile (200 mL), and extracted with hexanes (3×100 mL). The combined hexane layers were extracted with acetonitrile (2×15 mL). The combined acetonitrile layers were dried over $Na_2SO_4$, filtered, absorbed onto silica gel (26 g), and purified by silica gel chromatography with hexanes/ethyl acetate to afford 4.27 g of a yellow solid. This solid was dissolved in tetrahydrofuran (100 mL), and the aqueous 1 M HCl (29 mL) was added. This resulting solution was then heated at reflux for 2 hours. The reaction solution was then poured into saturated aqueous $NaHCO_3$ (150 mL). This mixture was stirred vigorously for 5 minutes, and then extracted with dichloromethane (1×150 mL, 2×50 mL). The combined organic layers were dried over $Na_2SO_4$, filtered, concentrated, and stored at 5° C. overnight. The crude yellow solid was dissolved in dichloromethane, absorbed onto silica gel (20 g), and purified by silica gel chromatography with hexanes/ethyl acetate to afford compound 15 (2.54 g, 36%) as a pale yellow solid. $^1$HNMR ($CDCl_3$, 400 MHz) δ 9.75 (s, 1H), 8.49 (d, 1H), 6.68 (d, 1H), 4.66 (s, 2H), 3.91 (s, 3H), 3.86(s, 3H); MS $(M+1)^+$ m/z calcd for $C_{12}H_{12}NO_4S^+$=266.05, found m/z=266.11.

Method O (Alternate):

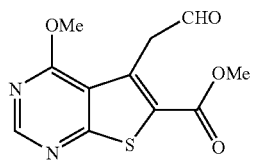

22

To a solution of iodide 21 in toluene (57 mL) was added (Z)-2-ethoxy-1-tri-n-butylstannanylethene (7.8 mL, 24.4 mmol), di-iso-propylethylamine (2.8 mL, 48.9 mmol) and dichlorobis(triphenylphosphine)palladium (0.6 g, 0.82 mmol). The resulting mixture was heated to reflux and allowed to stir for 8 hours. The reaction was then cooled to room temperature and diluted with $CH_2Cl_2$ (150 mL) and washed with 1 M HCl (aq.) (150 mL×2). The organic layer was subsequently dried over $MgSO_4$, filtered, absorbed onto silica gel (15 g), and purified by silica gel chromatography with acetone/$CH_2Cl_2$ to afford 4.10 g of a yellow solid. This solid was dissolved in THF (60 mL), and the aqueous 1M HCl (14.3 mL) was added. This resulting solution was heated at reflux for 5 h. The reaction solution was then poured into saturated aqueous $NaHCO_3$ (100 mL). This mixture was stirred vigorously for 5 min, and then extracted with $CH_2Cl_2$ (100 mL×3). The combined organic layers were dried over $MgSO_4$, filtered, and concentrated in vacuo. The resulting crude yellow oil was purified by silica gel chromatography with acetone/$CH_2Cl_2$ to afford 22 as a pale yellow solid (2.05 g, 47%). $^1$HNMR ($CDCl_3$, 400 MHz) δ 9.82 (s, 1H), 8.71 (s, 1H), 4.69 (s, 2H), 4.12 (s, 3H), 3.92 (s, 3H).

Method P:

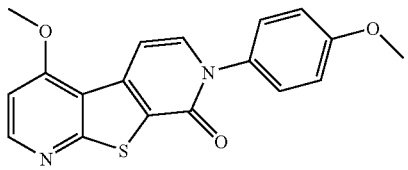

16A

To a room temperature solution of p-anisidine (0.70 g, 5.68 mmol) in toluene (38 mL) added 2 M trimethylaluminum in toluene (2.8 mL, 5.6 mmol). After being stirred for 15 minutes at room temperature, aldehyde 15 (1.00 g, 3.77 mmol) was added, and this mixture was placed in a 115° C. oil bath. After being stirred for 20 hours at 115° C., the reaction solution was poured into a mixture of aqueous 0.5 M Rochelle's salt (100 mL) and dichloromethane (100 mL). This mixture was stirred for 1.5 hours, and then the layers were separated. The aqueous layer was extracted with dichloromethane (2×10 mL). The combined organic layers were dried over $Na_2SO_4$, filtered, absorbed onto silica gel (10 g), and purified by silica gel chromatography with dichloromethane/acetone to afford compound 16A (0.972 g, 76%) as a pale yellow solid. $^1$HNMR ($CDCl_3$, 400 MHz) δ 8.55 (d, 1H), 7.35-7.28 (m, 4H), 6.97 (d, 2H), 6.81 (d, 1H), 4.07 (s, 3H), 3.82(s, 3H); MS $(M+1)^+$ m/z calcd for $C_{18}H_{15}N_2O_3S^+$=339.1, found m/z=339.2.

The following compounds were prepared analogously:

| Cpd | Structure | Formula | Molecular Weight | m/z Found $(M + 1)^+$ |
|---|---|---|---|---|
| 16B | 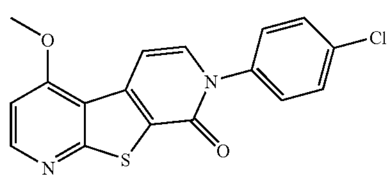 | $C_{17}H_{11}ClN_2O_2S$ | 342.8 | 343.2 |
| 16C | 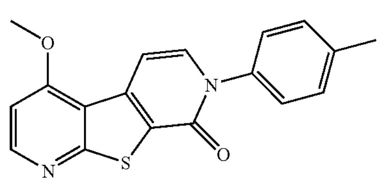 | $C_{18}H_{14}N_2O_2S$ | 322.4 | 323.2 |

-continued
| Cpd | Structure | Formula | Molecular Weight | m/z Found (M + 1)+ |
|---|---|---|---|---|
| 16D | 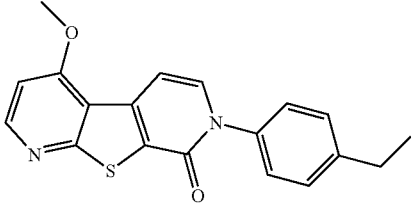 | $C_{19}H_{16}N_2O_2S$ | 336.4 | 337.2 |
| 16E | 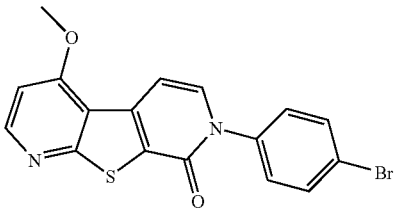 | $C_{17}H_{11}BrN_2O_2S$ | 387.2 | 387.2 |
| 16F | 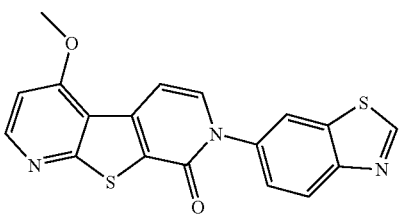 | $C_{18}H_{11}N_3O_2S_2$ | 365.4 | 366.2 |
| 16G | 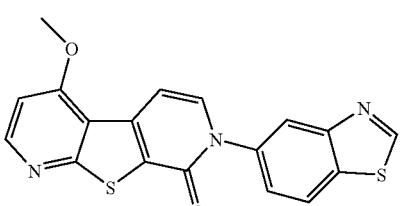 | $C_{18}H_{11}N_3O_2S_2$ | 365.4 | 366.2 |
| 16H | 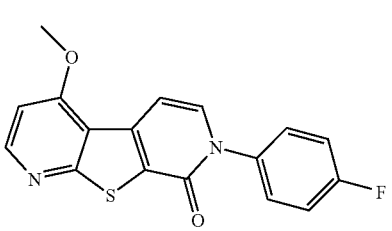 | $C_{17}H_{11}FN_2O_2S$ | 326.3 | 327.2 |
| 16I | 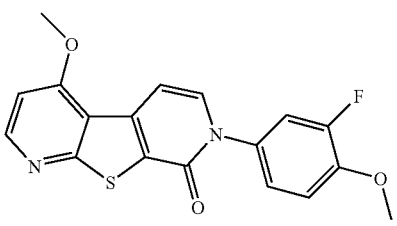 | $C_{18}H_{13}FN_2O_3S$ | 356.3 | 357.2 |
| 16J | 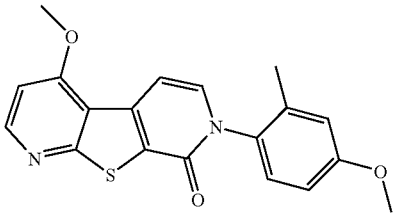 | $C_{19}H_{16}N_2O_3S$ | 352.4 | 353.2 |

-continued

| Cpd | Structure | Formula | Molecular Weight | m/z Found (M + 1)+ |
|---|---|---|---|---|
| 16L | 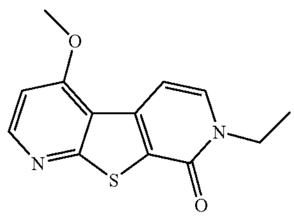 | $C_{13}H_{12}N_2O_2S$ | 260.3 | 261.1 |
| 16M | 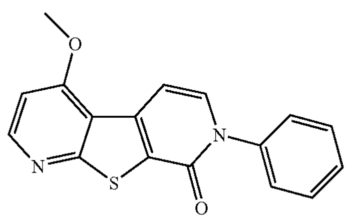 | $C_{17}H_{12}N_2O_2S$ | 308.4 | 309.2 |
| 16N | 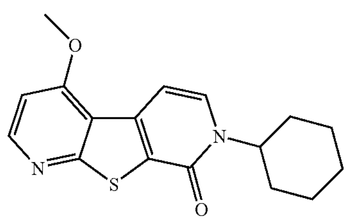 | $C_{17}H_{18}N_2O_2S$ | 314.4 | 315.2 |
| 16O | 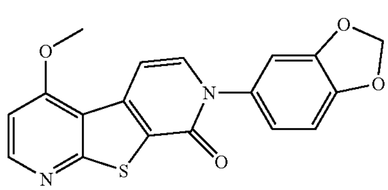 | $C_{18}H_{12}N_2O_4S$ | 352.4 | 353.2 |
| 16P | 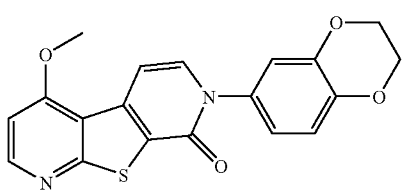 | $C_{19}H_{14}N_2O_4S$ | 366.4 | 367.2 |
| 16Q | 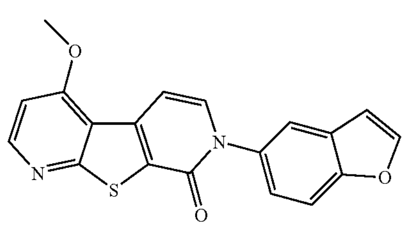 | $C_{19}H_{12}N_2O_3S$ | 348.4 | 349.2 |
| 16R | 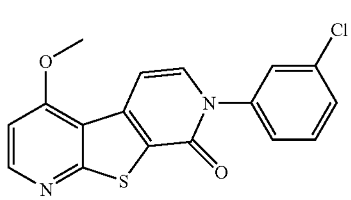 | $C_{17}H_{11}ClN_2O_2S$ | 342.8 | 343.2 |

-continued

| Cpd | Structure | Formula | Molecular Weight | m/z Found (M + 1)+ |
|---|---|---|---|---|
| 16S | 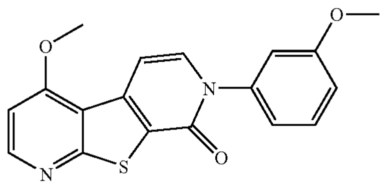 | C18H14N2O3S | 338.4 | 339.2 |
| 16T | 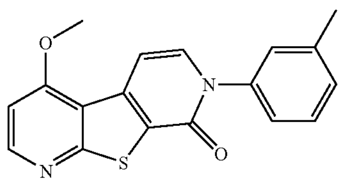 | C18H14N2O2S | 322.4 | 323.2 |
| 16U | 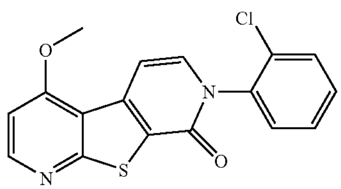 | C17H11ClN2O2S | 342.8 | 343.2 |
| 16V | 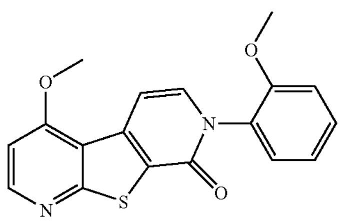 | C18H14N2O3S | 338.4 | 339.2 |
| 16W | 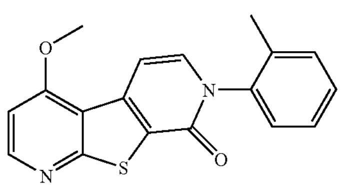 | C18H14N2O2S | 322.4 | 323.2 |
| 16X | 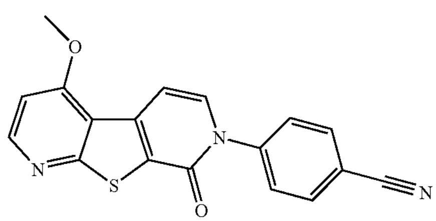 | C18H11N3O2S | 333.4 | 334.2 |
| 16Y | 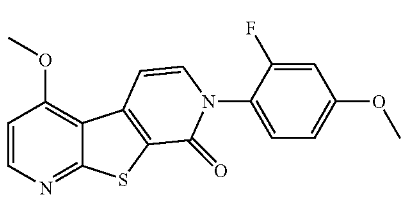 | C18H13FN2O3S | 356.3 | 357.2 |

Method Q:

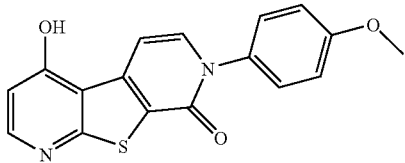

17A

A mixture of compound 16A (75 mg, 0.222 mmol), pyridine-hydrochloride (1.28 g, 11.1 mmol), and chloroform (1.1 mL) was sealed in a vial and heated to 65° C. for 3 days. This mixture was then diluted with water (40 mL) and stirred for 15 minutes. The resulting mixture was filtered. The isolated solid was washed with water and dried to afford compound 17A (60.8 mg, 84%) as a brown solid. MS (M+1)$^+$ m/z calcd for $C_{17}H_{13}N_2O_3S^+$=325.1, found m/z=325.2.

The following compound was prepared analogously:

| Cpd | Structure | Formula | Molecular Weight | m/z Found (M + 1)$^+$ |
|---|---|---|---|---|
| 17D | 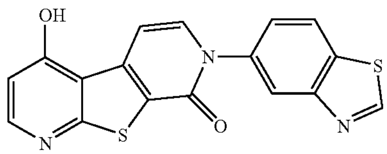 | $C_{17}H_9N_3O_2S_2$ | 351.4 | 352.2 |
| 17E | 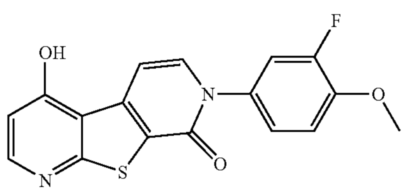 | $C_{17}H_{11}FN_2O_3S$ | 342.3 | 343.2 |
| 17F | 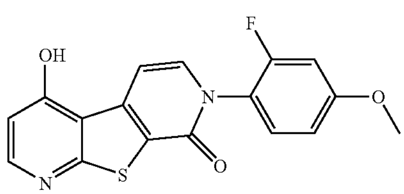 | $C_{17}H_{11}FN_2O_3S$ | 342.3 | 343.2 |
| 25B | 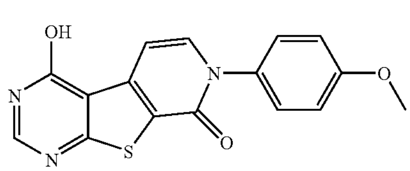 | $C_{16}H_{11}N_3O_3S$ | 325.3 | 326.2 |

Method R:

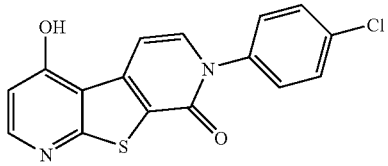
17B

A mixture of compound 16B (140 mg, 0.408 mmol) and 30% HBr in HOAc (3 mL) was sealed in a vial and heated to 100° C. Additional 30% HBr in HOAc (1.5 mL) was added during the total 5 hour heating period. The cooled reaction mixture was diluted with water (50 mL) and filtered. The isolated solid was washed with water and dried to afford compound 17B (115 mg, 86%) as a mustard yellow solid. MS $(M+1)^+$ m/z calcd for $C_{16}H_{10}ClN_2O_2S^+$=329.0, 331.0, found m/z=329.1, 331.1.

The following compound was prepared analogously from compound 16C:

| Cpd | Structure | Formula | Molecular Weight | m/z Found $(M + 1)^+$ |
|---|---|---|---|---|
| 17C | 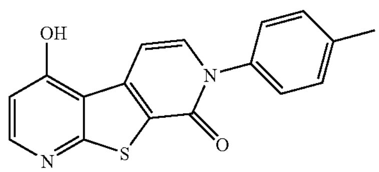 | $C_{17}H_{12}N_2O_2S$ | 308.4 | 309.1 |
| 17G | 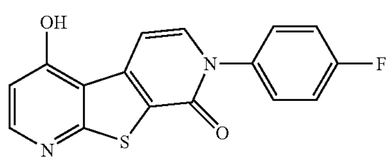 | $C_{16}H_9FN_2O_2S$ | 312.3 | 313.2 |
| 17H | 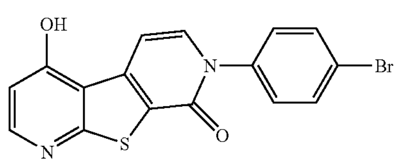 | $C_{16}H_9BrN_2O_2S$ | 373.2 | 373.2 |
| 17I | 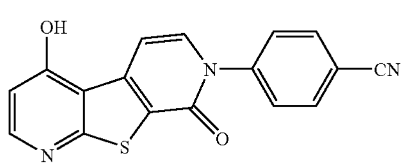 | $C_{17}H_9N_3O_2S$ | 319.3 | 338.2 $(M + H_2O + 1)^+$ |
| 17J | 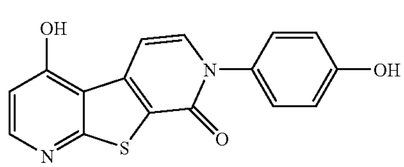 | $C_{16}H_{10}N_2O_3S$ | 310.3 | 311.1 |

Method S:

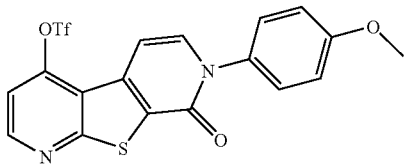
18A

A mixture of compound 17A (58 mg, 0.179 mmol), N-phenyl-bis(trifluoro-methanesulfonimide) (256 mg, 0.717 mmol), di-iso-propylethylamine (0.125 mL, 0.718 mmol), and 1,4-dioxane (1.8 mL) was sealed in a vial and heated to 100° C. for 16 hours. The reaction solution was diluted with ethyl acetate (25 mL), washed with water (1×10 mL), washed with saturated aqueous ammonium chloride (2×10 mL), washed with saturated aqueous sodium bicarbonate (1×10 mL), and washed with brine (1×10 mL). The resulting organic layer was dried over $Na_2SO_4$, filtered, absorbed onto silica gel (2 g), and purified by silica gel chromatography with hexanes/ethyl acetate to afford compound 18A (56.1 mg, 69%) as a dark yellow solid. $^1$HNMR (CDCl$_3$, 400 MHz) δ 8.79 (d, 1H), 7.47-7.42 (m, 2H), 7.34 (d, 2H), 7.17 (d, 1H), 6.97 (d, 2H), 3.81 (s, 3H); MS (M+1)$^+$ m/z calcd for $C_{18}H_{12}F_3N_2O_5S_2^+$= 457.01, found m/z=457.01.

The following compounds were prepared analogously from compounds 17B and 17C:

| Cpd | Structure | Formula | Molecular Weight | m/z Found (M + 1)$^+$ |
|-----|-----------|---------|------------------|----------------------|
| 18B | 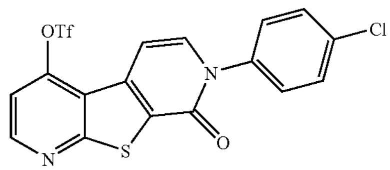 | $C_{17}H_8ClF_3N_2O_4S_2$ | 460.8 | 461.0 |
| 18C | 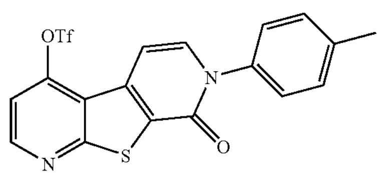 | $C_{18}H_{11}F_3N_2O_4S_2$ | 440.4 | 441.0 |
| 18D | 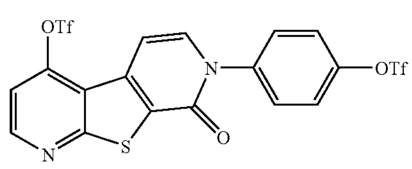 | $C_{18}H_8F_6N_2O_7S_3$ | 574.5 | 575.0 |

Method T:

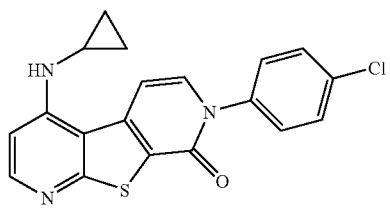

19A

A mixture of compound 18B (62 mg, 0.134 mmol), cyclopropylamine (0.047 mL, 0.68 mmol), and tetrahydrofuran (1.3 mL) was sealed in a vial and heated to 50° C. for 2.75 hours. Additional cyclopropylamine (0.047 mL, 0.68 mmol) was added, and then the mixture was heated at 50° C. for another 0.75 hours. The reaction mixture was allowed to cool overnight, before being absorbed onto silica gel (1.5 g) and purified by silica gel chromatography with dichloromethane/methanol/aqueous ammonium hydroxide to afford compound 19A (21.0 mg, 42%) as a white solid. $^1$HNMR (CDCl$_3$ with CD$_3$OD, 400 MHz) δ 8.20 (d, 1H), 7.36 (d, 2H), 7.28-7.25 (m, 3H), 6.88 (d, 1H), 6.79 (d, 1H), 2.55 (apparent quintet, 1H), 0.87 (apparent quintet, 2H), 0.65 (apparent quintet, 2H); MS (M+1)$^+$ m/z calcd for C$_{19}$H$_{15}$ClN$_3$OS$^+$= 368.1, 370.1, found m/z=368.2, 370.2.

The following compounds were prepared analogously:

| Cpd | Structure | Formula | Molecular Weight | m/z Found (M + 1)$^+$ |
|---|---|---|---|---|
| 19B | 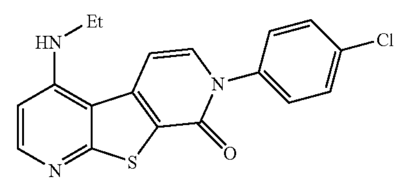 | C$_{18}$H$_{14}$ClN$_3$OS | 355.8 | 356.2 |
| 19C | 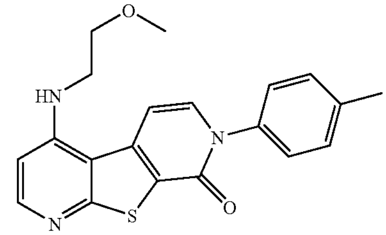 | C$_{20}$H$_{19}$N$_3$O$_2$S | 365.4 | 366.1 |
| 19D | 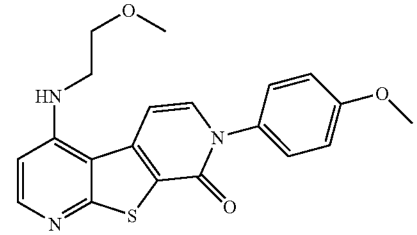 | C$_{20}$H$_{19}$N$_3$O$_2$S | 381.4 | 382.2 |
| 19J | 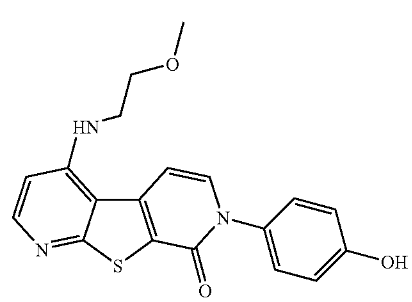 | C$_{19}$H$_{17}$N$_3$O$_3$S | 367.4 | 368.2 |

-continued

| Cpd | Structure | Formula | Molecular Weight | m/z Found (M + 1)+ |
|---|---|---|---|---|
| 19L | 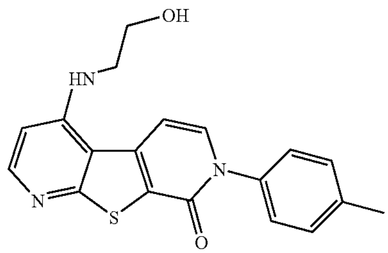 | C19H17N3O2S | 351.4 | 352.1 |
| 19M | 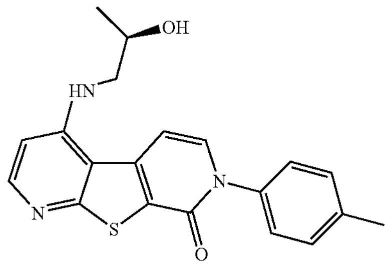 | C20H19N3O2S | 365.4 | 366.2 |
| 19Q | 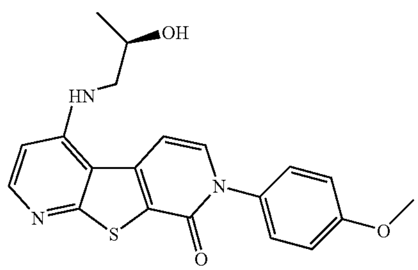 | C20H19N3O3S | 381.4 | 382.1 |
| 19T | 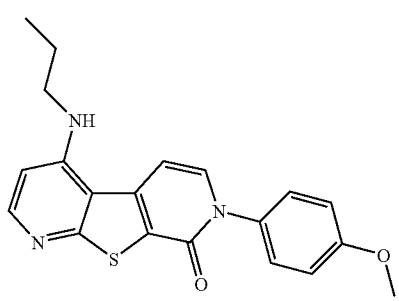 | C20H19N3O2S | 365.4 | 366.2 |
| 19U | 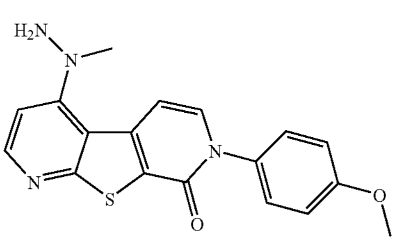 | C18H16N4O2S | 352.4 | 353.2 |

-continued

| Cpd | Structure | Formula | Molecular Weight | m/z Found (M + 1)+ |
|---|---|---|---|---|
| 19V | HO~NH~[structure with pyridothienopyridinone and 4-methoxyphenyl] | C19H17N3O3S | 367.4 | 368.2 |
| 26E | [cyclopropyl-NH structure with pyrimido-thieno-pyridinone and 4-methylphenyl] | C19H16N4OS | 348.4 | 349.2 |

Method U:

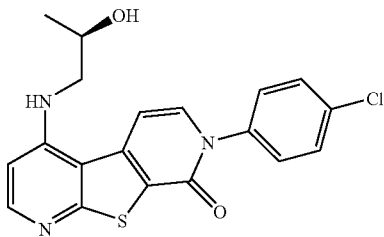

19E

A mixture of compound 18B (76 mg, 0.163 mmol), (R)-1-amino-2-propanol (0.026 mL, 0.33 mmol), tris(dibenzylideneacetone)dipalladium (5 mg, 0.005 mmol), potassium phosphate tribasic (69 mg, 0.33 mmol), and 1,4-dioxane (1.6 mL) was sealed in a vial and heated to 65° C. for 22.5 hours. The reaction mixture was absorbed onto silica gel (2-3 g) and purified by silica gel chromatography with chloroform/methanol to afford compound 19E (13.5 mg, 21%) as a white solid.

$^1$HNMR (DMF-$d_7$, 500 MHz) δ 8.51 (d, 1H), 8.04 (d, 1H), 7.86 (ABq, 4H), 7.70 (d, 1H), 7.05 (d, 1H), 6.93 (t, 1H), 5.34 (s, 1H), 4.34 (m, 1H), 3.73-3.57 (m, 2H), 1.45 (d, 3H); MS (M+1)$^+$ m/z calcd for $C_{19}H_{17}ClN_3O_2S^+$=386.1, 388.1, found m/z=386.2, 388.2.

The following compounds were prepared analogously:

| Cpd | Structure | Formula | Molecular Weight | m/z Found (M + 1)+ |
|---|---|---|---|---|
| 19F | [HO-ethyl-NH structure with pyridothienopyridinone and 4-chlorophenyl] | C18H14ClN3O2S | 371.8 | 372.2 |

-continued

| Cpd | Structure | Formula | Molecular Weight | m/z Found (M + 1)+ |
|---|---|---|---|---|
| 19G | 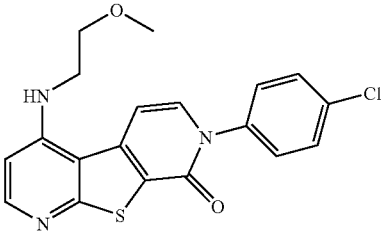 | $C_{19}H_{16}ClN_3O_2S$ | 385.9 | 386.2 |
| 19H | 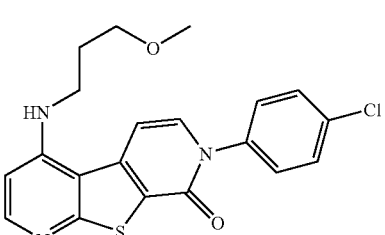 | $C_{20}H_{18}ClN_3O_2S$ | 399.9 | 400.2 |

Method V:

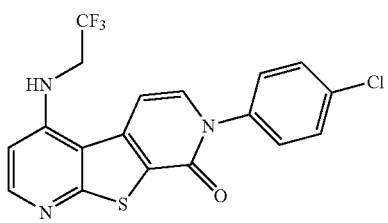

19I

A mixture of compound 18B (0.10 g, 0.22 mmol), 2,2,2-trifluoroethylamine (0.67 mL), and tetrahydrofuran (0.5 mL) was sealed in a microwave vial and heated in a microwave reactor at 120° C. for 0.75 hours. Additional 2,2,2-trifluoroethylamine (0.50 mL) was added to the mixture, which was then further heated in a microwave reactor at 120° C. for 4 hours. The reaction mixture was absorbed onto silica gel (2-3 g) and purified by silica gel chromatography with chloroform/methanol to afford compound 19I (5.5 mg, 6%) as an off-white solid. $^1$HNMR (CDCl$_3$ with CD$_3$OΔ, 400 MHz) δ 8.26 (d, 1H), 7.40 (d, 2H), 7.33-7.30 (m, 3H), 6.95 (d, 1H), 6.56 (d, 1H), 3.98 (q, 2H); MS (M+1)$^+$ m/z calcd for $C_{18}H_{12}ClF_3N_3OS^+$=410.0, 412.0, found m/z=410.2, 412.2.

The following compounds were prepared analogously:

| Cpd | Structure | Formula | Molecular Weight | m/z Found (M + 1)+ |
|---|---|---|---|---|
| 19R | 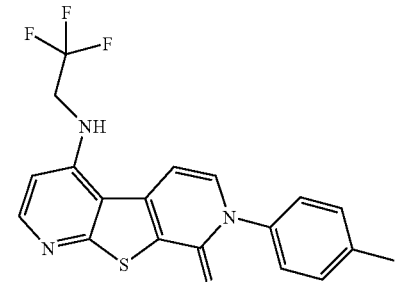 | $C_{19}H_{14}F_3N_3OS$ | 389.4 | 390.2 |

-continued

| Cpd | Structure | Formula | Molecular Weight | m/z Found (M + 1)+ |
|---|---|---|---|---|
| 19S | 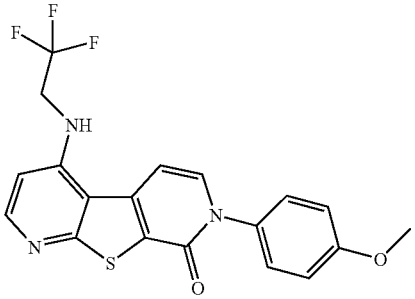 | $C_{19}H_{14}F_3N_3O_2S$ | 405.4 | 406.2 |

Method W:

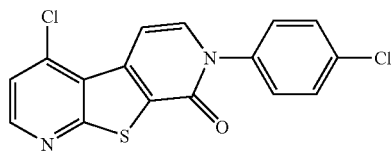

24A

A mixture of compound 17B (0.863 g, 2.62 mmol) and POCl$_3$ (20 mL) was sealed in a sealed tube and placed in a 115° C. oil bath. After being stirred for 3 h, the reaction mixture was concentrated. The resulting brown oil was stirred with saturated aqueous NaHCO$_3$ until bubbling stopped and the pH of the mixture was 8. This mixture was then filtered. The isolated solid was washed with H$_2$O (2×), washed with diethyl ether (2×), and dried under house vacuum to afford compound 24A (0.749 g, 82%). MS (M+1)$^+$ m/z calcd for $C_{16}H_8Cl_2N_2OS^+$=347.0, 349.0, found m/z=347.2, 349.2.

The following compound was prepared analogously:

| Cpd | Structure | Formula | Molecular Weight | m/z Found (M + 1)+ |
|---|---|---|---|---|
| 24B | 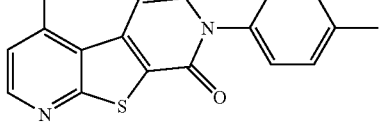 | $C_{17}H_{11}ClN_2OS$ | 326.8 | 327.2 |
| 24C | 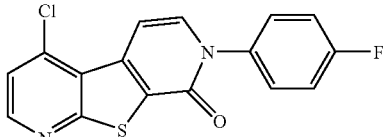 | $C_{16}H_8ClFN_2OS$ | 330.8 | 331.2 |
| 24D | 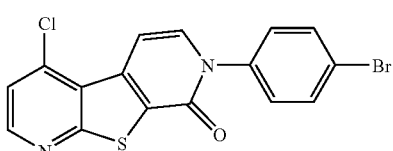 | $C_{16}H_8BrClN_2OS$ | 391.7 | 391.2 |
| 24E | 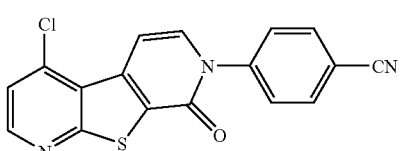 | $C_{17}H_8ClN_3OS$ | 337.8 | 338.2 |

Method X:

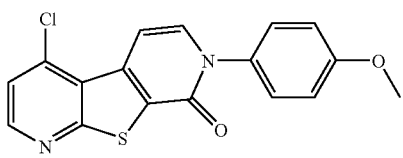

24F

A mixture of compound 17A (1.81 g, 5.58 mmol), p-toluenesulfonyl chloride (4.26 g, 22.3 mmol), di-iso-propylethylamine (4.0 mL, 22.4 mmol), and 1,4-dioxane (56 mL) was placed in a 65° C. oil bath. After being stirred for 6 h, lithium chloride (2.4 g, 57 mmol) and tetraethylammonium chloride (9.2 g, 56 mmol) were added to the 65° C. reaction mixture. The resulting mixture was poured into H$_2$O (1 L). This mixture was stirred for 1 h and then filtered. The isolated solid was washed with H$_2$O (2×200 mL), washed with diethyl ether (4×100 mL), suspended in dichloromethane. This suspension was transferred to a flask and concentrated to afford compound 24F (1.67 g, 87%). MS (M+1)$^+$ m/z calcd for C$_{16}$H$_8$Cl$_2$N$_2$OS$^+$=343.0, 345.0, found m/z=343.2, 345.2.

The following compound was prepared analogously:

| Cpd | Structure | Formula | Molecular Weight | m/z Found (M + 1)$^+$ |
|---|---|---|---|---|
| 24G | 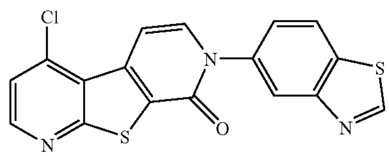 | C$_{17}$H$_8$ClN$_3$OS$_2$ | 369.8 | 370.2 |
| 24H | 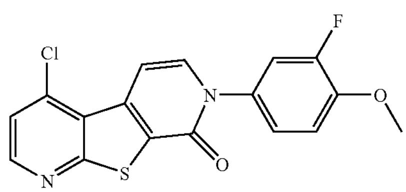 | C$_{17}$H$_{10}$ClFN$_2$O$_2$S | 360.8 | 361.2 |
| 24I | 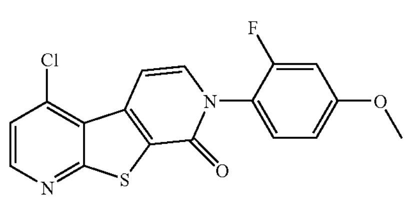 | C$_{17}$H$_{10}$ClFN$_2$O$_2$S | 360.8 | 361.2 |

Method Y:

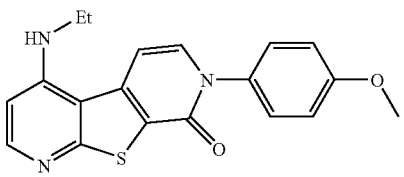

19O

A mixture of compound 24F (0.49 g, 1.43 mmol), 2 M ethylamine in tetrahydrofuran (7 mL), and dimethylsulfoxide (7 mL) was sealed in a sealed tube and placed in a 65° C. oil bath. After being stirred for 22 h, additional 2 M ethylamine in tetrahydrofuran (10.5 mL) and dimethylsulfoxide (7 mL) were added to the reaction mixture. After being stirred for an additional 24 h, the reaction solution was diluted with chloroform (150 mL). This solution was then washed with $H_2O$ (3×150 mL), dried over $Na_2SO_4$, filtered, and absorbed onto 5 g of silica gel. This absorbed crude material was purified by silica gel chromatography with dichloromethane/methanol/ammonium hydroxide to afford compound 190 (0.435 g, 87%) as a foam. $^1$HNMR (CDCl$_3$+CD$_3$OD (as minor cosolvent), 400 MHz) δ 8.32 (d, 1H), 7.35-7.30 (m, 3H), 6.96 (d, 2H), 6.78 (d, 1H), 6.51 (d, 1H), 4.99 (br s, 1H), 3.84(s, 3H), 3.39 (q, 2H), 1.43 (t, 3H); MS (M+1)$^+$ m/z calcd for $C_{19}H_{17}N_3O_2S^+$=352.1, found m/z=352.2.

The free base of compound 190 (0.435 g) was dissolved in methanol, chloroform, and 2 M HCl in diethyl ether. This solution was concentrated to afford the HCl salt of compound 190 (0.450 g) as a pale yellow solid.

The following compound was prepared analogously:

| Cpd | Structure | Formula | Molecular Weight | m/z Found (M + 1)$^+$ |
|---|---|---|---|---|
| 19K | 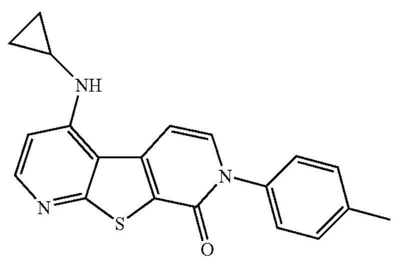 | $C_{20}H_{17}N_3OS$ | 347.4 | 348.2 |
| 19N | 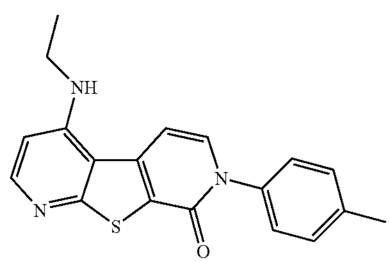 | $C_{19}H_{17}N_3OS$ | 335.4 | 336.2 |
| 19P | 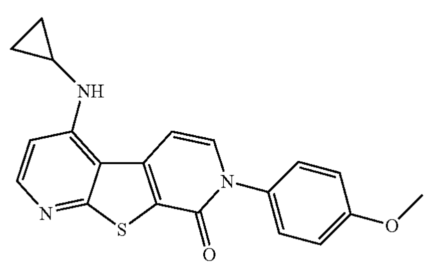 | $C_{20}H_{17}N_3O_2S$ | 363.4 | 364.2 |
| 19W | 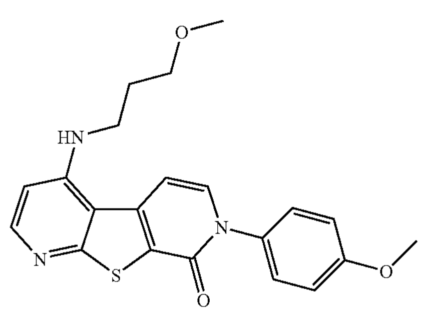 | $C_{21}H_{21}N_3O_3S$ | 395.5 | 396.2 |

-continued

| Cpd | Structure | Formula | Molecular Weight | m/z Found (M + 1)+ |
|---|---|---|---|---|
| 19X | 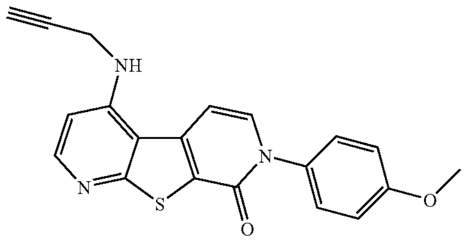 | C20H15N3O2S | 361.4 | 362.2 |
| 19Y | 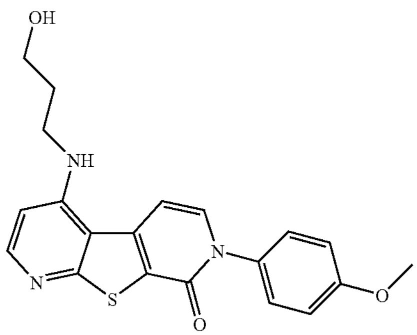 | C20H19N3O3S | 381.4 | 382.2 |
| 19Z | 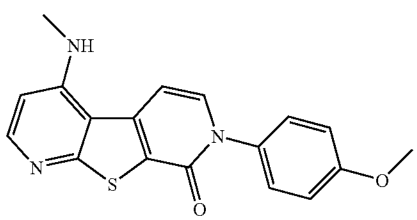 | C18H15N3O2S | 337.4 | 338.2 |
| 19AA | 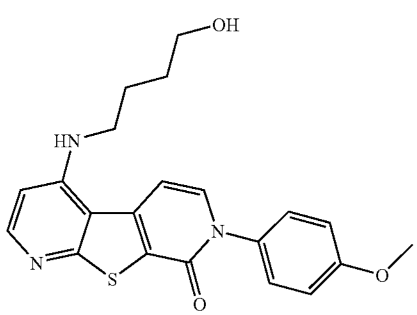 | C21H21N3O3S | 395.5 | 396.2 |
| 19AB | 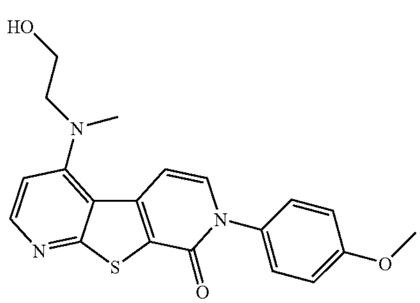 | C20H19N3O3S | 381.4 | 382.2 |

-continued

| Cpd | Structure | Formula | Molecular Weight | m/z Found (M + 1)+ |
|---|---|---|---|---|
| 19AD | 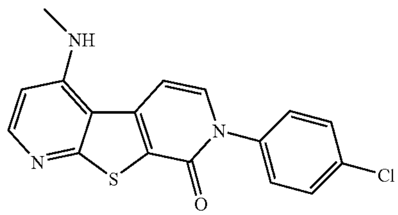 | C17H12ClN3OS | 341.8 | 342.2 |
| 19AE | 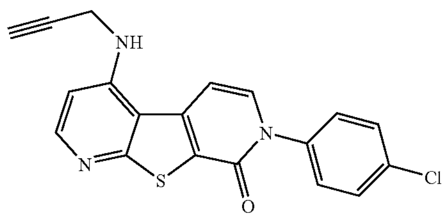 | C19H12ClN3OS | 365.8 | 366.2 |
| 19AF | 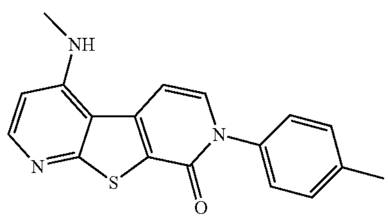 | C18H15N3OS | 321.4 | 322.2 |
| 19AH | 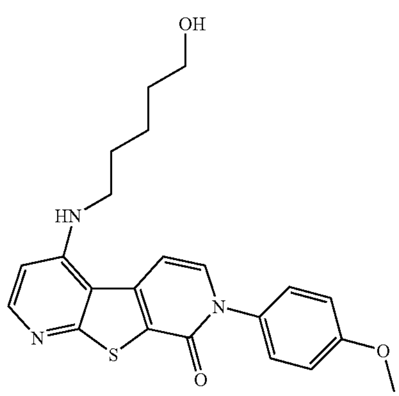 | C22H23N3O3S | 409.5 | 410.2 |
| 19AI | 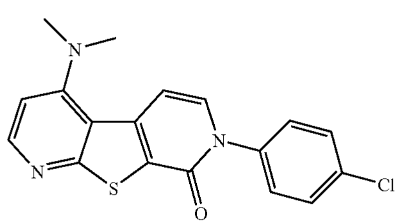 | C18H14ClN3OS | 355.8 | 356.2 |
| 19AJ | 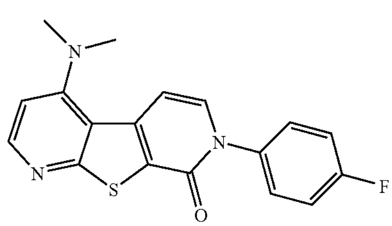 | C18H14FN3OS | 339.4 | 340.2 |

-continued

| Cpd | Structure | Formula | Molecular Weight | m/z Found (M + 1)+ |
| --- | --- | --- | --- | --- |
| 19AK | 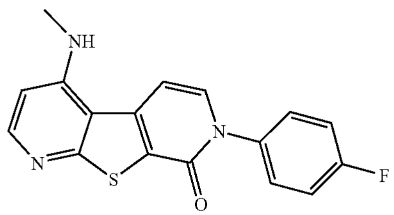 | $C_{17}H_{12}FN_3OS$ | 325.4 | 326.2 |
| 19AL | 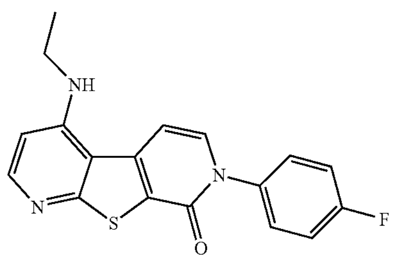 | $C_{18}H_{14}FN_3OS$ | 339.4 | 340.2 |
| 19AM | 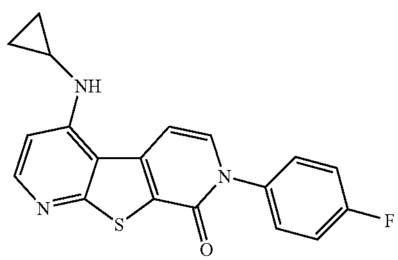 | $C_{19}H_{14}FN_3OS$ | 351.4 | 352.2 |
| 19AN | 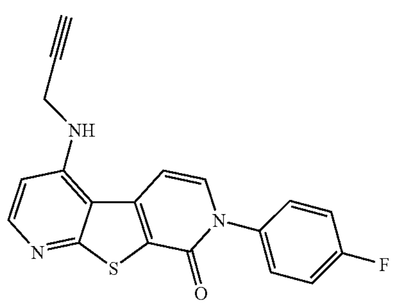 | $C_{19}H_{12}FN_3OS$ | 349.4 | 350.2 |
| 19AO | 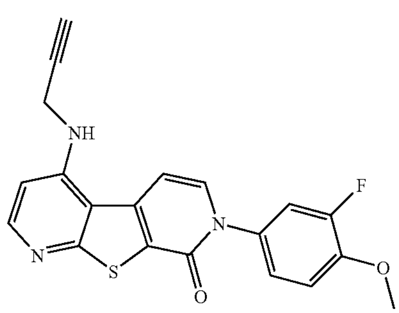 | $C_{20}H_{14}FN_3O_2S$ | 379.4 | 380.2 |

| Cpd | Structure | Formula | Molecular Weight | m/z Found (M + 1)+ |
|---|---|---|---|---|
| 19AP | 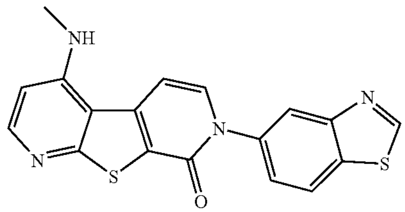 | C₁₈H₁₂N₄OS₂ | 364.4 | 365.2 |
| 19AQ | 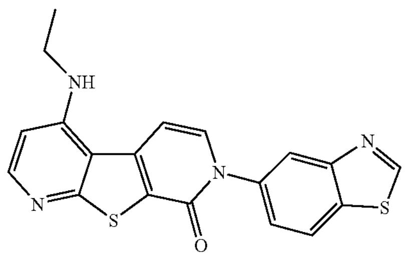 | C₁₉H₁₄N₄OS₂ | 378.5 | 379.2 |
| 19AR | 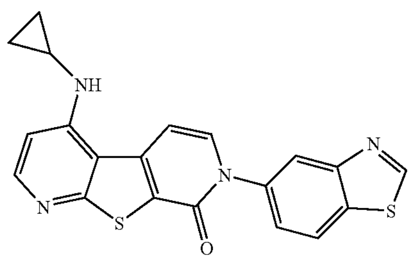 | C₂₀H₁₄N₄OS₂ | 390.5 | 391.2 |
| 19AS | 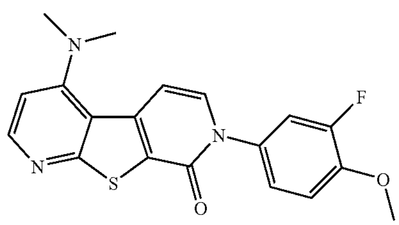 | C₁₉H₁₆FN₃O₂S | 369.4 | 370.2 |
| 19AT | 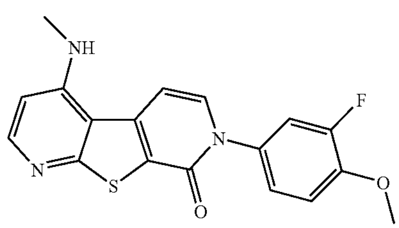 | C₁₈H₁₄FN₃O₂S | 355.4 | 356.2 |
| 19AU | 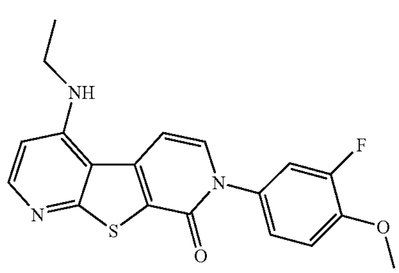 | C₁₉H₁₆FN₃O₂S | 369.4 | 370.2 |

-continued

| Cpd | Structure | Formula | Molecular Weight | m/z Found (M + 1)+ |
|---|---|---|---|---|
| 19AV | 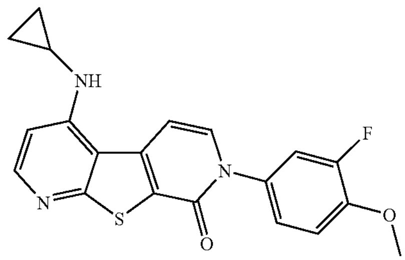 | $C_{20}H_{16}FN_3O_2S$ | 381.4 | 382.2 |
| 19AW | 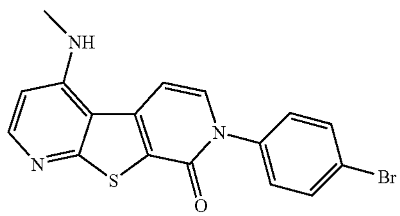 | $C_{17}H_{12}BrN_3OS$ | 386.3 | 386.2 |
| 19AX | 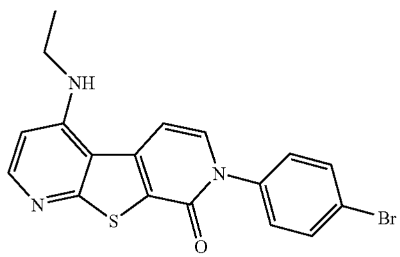 | $C_{18}H_{14}BrN_3OS$ | 400.3 | 400.2 |
| 19AY | 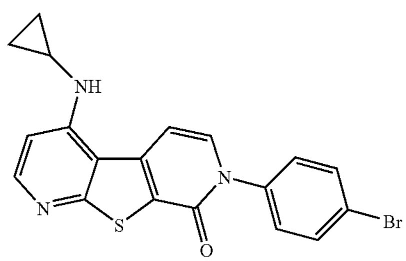 | $C_{19}H_{14}BrN_3OS$ | 412.3 | 412.2 |
| 19AZ | 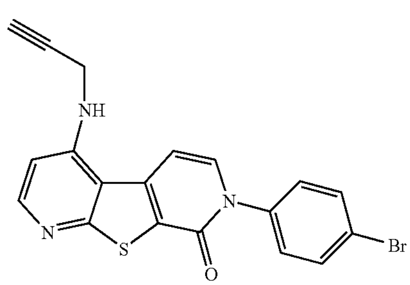 | $C_{19}H_{12}BrN_3OS$ | 410.3 | 410.2 |
| 19BA | 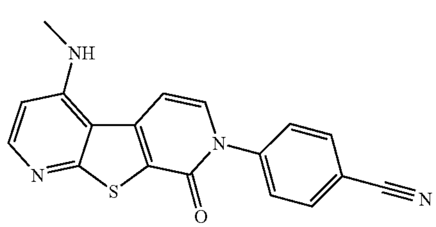 | $C_{18}H_{12}N_4OS$ | 332.4 | 333.2 |

-continued

| Cpd | Structure | Formula | Molecular Weight | m/z Found (M + 1)+ |
|---|---|---|---|---|
| 19BB | 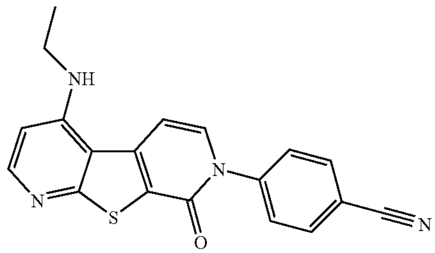 | $C_{19}H_{14}N_4OS$ | 346.4 | 347.2 |
| 19BC | 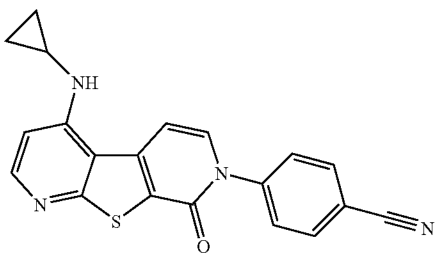 | $C_{20}H_{14}N_4OS$ | 358.4 | 359.2 |
| 19BD | 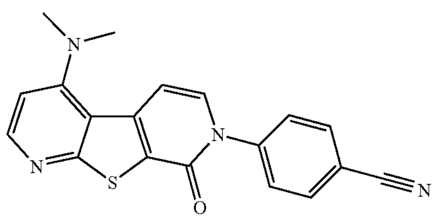 | $C_{19}H_{14}N_4OS$ | 346.4 | 347.2 |
| 19BE | 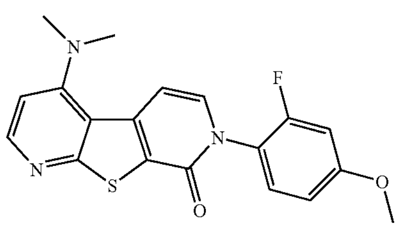 | $C_{19}H_{16}FN_3O_2S$ | 369.4 | 370.2 |
| 19BF | 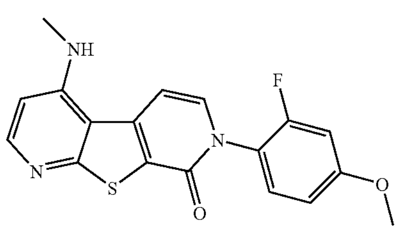 | $C_{18}H_{14}FN_3O_2S$ | 355.4 | 356.2 |
| 19BG | 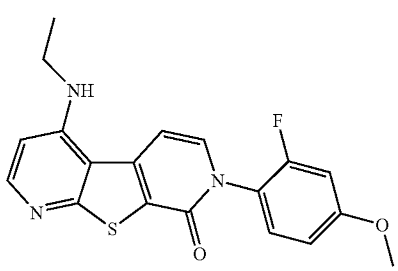 | $C_{19}H_{16}FN_3O_2S$ | 369.4 | 370.2 |

| Cpd | Structure | Formula | Molecular Weight | m/z Found (M + 1)+ |
|---|---|---|---|---|
| 19BH | 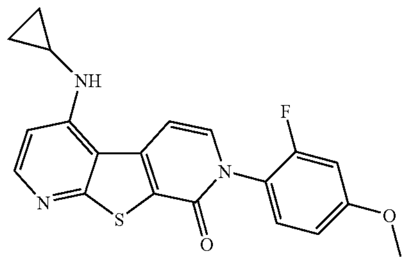 | C20H16FN3O2S | 381.4 | 382.2 |
| 26B | 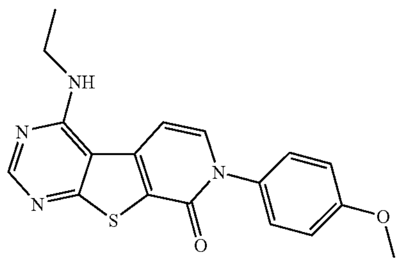 | C18H16N4O2S | 352.4 | 353.2 |
| 26C | 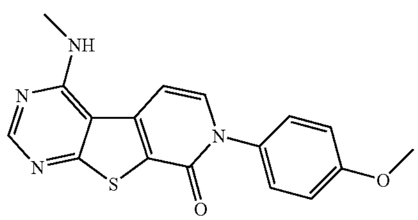 | C17H14N4O2S | 338.4 | 339.2 |

Method Z:

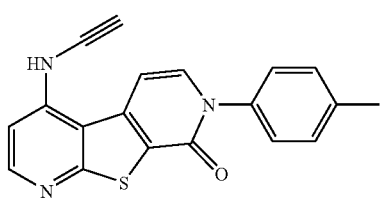

19AG

Method AA:

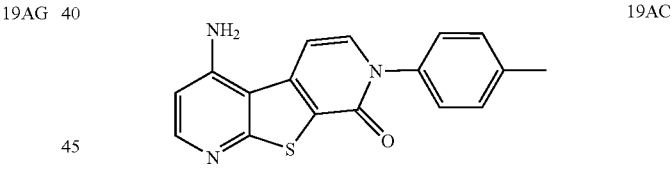

19AC

A mixture of compound 24B (29 mg, 0.089 mmol) and propargylamine (2.7 mL) was sealed in a vial and placed in a 65° C. heating block. After being stirred for 4 d at 65° C., the reaction solution was diluted with CHCl3 and absorbed onto 1 g of silica gel. This absorbed crude material was purified twice by silica gel chromatography with dichloromethane/methanol/ammonium hydroxide to provide an off-white solid (19 mg). This solid was stirred with diethyl ether (25 mL) for 1 h, and then the resulting suspension was filtered. The isolated solid was washed with diethyl ether (2×) and dried under house vacuum to afford compound 19AG (13 mg, 42%) as a pale orange solid. $^1$HNMR (CDCl3+CD3OD (as minor cosolvent), 400 MHz) δ 8.29 (d, 1H), 7.42 (d, 1H), 7.26 (s, 4H), 7.11 (d, 1H), 6.70 (d, 1H), 4.17 (d, 2H), 2.36 (s, 3H), 2.33 (t, 1H); MS (M+1)+ m/z calcd for $C_{20}H_{15}N_3OS^+$=346.1, found m/z=346.2.

A mixture of compound 16C (27 mg, 0.084 mmol) and ammonium acetate (1.3 g) was sealed in a vial and placed in a 150° C. heating block. After being stirred for 3 d at 150° C., the reaction mixture was stirred with H2O (25 mL) for 0.75 h. This mixture was then filtered. The resulting solid was washed with H2O (10 mL), dried overnight under house vacuum, and then purified by reverse phase HPLC with acetonitrile/water/formic acid to afford compound 19AC (2.5 mg) as a yellow solid.

$^1$HNMR (CDCl3+CD3OD (1:1 mixture), 400 MHz) δ 7.88 (br s, 1H), 7.27(d, 1H), 7.07 (s, 4H), 7.00 (d, 1H), 6.42 (d, 1H), 3.89 (br s, 2H), 2.16 (s, 3H); MS (M+1)+ m/z calcd for $C_{17}H_{13}N_3OS^+$=307.4, found m/z=308.2.

Method AB:

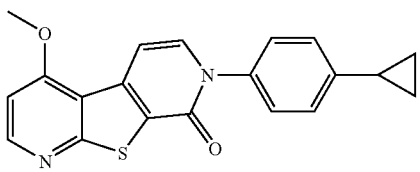

16K

Nitrogen was bubbled through a mixture of compound 16E (60 mg, 0.155 mmol), cyclopropylboronic acid (27 mg, 0.31 mmol), $K_3PO_4$ (108 mg, 0.51 mmol), NaBr (16 mg, 0.16 mmol), and toluene (5 mL) for several minutes.

Tetrakis(triphenylphosphine)palladium(0) (9 mg, 0.008 mmol) was added to the mixture, which was then placed in a 100° C. oil bath. After being stirred for 1 d at 100° C., additional cyclopropylboronic acid (54 mg, 0.63 mmol) and tetrakis(triphenylphosphine)palladium(0) (9 mg, 0.008 mmol) were added. After being stirred for another 1 d at 100° C., cyclopropylboronic acid (27 mg, 0.31 mmol), $K_3PO_4$ (108 mg, 0.51 mmol), water (0.05 mL), tricyclohexylphosphine (9 mg, 0.032 mmol) and palladium(II) acetate (3.5 mg, 0.016 mmol) were added. After being stirred for another 1 d at 100° C., the reaction mixture was diluted with water. This mixture was extracted with dichloromethane. The layers were separated, and then the emulsion/aqueous layer were filtered through a fritted cartridge. The resulting filtrate was extracted with dichloromethane (2×). The combined organic layers were dried over $Na_2SO_4$, filtered, absorbed onto 2 g of silica gel, and purified by silica gel chromatography with dichloromethane/acetone to afford compound 16K (20.9 mg, 39%) as an off-white residue. $^1$HNMR (CDCl$_3$, 400 MHz) δ 8.53 (d, 1H), 7.32-7.29 (m, 4H), 7.18 (d, 2H), 6.80 (d, 1H), 4.06 (s, 3H), 1.91 (tt, 1H), 0.97 (dddd, 1H), 0.70 (dddd, 1H); MS (M+1)$^+$ m/z calcd for $C_{20}H_{16}N_2O_2S^+$=348.4, found m/z=349.2.

Method AC:

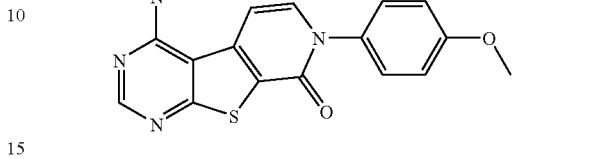

26A

To a room temperature mixture of compound 25A (0.226 g, 0.69 mmol), di-iso-propylethylamine (0.37 mL, 2.1 mmol), 4-dimethylaminopyridine (4 mg, 0.033 mmol) and chloroform (6.9 mL) was added 2,4,6-tri-isopropylbenzenesulfonyl chloride (0.42 g, 1.4 mmol). After being stirred for 50 min at room temperature, this reaction mixture was divided into four equal portions. To one portion of this reaction mixture was added a 2 M solution of dimethylamine in tetrahydrofuran (1.75 mL). After being stirred for 15.5 h at room temperature, the reaction mixture was purified by silica gel chromatography with dichloromethane/methanol/ammonium hydroxide to provide an off-white solid (12.3 mg). The resulting solid purified by reverse phase HPLC with acetonitrile/water/formic acid to afford compound 26A (2.6 mg) as a white solid.

$^1$HNMR (CDCl$_3$+CD$_3$OD (as minor cosolvent), 400 MHz) δ 8.52 (br s, 1H), 7.39(d, 1H), 7.29 (d, 2H), 6.96 (d, 2H), 6.86 (d, 1H), 3.79 (s, 3H), 3.15 (s, 6H); MS (M+1)$^+$ m/z calcd for $C_{18}H_{16}N_4O_2S^+$=352.4, found m/z=353.2.

The following compound was prepared analogously:

| Cpd | Structure | Formula | Molecular Weight | m/z Found (M + 1)$^+$ |
|---|---|---|---|---|
| 26D | 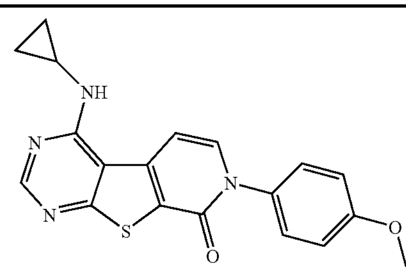 | $C_{19}H_{16}N_4O_2S$ | 364.4 | 365.2 |
| 26F | 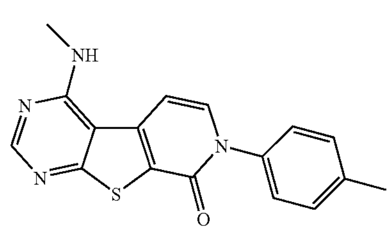 | $C_{17}H_{14}N_4OS$ | 322.4 | 323.2 |

-continued

| Cpd | Structure | Formula | Molecular Weight | m/z Found (M + 1)+ |
|---|---|---|---|---|
| 26G | 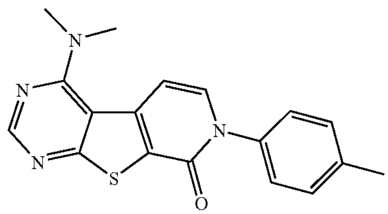 | C₁₈H₁₆N₄OS | 336.4 | 337.2 |
| 26H | 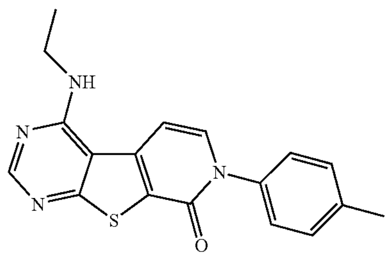 | C₁₈H₁₆N₄OS | 336.4 | 337.2 |

IC$_{50}$ Determination

A CHO cell line stably expressing hmGluR1 receptor was established. One day prior to assay, cells were split in growth media at concentration of 50,000 cells/well in a volume of 100 µl and seeded into black clear-bottom 96-well plates. After two to six hours, when cells were well attached to the plate, growth medium was replaced with assay medium (100 µL) consisting of DMEM high glucose, supplemented with GPT (1 U/mL) and sodium pyruvate, 1 mM. Following overnight incubation, medium was discarded and cells were loaded for 2 hours with dye from the Calcium 3 Assay Reagent Kit (Molecular Devices, # R8033), prepared according to manufacturers' instructions. A 96-tip pipettor/fluorometric imaging plate reader (FLIPR 384; Molecular Devices) was used and intracellular calcium mobilization was measured by increases in fluorescence upon agonist Quisqualate stimulation following 6 sec-baseline measurement. Test compounds were added 10 minutes before Quisqualate. IC$_{50}$ determinations for tested compounds were generated against Quisqualate 1 µM corresponding to EC$_{80}$ value in a standard dose response curve.

In the table below, those compounds having an mGluR1 IC$_{50}$ value of less than 20 nM (<20 nM) are designated with letter "A"; those with an IC$_{50}$ value of from 20 to less than 100 nM (20-<100 nM) are designated with letter "B"; those with an IC$_{50}$ value of from 100 to 1000 nM are designated with letter "C"; and those with an IC$_{50}$ value of more than 1000 nM (>1000 nM) are designated with letter "D".

TABLE 2

| Cpd | Cpd | mGluR1 IC$_{50}$ rating |
|---|---|---|
| 9A | | A |
| 9B | | A |

TABLE 2-continued

| Cpd | Cpd | mGluR1 IC$_{50}$ rating |
|---|---|---|
| 9C | | A |
| 9D | | A |
| 9E | | A |
| 9F | | A |
| 9G | | A |
| 9H | | A |
| 16A | | A |

TABLE 2-continued

| Cpd | Cpd | mGluR1 IC$_{50}$ rating |
|---|---|---|
| 16B | | A |
| 16C | | A |
| 16D | | B |
| 16E | | A |
| 16F | | B |
| 16G | | A |
| 16H | | A |

TABLE 2-continued

| Cpd | Cpd | mGluR1 IC$_{50}$ rating |
|---|---|---|
| 16I | | A |
| 16J | | B |
| 16K | | B |
| 16L | | D |
| 16M | | A |
| 16N | | A |
| 16O | | A |

TABLE 2-continued

| Cpd | Cpd | mGluR1 IC$_{50}$ rating |
|---|---|---|
| 16P | | B |
| 16Q | | A |
| 16R | | A |
| 16S | | C |
| 16T | | A |
| 16U | | B |
| 16V | | D |
| 16W | | B |

TABLE 2-continued

| Cpd | Cpd | mGluR1 IC$_{50}$ rating |
|---|---|---|
| 16X | (structure: 4-methoxy pyrido-thieno-pyridinone with 4-cyanophenyl) | B |
| 17A | (structure: 4-hydroxy pyrido-thieno-pyridinone with 4-methoxyphenyl) | D |
| 17B | (structure: 4-hydroxy pyrido-thieno-pyridinone with 4-chlorophenyl) | C |
| 17C | (structure: 4-hydroxy pyrido-thieno-pyridinone with 4-methylphenyl) | C |
| 19A | (structure: 4-cyclopropylamino pyrido-thieno-pyridinone with 4-chlorophenyl) | A |
| 19B | (structure: 4-ethylamino pyrido-thieno-pyridinone with 4-chlorophenyl) | A |
| 19C | (structure: 4-(2-methoxyethylamino) pyrido-thieno-pyridinone with 4-methylphenyl) | B |

TABLE 2-continued

| Cpd | Cpd | mGluR1 IC$_{50}$ rating |
|---|---|---|
| 19D | | C |
| 19E | | B |
| 19F | | A |
| 19G | | B |
| 19H | | B |

TABLE 2-continued

| Cpd | Cpd | mGluR1 IC$_{50}$ rating |
|---|---|---|
| 19I | | B |
| 19J | | D |
| 19K | | A |
| 19L | | B |
| 19M | | B |
| 19N | | A |

TABLE 2-continued

| Cpd | Cpd | mGluR1 IC$_{50}$ rating |
|---|---|---|
| 19O | | A |
| 19P | | A |
| 19Q | | C |
| 19R | | B |
| 19S | | B |

TABLE 2-continued

| Cpd | Cpd | mGluR1 IC$_{50}$ rating |
|---|---|---|
| 19T | | B |
| 19U | | A |
| 19V | | C |
| 19W | | B |
| 19X | | B |

TABLE 2-continued

| Cpd | Cpd | mGluR1 IC$_{50}$ rating |
|---|---|---|
| 19Y | (structure) | B |
| 19Z | (structure) | B |
| 19AA | (structure) | B |
| 19AB | (structure) | A |
| 19AC | (structure) | B |
| 19AD | (structure) | A |

TABLE 2-continued
| Cpd | Cpd | mGluR1 IC$_{50}$ rating |
|---|---|---|
| 19AE | 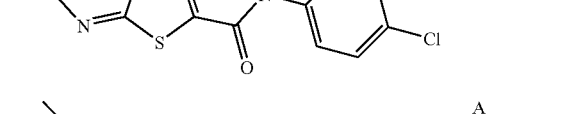 | A |
| 19AF | 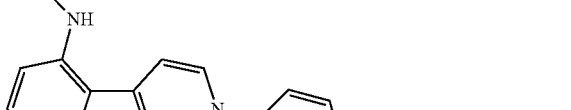 | A |
| 19AG | 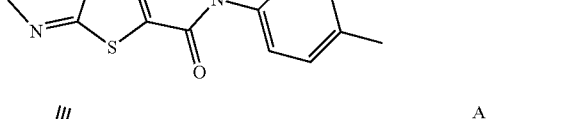 | A |
| 19AH |  | B |
| 19AI | 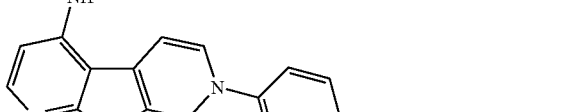 | A |
| 19AJ | 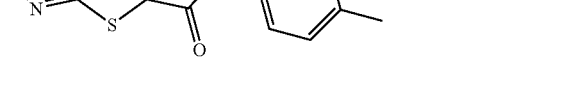 | A |

TABLE 2-continued

| Cpd | Cpd | mGluR1 IC$_{50}$ rating |
|---|---|---|
| 19AK | | B |
| 19AL | | B |
| 19AM | | B |
| 19AN | | B |
| 19AO | | C |
| 19AP | | B |

TABLE 2-continued

| Cpd | Cpd | mGluR1 IC$_{50}$ rating |
|---|---|---|
| 19AQ | (structure) | B |
| 19AR | (structure) | B |
| 19AS | (structure) | A |
| 19AT | (structure) | B |
| 19AU | (structure) | A |
| 19AV | (structure) | A |

TABLE 2-continued

| Cpd | Cpd | mGluR1 IC$_{50}$ rating |
|---|---|---|
| 19AW | (4-methylamino substituent) | A |
| 19AX | (4-ethylamino substituent) | A |
| 19AY | (4-cyclopropylamino substituent) | A |
| 19AZ | (4-propargylamino substituent) | A |
| 19BA | (4-methylamino, N-(4-cyanophenyl)) | C |
| 19BB | (4-ethylamino, N-(4-cyanophenyl)) | B |

TABLE 2-continued

| Cpd | Cpd | mGluR1 IC$_{50}$ rating |
|---|---|---|
| 19BC | | B |
| 19BD | | A |
| 19BE | | A |
| 19BF | | B |
| 19BG | | B |
| 19BH | | B |

TABLE 2-continued

| Cpd | Cpd | mGluR1 IC$_{50}$ rating |
|---|---|---|
| 23A | (structure) | A |
| 23B | (structure) | C |
| 23C | (structure) | B |
| 26A | (structure) | A |
| 26B | (structure) | B |
| 26C | (structure) | B |

TABLE 2-continued

| Cpd | Cpd | mGluR1 IC$_{50}$ rating |
|---|---|---|
| 26D | (cyclopropyl-NH substituted pyrido-thieno-pyrimidinone with 4-methoxyphenyl) | A |
| 26E | (cyclopropyl-NH substituted pyrido-thieno-pyrimidinone with 4-methylphenyl) | A |
| 26F | (methyl-NH substituted pyrido-thieno-pyrimidinone with 4-methylphenyl) | B |
| 26G | (dimethylamino substituted pyrido-thieno-pyrimidinone with 4-methylphenyl) | A |
| 26H | (ethyl-NH substituted pyrido-thieno-pyrimidinone with 4-methylphenyl) | A |

Specific IC$_{50}$ values for some representative compounds are shown in Table 3 below.
TABLE 3
| Cpd | Cpd | mGluR1 IC$_{50}$ (nM) |
|---|---|---|
| 9A | 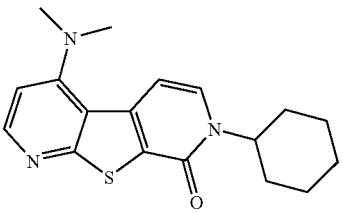 | 8.1 |
| 9B | 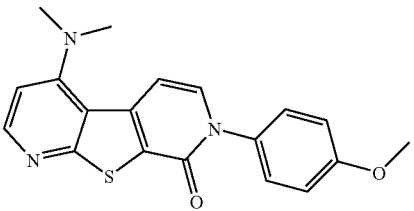 | 6.3 |
| 9C | 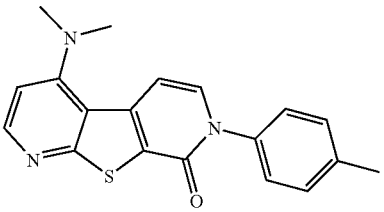 | 4.7 |
| 9D | 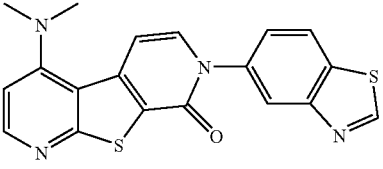 | 5.0 |
| 9E | 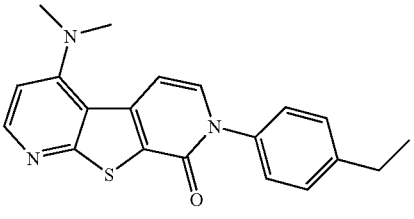 | 8.2 |
| 9F | 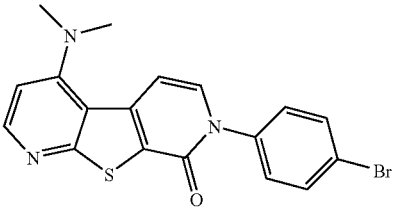 | 5.7 |
| 9G | 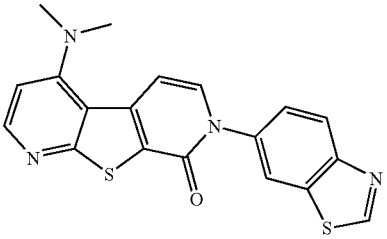 | 3.1 |

TABLE 3-continued
| Cpd | Cpd | mGluR1 IC$_{50}$ (nM) |
|---|---|---|
| 16A | 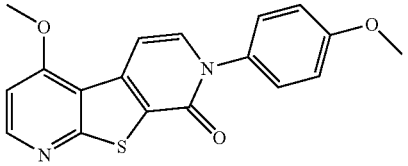 | 6.3 |
| 16B | 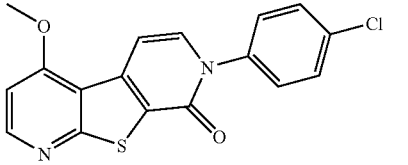 | 3.4 |
| 16C | 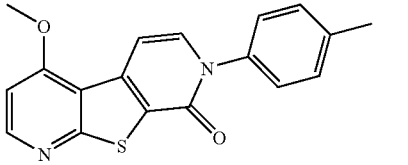 | 3.9 |
| 16E | 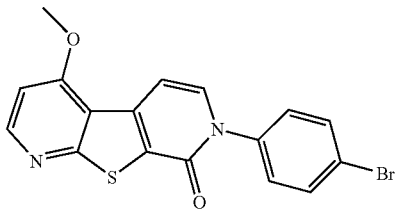 | 4.8 |
| 19A | 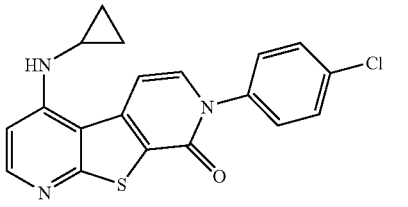 | 4.4 |
| 19B | 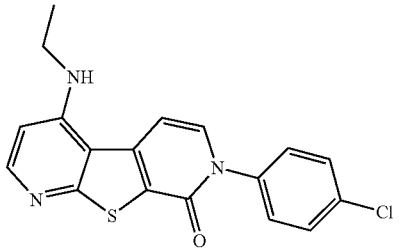 | 3.0 |
| 19K | 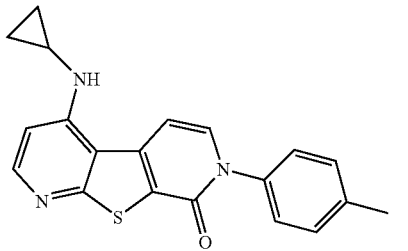 | 9.8 |

TABLE 3-continued

| Cpd | Cpd | mGluR1 IC$_{50}$ (nM) |
|---|---|---|
| 19O | | 14.8 |
| 19P | | 12.2 |
| 19AS | | 3.9 |
| 19AV | | 9.8 |
| 19AW | | 0.8 |
| 19AX | | 2.0 |

TABLE 3-continued

| Cpd | Cpd | mGluR1 IC$_{50}$ (nM) |
|---|---|---|
| 19AY | | 2.3 |
| 19BE | | 14.3 |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A compound of formula I:

formula I or a pharmaceutically acceptable salt, or ester thereof, wherein:

J$^1$ is N; J$^2$, and J$^3$ are independently C;

⋯ is a single or double bond;

R$^1$ is phenyl optionally substituted with at least one R$^8$;

X is —NR$^5$R$^6$;

Z is S;

R$^2$ and R$^3$ are each independently H;

R$^4$ is H;

w is an integer ranging from 1-2;

R$^5$ is selected from the group consisting of H, —NH$_2$, alkyl, alkenyl, alkynyl, and cycloalkyl groups optionally substituted with at least one R$^8$;

R$^6$ and R$^7$ are independently selected from the group consisting of H and alkyl, alkenyl, alkynyl, and cycloalkyl;

R$^8$ is selected from the group consisting of H, halo, —OR$^9$, NO$_2$, —CN, —NR$^9$C(O)R$^{10}$, —NR$^9$SO$_2$R$^{11}$, —NR$^9$R$^{10}$, —C(O)R$^{10}$, —C(O)NR$^5$R$^6$, S(O$_2$)NR$^5$R$^6$, and alkyl, alkoxy, alkenyl, alkenyloxy, alkynyl, cycloalkyl, cycloalkoxy, aryl, aryloxy, and arylalkyl, groups optionally substituted with at least one of halo, —CN, —NO$_2$, —OR$^6$, —SR$^{11}$, —NR$^5$R$^6$, —C(O)R$^6$, —C(O$_2$)R$^6$, —OC(O)R$^6$, —C(O)NR$^6$R$^7$, —N(R$^6$)C(O) R$^6$, —OS(O$_2$)R$^{11}$, —S(O$_2$)R$^{11}$, —S(O$_2$)NR$^5$R$^6$, —N(R$^6$)S(O$_2$)R$^{11}$, —N(R$^6$)C(O)NR$^5$R$^6$, and —NR$^9$SO$_2$R$^{11}$;

R$^9$ is selected from the group consisting of H, and alkyl, alkenyl, alkynyl, cycloalkyl, aryl, and arylalkyl, groups optionally substituted with at least one of halo, —CN, —NO$_2$, —OR$^6$, —SR$^{11}$, —NR$^5$R$^6$, —C(O)R$^6$, —C(O$_2$) R$^6$, —OC(O)R$^6$, —C(O)NR$^6$R$^7$, —N(R$^6$)C(O)R$^6$, —OS(O$_2$)R$^{11}$, —S(O$_2$)R$^{11}$, —S(O$_2$)NR$^5$R$^6$, —N(R$^6$)S (O$_2$)R$^{11}$, and —N(R$^6$)C(O)NR$^5$R$^6$;

R$^{10}$ is selected from the group consisting of H and alkyl, alkoxy, alkenyl, alkenyloxy, alkynyl, cycloalkyl, cycloalkoxy, aryl, aryloxy, and arylalkyl, groups optionally substituted with at least one of halo, —CN, —NO$_2$, —OR$^6$, —SR$^{11}$, —NR$^5$R$^6$, —C(O)R$^6$, —C(O$_2$)R$^6$, —OC(O)R$^6$, —C(O)NR$^6$R$^7$, —N(R$^6$)C(O)R$^6$, —OS (O$_2$)R$^{11}$, —S(O$_2$)R$^{11}$, —S(O$_2$)NR$^5$R$^6$, —N(R$^6$)S(O$_2$) R$^{11}$, and —N(R$^6$)C(O)NR$^5$R$^6$; and R$^{11}$ is selected from the group consisting of alkyl, alkenyl, alkynyl, cycloalkyl, aryl, and arylalkyl, groups optionally substituted with at least one R$^8$.

2. The compound of claim 1, wherein Z is S, J$^1$ is N, J$^2$ and J$^3$ are each C, X is —NR$^5$R$^6$, R$^2$, R$^3$ and R$^5$ are H, R$^6$ is cyclopropyl, w is 0, and R$^1$ is p-methoxyphenyl.

3. The compound of claim 1, wherein Z is S, J$^1$ is N, and J$^2$ and J$^3$ are each C.

4. The compound of claim 1, wherein X is —NR$^5$R$^6$.

5. The compound of claim 4, wherein R$^5$ and R$^6$ are independently selected from the group consisting of hydrogen, and alkyl and cycloalkyl groups optionally substituted with at least one R$^8$.

6. The compound of claim 4, wherein R$^5$ and R$^6$ are each alkyl.

7. The compound of claim 4, wherein R$^5$ is H and R$^6$ is alkyl which is optionally substituted with at least one substituent selected from the group consisting of —OH, alkoxy, —CF$_3$, and —C≡CH.

8. The compound of claim 4, wherein at least one of R$^5$ and R$^6$ is cycloalkyl.

9. The compound of claim 7, $R^5$ is H and $R^6$ is cyclopropyl.

10. The compound of claim 1, wherein $R^2$ and $R^3$ are H.

11. The compound of claim 1, wherein $R^1$ is phenyl which is optionally substituted with at least one $R^8$.

12. The compound of claim 11, wherein said $R^8$ is selected from the group consisting of alkyl, cycloalkyl, cyano, alkoxy, halo, and hydroxy.

13. A compound of formula V:

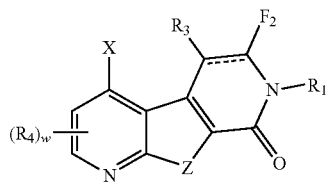

Formula V or a pharmaceutically acceptable salt, solvate, or ester thereof, wherein:

Z, X, $R^1$, $R^2$, $R^3$, $R^4$, $R^5$, and w are as defined in claim 1.

14. The compound of claim 1, wherein the compound is selected from the group consisting of those set forth below or a pharmaceutically acceptable salt, solvate, or ester thereof

| Cpd | Structure |
|---|---|
| 19F | (structure: 4-(2-hydroxyethylamino)-substituted pyrido-thieno-pyridinone with 4-chlorophenyl) |
| 19G | (structure: 4-(2-methoxyethylamino)-substituted pyrido-thieno-pyridinone with 4-chlorophenyl) |
| 19H | (structure: 4-(3-methoxypropylamino)-substituted pyrido-thieno-pyridinone with 4-chlorophenyl) |
| 19I | (structure: 4-(2,2,2-trifluoroethylamino)-substituted pyrido-thieno-pyridinone with 4-chlorophenyl) |
| 19J | (structure: 4-(2-methoxyethylamino)-substituted pyrido-thieno-pyridinone with 4-hydroxyphenyl) |
| 19K | (structure: 4-(cyclopropylamino)-substituted pyrido-thieno-pyridinone with 4-methylphenyl) |
| 19L | (structure: 4-(2-hydroxyethylamino)-substituted pyrido-thieno-pyridinone with 4-methylphenyl) |
| 19M | (structure: 4-((S)-2-hydroxypropylamino)-substituted pyrido-thieno-pyridinone with 4-methylphenyl) |
| 19N | (structure: 4-(ethylamino)-substituted pyrido-thieno-pyridinone with 4-methylphenyl) |
| 19O | (structure: 4-(ethylamino)-substituted pyrido-thieno-pyridinone with 4-methoxyphenyl) |
| 19P | (structure: 4-(cyclopropylamino)-substituted pyrido-thieno-pyridinone with 4-methoxyphenyl) |

-continued
| Cpd | Structure |
|---|---|
| 19Q | 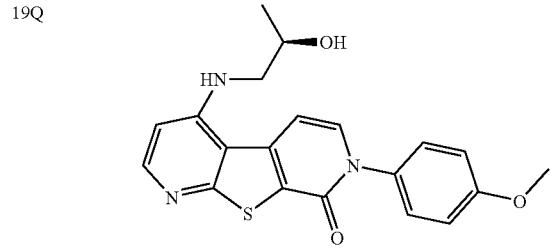 |
| 19R | 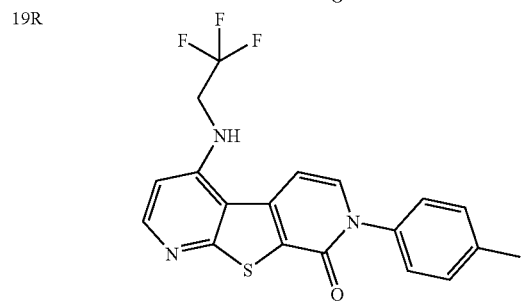 |
| 19S | 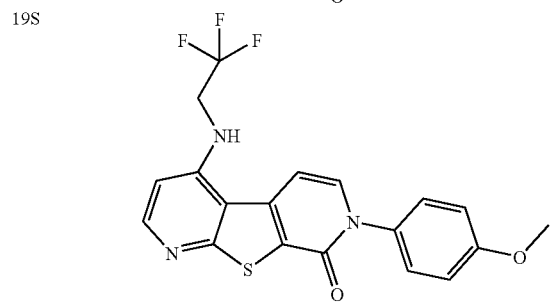 |
| 19T | 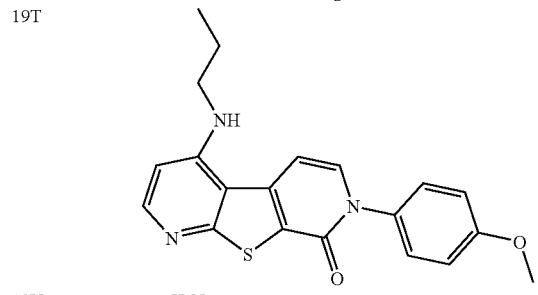 |
| 19U | 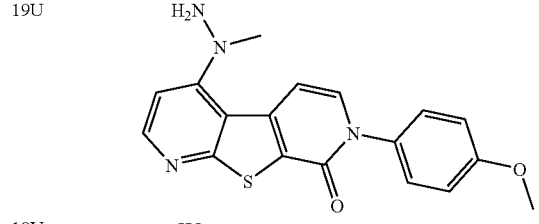 |
| 19V | 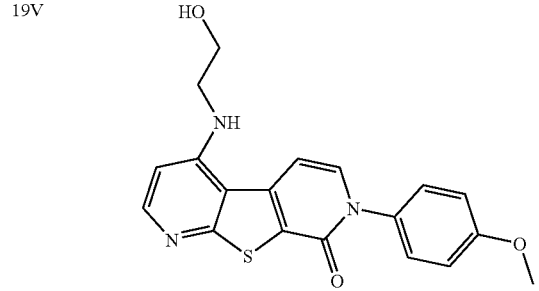 |
-continued
| Cpd | Structure |
|---|---|
| 19W | 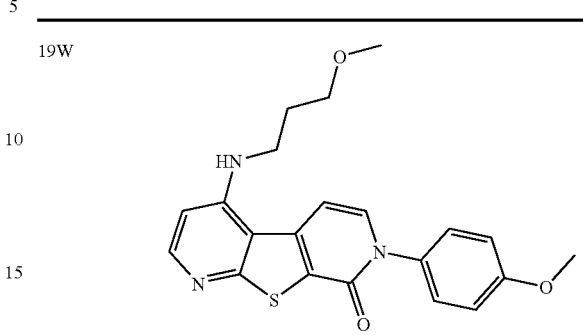 |
| 19X | 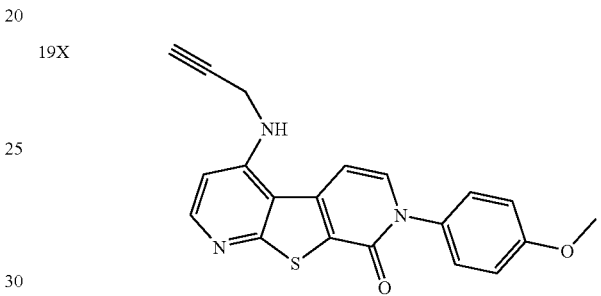 |
| 19Y | 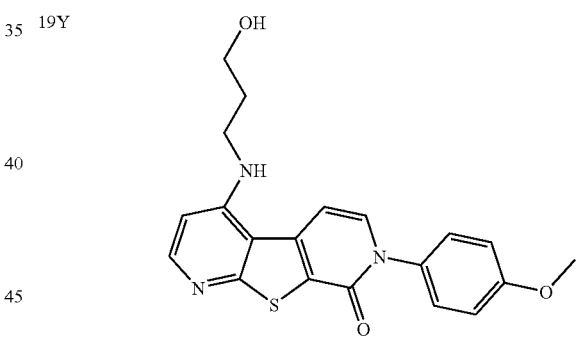 |
| 19Z | 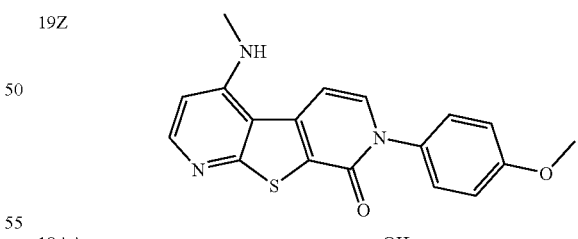 |
| 19AA | 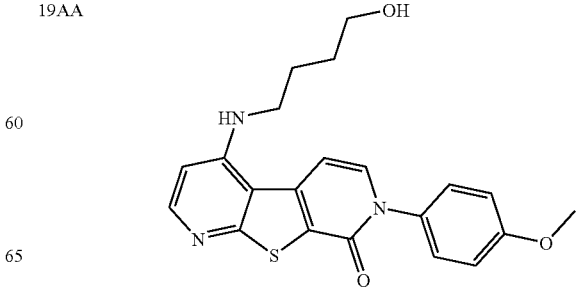 |

-continued

| Cpd | Structure |
|---|---|
| 19AB | (structure) |
| 19AC | (structure) |
| 19AD | (structure) |
| 19AE | (structure) |
| 19AF | (structure) |
| 19AG | (structure) |

-continued

| Cpd | Structure |
|---|---|
| 19AH | (structure) |
| 19AI | (structure) |
| 19AJ | (structure) |
| 19AK | (structure) |
| 19AL | (structure) |
| 19AM | (structure) |

-continued
| Cpd | Structure |
|---|---|
| 19AN | 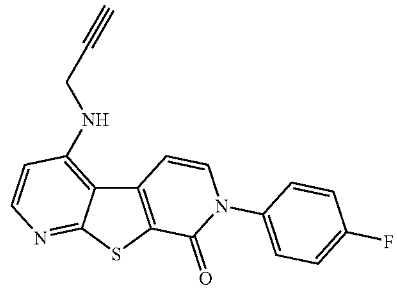 |
| 19AO | 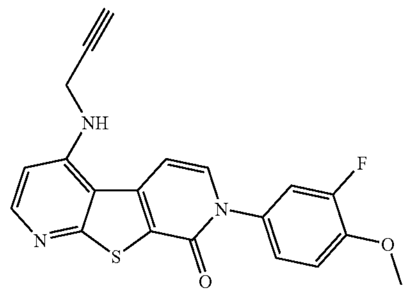 |
| 19AS | 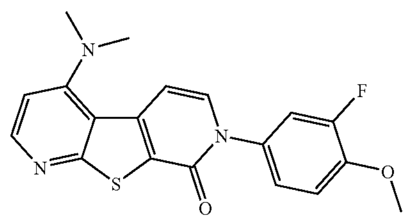 |
| 19AT | 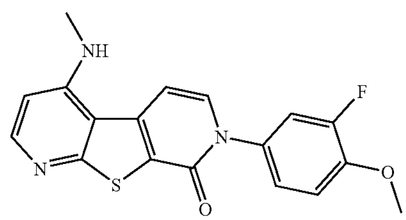 |
| 19AU | 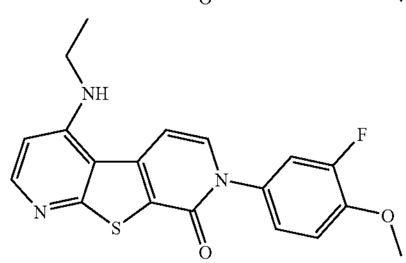 |
| 19AV | 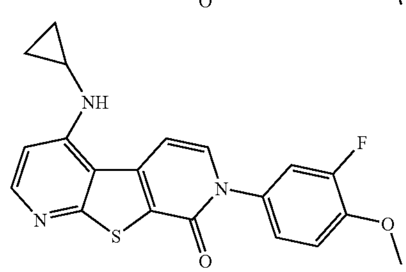 |
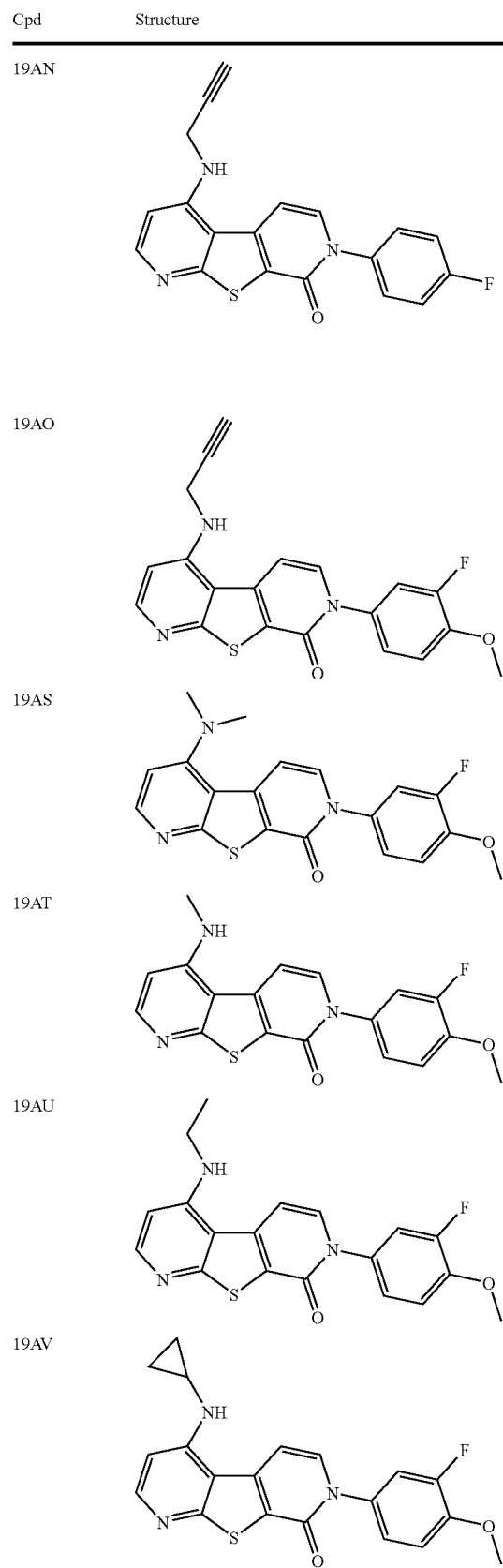
-continued
| Cpd | Structure |
|---|---|
| 19AW | 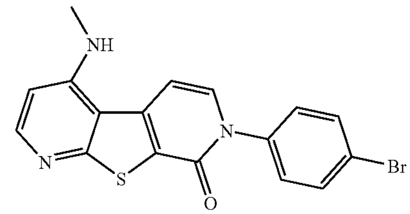 |
| 19AX | 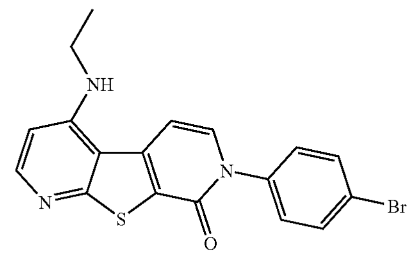 |
| 19AY | 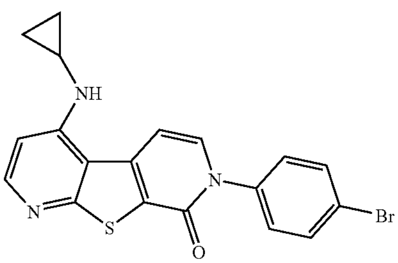 |
| 19AZ | 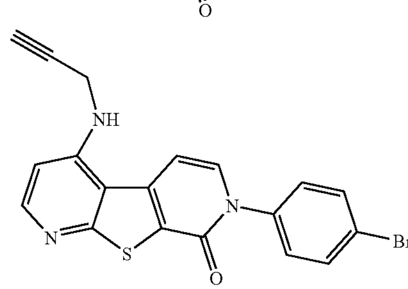 |
| 19BA | 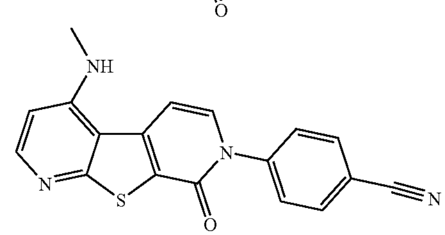 |
| 19BB | 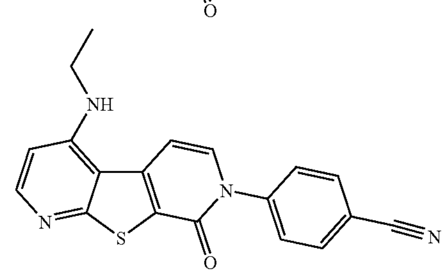 |
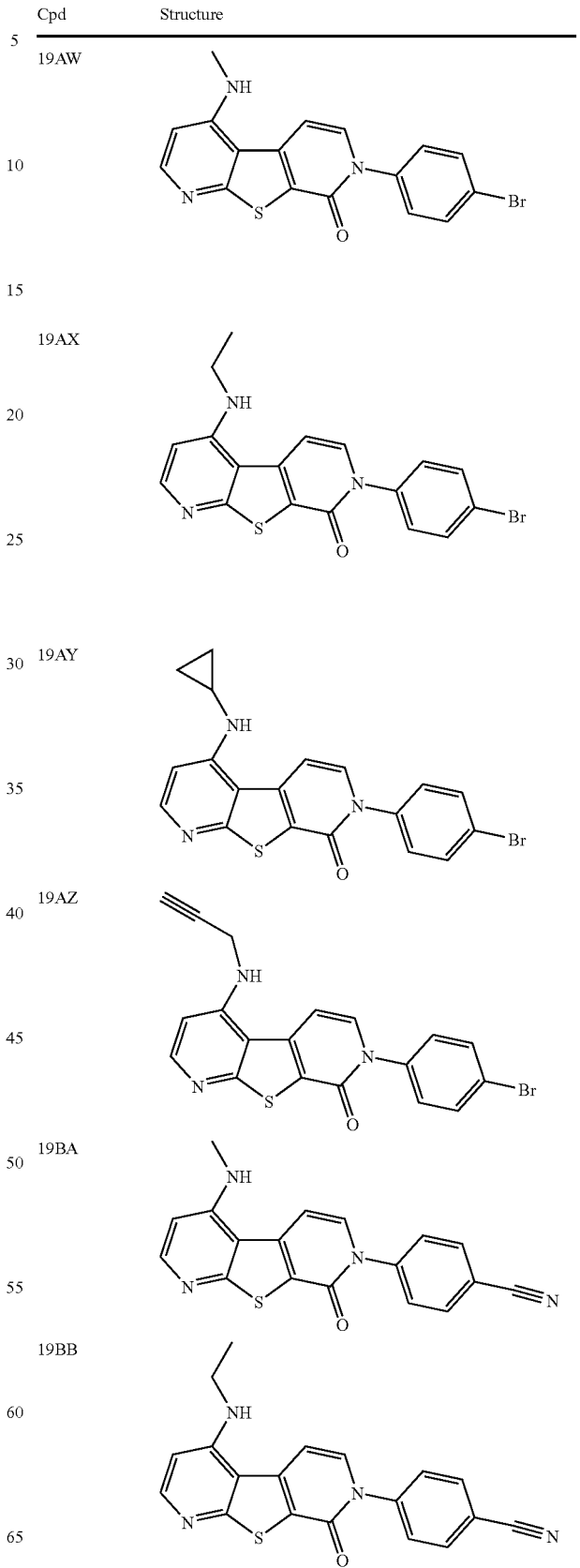

-continued

| Cpd | Structure |
|---|---|
| 19BC | 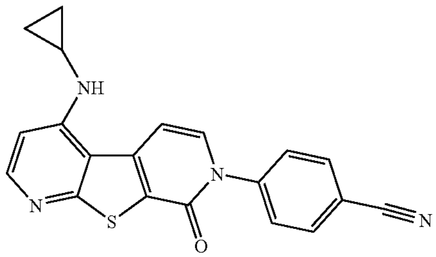 |
| 19BD | 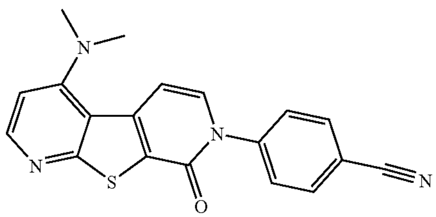 |
| 19BE | 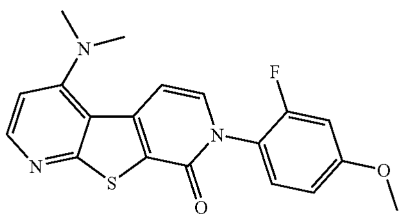 |
| 19BF | 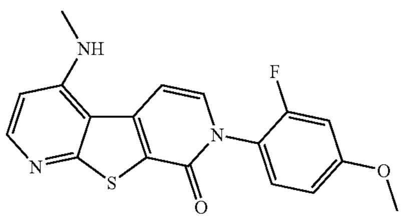 |
| 19BG | 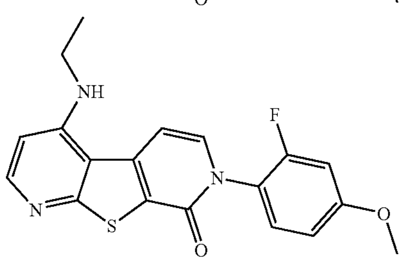 |
| 19BH | 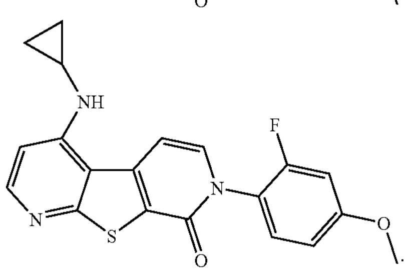 |

15. A compound selected from the group consisting of

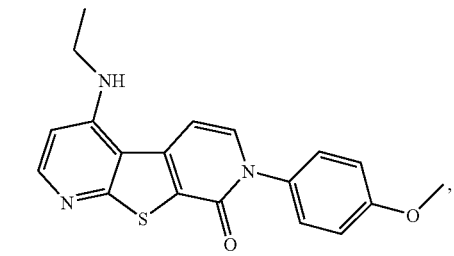

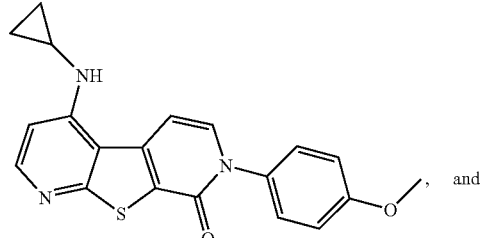, and

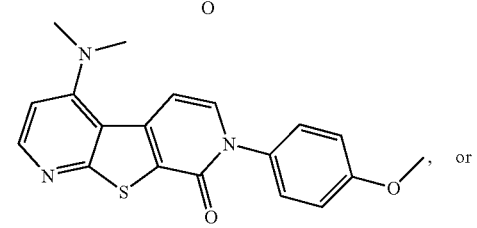, or or a pharmaceutically acceptable salt, or thereof.

16. A pharmaceutical composition comprising at least one compound of claim 1, or a pharmaceutically acceptable salt, or ester thereof and at least one pharmaceutically acceptable carrier, adjuvant or vehicle.

17. A pharmaceutical composition comprising at least one compound of claim 14, or a pharmaceutically acceptable salt, or ester thereof and at least one pharmaceutically acceptable carrier, adjuvant or vehicle.

18. The pharmaceutical composition of claim 15, further comprising one or more additional therapeutic agents.

19. The pharmaceutical composition of claim 16, further comprising one or more additional therapeutic agents.

20. The pharmaceutical composition of claim 17, wherein said additional therapeutic agents are selected from the group consisting of therapeutic agents suitable for pain management, anti-anxiety agents, anti-migraine agents, and therapeutic agents suitable for treating urinary incontinence.

21. The pharmaceutical composition of claim 18, wherein said additional therapeutic agents are selected from the group consisting of therapeutic agents suitable for pain management, anti-anxiety agents, anti-migraine agents, and therapeutic agents suitable for treating urinary incontinence.

22. A method of selectively antagonizing metabotropic glutamate receptor 1 (mGluR1) activity in a cell in need thereof, comprising contacting said cell with a effective amount of at least one compound of claim 1.

* * * * *